United States Patent
Capra et al.

(10) Patent No.: US 9,872,790 B2
(45) Date of Patent: Jan. 23, 2018

(54) METHODS AND DEVICES FOR PROVIDING AUTOMATIC CLOSURE OF PROSTHETICS AND ORTHOTICS

(71) Applicant: Boa Technology, Inc., Denver, CO (US)

(72) Inventors: James Capra, Steamboat Springs, CO (US); Mark Soderberg, Conifer, CO (US); Aaron Venturini, Denver, CO (US); Kristopher Lovett, Denver, CO (US)

(73) Assignee: Boa Technology Inc., Denver, CO (US)

( * ) Notice: Subject to any disclaimer, the term of this patent is extended or adjusted under 35 U.S.C. 154(b) by 398 days.

(21) Appl. No.: 14/546,883

(22) Filed: Nov. 18, 2014

(65) Prior Publication Data

US 2015/0150705 A1    Jun. 4, 2015

Related U.S. Application Data

(60) Provisional application No. 61/905,753, filed on Nov. 18, 2013.

(51) Int. Cl.
*A61F 5/01* (2006.01)

(52) U.S. Cl.
CPC .............. *A61F 5/0102* (2013.01); *A61F 5/01* (2013.01); *A61F 5/0109* (2013.01); *A61F 2250/001* (2013.01)

(58) Field of Classification Search
CPC .. A61F 5/00; A61F 5/01; A61F 5/0102; A61F 5/0104; A61F 5/0106;

(Continued)

(56) References Cited

U.S. PATENT DOCUMENTS

| 59,332 A | 10/1866 | White et al. |
| 80,834 A | 8/1868 | Prussia |

(Continued)

FOREIGN PATENT DOCUMENTS

| AT | 127075 | 2/1932 |
| AT | 244804 | 1/1966 |

(Continued)

OTHER PUBLICATIONS

ASOLO® Boot Brochure Catalog upon information and belief date is as early as Aug. 22, 1997.

(Continued)

*Primary Examiner* — Keri J Nelson
(74) *Attorney, Agent, or Firm* — Kilpatrick Townsend & Stockton LLP

(57) ABSTRACT

According to an embodiment, a lacing system for opening and closing an article includes a tensioning device having a first mode of operation and a second mode of operation, a first tension member that is coupled with the tensioning device and tensionable thereby, and a second tension member that is coupled with the tensioning device and tensionable thereby. The tensioning device is configured to: effect tensioning of the first tension member to close and tighten the article upon operation of the tensioning device in the first mode of operation and effect tensioning of the second tension member to loosen and open the article upon operation of the tensioning device in the second mode of operation.

38 Claims, 34 Drawing Sheets

(58) Field of Classification Search
CPC .... A61F 5/0109; A61F 5/0111; A61F 5/0118; A61F 5/0123; A61F 5/0127; A61F 5/013; A61F 5/02; A61F 5/022; A61F 5/024; A61F 5/026; A61F 5/028; A61F 2250/0004; A61F 2250/001; A61F 2002/5026
USPC .............................. 602/5, 6, 12, 19, 20, 23
See application file for complete search history.

(56) References Cited

U.S. PATENT DOCUMENTS

| | | |
|---|---|---|
| 117,530 A | 8/1871 | Foote |
| 228,946 A | 6/1880 | Schulz |
| 230,759 A | 8/1880 | Drummond |
| 379,113 A | 3/1888 | Hibberd |
| 746,563 A | 12/1903 | McMahon |
| 819,993 A | 5/1906 | Haws et al. |
| 908,704 A | 1/1909 | Sprinkle |
| 1,060,422 A | 4/1913 | Bowdish |
| 1,062,511 A | 5/1913 | Short |
| 1,083,775 A | 1/1914 | Thomas |
| 1,090,438 A | 3/1914 | Worth et al. |
| 1,170,472 A | 2/1916 | Barber |
| 1,288,859 A | 12/1918 | Feller et al. |
| 1,390,991 A | 9/1921 | Fotchuk |
| 1,393,188 A | 10/1921 | Whiteman |
| 1,469,661 A | 2/1922 | Migita |
| 1,412,486 A | 4/1922 | Paine |
| 1,416,203 A | 5/1922 | Hobson |
| 1,429,657 A | 9/1922 | Trawinski |
| 1,481,903 A | 4/1923 | Hart |
| 1,466,673 A | 9/1923 | Solomon et al. |
| 1,530,713 A | 2/1924 | Clark |
| 1,502,919 A | 7/1924 | Seib |
| 1,862,047 A | 6/1932 | Boulet et al. |
| 1,995,243 A | 6/1934 | Clarke |
| 2,088,851 A | 8/1937 | Gantenbein |
| 2,109,751 A | 3/1938 | Matthias et al. |
| 2,124,310 A | 9/1938 | Murr, Jr. |
| 2,316,102 A | 4/1943 | Preston |
| 2,500,622 A * | 3/1950 | Aho .................... A61F 2/80 623/36 |
| 2,539,026 A | 1/1951 | Mangold |
| 2,611,940 A | 9/1952 | Cairns |
| 2,673,381 A | 3/1954 | Dueker |
| 2,907,086 A | 10/1959 | Ord |
| 2,991,523 A | 7/1961 | Del Conte |
| 3,028,602 A | 4/1962 | Miller |
| 3,035,319 A | 5/1962 | Wolff |
| 3,106,003 A | 10/1963 | Herdman |
| 3,112,545 A | 12/1963 | Williams |
| 3,122,810 A | 3/1964 | Lawrence et al. |
| 3,163,900 A | 1/1965 | Martin |
| D200,394 S | 2/1965 | Hakim |
| 3,169,325 A | 2/1965 | Fesl |
| 3,193,950 A | 7/1965 | Shu-Lien Liou |
| 3,197,155 A | 7/1965 | Chow |
| 3,221,384 A | 12/1965 | Aufenacker |
| 3,276,090 A | 10/1966 | Nigon |
| D206,146 S | 11/1966 | Hendershot |
| 3,345,707 A | 10/1967 | Rita |
| D210,649 S | 4/1968 | Getgay |
| 3,401,437 A | 9/1968 | Christpohersen |
| 3,430,303 A | 3/1969 | Perrin et al. |
| 3,491,465 A | 1/1970 | Martin |
| 3,545,106 A | 12/1970 | Martin |
| 3,618,232 A | 11/1971 | Shnuriwsky |
| 3,668,791 A | 6/1972 | Salzman et al. |
| 3,678,539 A | 7/1972 | Graup |
| 3,703,775 A | 11/1972 | Gatti |
| 3,729,779 A | 5/1973 | Porth |
| 3,738,027 A | 6/1973 | Schoch |
| 3,793,749 A | 2/1974 | Gertsch et al. |
| 3,808,644 A | 5/1974 | Schoch |
| 3,934,346 A | 1/1976 | Sasaki et al. |
| 3,975,838 A | 8/1976 | Martin |
| 4,084,267 A | 4/1978 | Zadina |
| 4,130,949 A | 12/1978 | Seidel |
| 4,142,307 A | 3/1979 | Martin |
| 4,227,322 A | 10/1980 | Annovi |
| 4,261,081 A | 4/1981 | Lott |
| 4,267,622 A | 5/1981 | Burnett-Johnston |
| 4,408,403 A | 10/1983 | Martin |
| 4,417,703 A | 11/1983 | Weinhold |
| 4,433,456 A | 2/1984 | Baggio |
| 4,463,761 A | 8/1984 | Pols et al. |
| 4,480,395 A | 11/1984 | Schoch |
| 4,507,878 A | 4/1985 | Semouha |
| 4,516,576 A | 5/1985 | Kirchner |
| 4,551,932 A | 11/1985 | Schoch |
| 4,555,830 A | 12/1985 | Petrini et al. |
| 4,574,500 A | 3/1986 | Aldinio et al. |
| 4,616,432 A | 10/1986 | Bunch et al. |
| 4,616,524 A | 10/1986 | Bidoia |
| 4,619,057 A | 10/1986 | Sartor et al. |
| 4,620,378 A | 11/1986 | Sartor |
| 4,631,839 A | 12/1986 | Bonetti et al. |
| 4,631,840 A | 12/1986 | Gamm |
| 4,633,599 A | 1/1987 | Morell et al. |
| 4,644,938 A | 2/1987 | Yates et al. |
| 4,654,985 A | 4/1987 | Chalmers |
| 4,660,300 A | 4/1987 | Morell et al. |
| 4,660,302 A | 4/1987 | Arieh et al. |
| 4,680,878 A | 7/1987 | Pozzobon et al. |
| 4,719,670 A | 1/1988 | Kurt |
| 4,719,709 A | 1/1988 | Vaccari |
| 4,719,710 A | 1/1988 | Pozzobon |
| 4,722,477 A | 2/1988 | Floyd |
| 4,741,115 A | 5/1988 | Pozzobon |
| 4,748,726 A | 6/1988 | Schoch |
| 4,760,653 A | 8/1988 | Baggio |
| 4,780,969 A | 11/1988 | White, Jr. |
| 4,787,124 A | 11/1988 | Pozzobon et al. |
| 4,790,081 A | 12/1988 | Benoit et al. |
| 4,796,829 A | 1/1989 | Pozzobon et al. |
| 4,799,297 A | 1/1989 | Baggio et al. |
| 4,802,291 A | 2/1989 | Sartor |
| 4,811,503 A | 3/1989 | Iwama |
| 4,826,098 A | 5/1989 | Pozzobon et al. |
| 4,841,649 A | 6/1989 | Baggio et al. |
| 4,856,207 A | 8/1989 | Datson |
| 4,862,878 A | 9/1989 | Davison et al. |
| 4,870,723 A | 10/1989 | Pozzobon et al. |
| 4,870,761 A | 10/1989 | Tracy |
| 4,884,760 A | 12/1989 | Baggio et al. |
| 4,901,938 A | 2/1990 | Cantley et al. |
| 4,924,605 A | 5/1990 | Spademan |
| D308,282 S | 6/1990 | Bergman et al. |
| 4,937,953 A | 7/1990 | Walkhoff |
| 4,961,544 A | 10/1990 | Bidoia |
| 4,979,953 A | 12/1990 | Spence |
| 4,989,805 A | 2/1991 | Burke |
| 5,001,817 A | 3/1991 | De Bortoli et al. |
| 5,016,327 A | 5/1991 | Klausner |
| 5,042,177 A | 8/1991 | Schoch |
| 5,062,225 A | 11/1991 | Gorza |
| 5,065,480 A | 11/1991 | DeBortoli |
| 5,065,481 A | 11/1991 | Walkhoff |
| 5,108,216 A | 4/1992 | Geyer et al. |
| 5,117,567 A | 6/1992 | Berger |
| 5,152,038 A | 10/1992 | Schoch |
| 5,157,813 A | 10/1992 | Carroll |
| 5,158,428 A | 10/1992 | Gessner et al. |
| 5,177,882 A | 1/1993 | Berger |
| 5,181,331 A | 1/1993 | Berger |
| 5,184,378 A | 2/1993 | Batra |
| D333,552 S | 3/1993 | Berger et al. |
| 5,205,055 A | 4/1993 | Harrell |
| 5,233,767 A | 8/1993 | Kramer |
| 5,249,377 A | 10/1993 | Walkhoff |
| 5,259,094 A | 11/1993 | Zepeda |
| 5,315,741 A | 5/1994 | Dubberke |
| 5,319,868 A | 6/1994 | Hallenbeck |

(56) References Cited

U.S. PATENT DOCUMENTS

| | | |
|---|---|---|
| 5,319,869 A | 6/1994 | McDonald et al. |
| 5,325,613 A | 7/1994 | Sussmann |
| 5,327,662 A | 7/1994 | Hallenbeck |
| 5,335,401 A | 8/1994 | Hanson |
| 5,341,583 A | 8/1994 | Hallenbeck |
| 5,345,697 A | 9/1994 | Quellais |
| 5,355,596 A | 10/1994 | Sussmann |
| 5,357,654 A | 10/1994 | Hsing-Chi |
| 5,371,957 A | 12/1994 | Gaudio |
| 5,381,609 A | 1/1995 | Hieblinger |
| 5,392,535 A | 2/1995 | Van Noy et al. |
| D357,576 S | 4/1995 | Steinweis |
| 5,425,161 A | 6/1995 | Schoch |
| 5,425,185 A | 6/1995 | Gansler |
| 5,430,960 A | 7/1995 | Richardson |
| 5,433,648 A | 7/1995 | Frydman |
| 5,463,822 A | 11/1995 | Miller |
| 5,477,593 A | 12/1995 | Leick |
| D367,755 S | 3/1996 | Jones |
| D367,954 S | 3/1996 | Dion |
| 5,502,902 A | 4/1996 | Sussmann |
| 5,511,325 A | 4/1996 | Hieblinger |
| 5,526,585 A | 6/1996 | Brown et al. |
| 5,535,531 A | 7/1996 | Karabed et al. |
| 5,537,763 A | 7/1996 | Donnadieu et al. |
| 5,557,864 A | 9/1996 | Marks |
| 5,566,474 A | 10/1996 | Leick et al. |
| D375,831 S | 11/1996 | Perry |
| 5,596,820 A | 1/1997 | Edauw et al. |
| 5,599,000 A | 2/1997 | Bennett |
| 5,599,288 A | 2/1997 | Shirley et al. |
| 5,600,874 A | 2/1997 | Jungkind |
| 5,606,778 A | 3/1997 | Jungkind |
| 5,607,448 A | 3/1997 | Stahl et al. |
| D379,113 S | 5/1997 | McDonald et al. |
| 5,638,588 A | 6/1997 | Jungkind |
| 5,640,785 A | 6/1997 | Egelja |
| 5,647,104 A | 7/1997 | James |
| 5,651,198 A | 7/1997 | Sussmann |
| 5,669,116 A | 9/1997 | Jungkind |
| 5,692,319 A | 12/1997 | Parker et al. |
| 5,718,021 A | 2/1998 | Tatum |
| 5,718,065 A | 2/1998 | Locker |
| 5,720,084 A | 2/1998 | Chen |
| 5,732,483 A | 3/1998 | Cagliari |
| 5,732,648 A | 3/1998 | Aragon |
| 5,736,696 A | 4/1998 | Del Rosso |
| 5,737,854 A | 4/1998 | Sussmann |
| 5,755,044 A | 5/1998 | Veylupek |
| 5,756,298 A | 5/1998 | Burczak |
| 5,761,777 A | 6/1998 | Leick |
| 5,772,146 A | 6/1998 | Kawamoto et al. |
| 5,784,809 A | 7/1998 | McDonald |
| 5,791,068 A | 8/1998 | Bernier et al. |
| 5,819,378 A | 10/1998 | Doyle |
| 5,833,640 A | 11/1998 | Vazquez, Jr. et al. |
| 5,839,210 A | 11/1998 | Bernier et al. |
| 5,845,371 A | 12/1998 | Chen |
| 5,909,946 A | 6/1999 | Okajima |
| D413,197 S | 8/1999 | Faye |
| 5,934,599 A | 8/1999 | Hammerslag |
| 5,937,542 A | 8/1999 | Bourdeau |
| 5,956,823 A | 9/1999 | Borel |
| 5,971,946 A | 10/1999 | Quinn et al. |
| 6,015,110 A | 1/2000 | Lai |
| 6,038,791 A | 3/2000 | Cornelius et al. |
| 6,052,921 A | 4/2000 | Oreck |
| 6,070,886 A | 6/2000 | Cornelius et al. |
| 6,070,887 A | 6/2000 | Cornelius et al. |
| 6,083,857 A | 7/2000 | Bottger |
| 6,088,936 A | 7/2000 | Bahl |
| 6,102,412 A | 8/2000 | Staffaroni |
| D430,724 S | 9/2000 | Matis et al. |
| 6,119,318 A | 9/2000 | Maurer |
| 6,119,372 A | 9/2000 | Okajima |
| 6,128,835 A | 10/2000 | Ritter et al. |
| 6,128,836 A | 10/2000 | Barret |
| 6,148,489 A | 11/2000 | Dickie et al. |
| 6,202,953 B1 | 3/2001 | Hammerslag |
| 6,219,891 B1 | 4/2001 | Maurer et al. |
| 6,240,657 B1 | 6/2001 | Weber et al. |
| 6,256,798 B1 | 7/2001 | Egolf et al. |
| 6,267,390 B1 | 7/2001 | Maravetz et al. |
| 6,286,233 B1 | 9/2001 | Gaither |
| 6,289,558 B1 | 9/2001 | Hammerslag |
| 6,311,633 B1 | 11/2001 | Keire |
| D456,130 S | 4/2002 | Towns |
| 6,370,743 B2 | 4/2002 | Choe |
| 6,401,364 B1 | 6/2002 | Burt |
| 6,416,074 B1 | 7/2002 | Maravetz et al. |
| 6,467,195 B2 | 10/2002 | Pierre et al. |
| 6,477,793 B1 | 11/2002 | Pruitt et al. |
| 6,502,286 B1 | 1/2003 | Dubberke |
| 6,543,159 B1 | 4/2003 | Carpenter et al. |
| 6,568,103 B2 | 5/2003 | Durocher |
| 6,606,804 B2 | 8/2003 | Kaneko et al. |
| 6,694,643 B1 | 2/2004 | Hsu |
| 6,708,376 B1 | 3/2004 | Landry |
| 6,711,787 B2 | 3/2004 | Jungkind et al. |
| 6,735,829 B2 | 5/2004 | Hsu |
| 6,757,991 B2 | 7/2004 | Sussmann |
| 6,775,928 B2 | 8/2004 | Grande et al. |
| 6,792,702 B2 | 9/2004 | Borsoi et al. |
| 6,802,439 B2 | 10/2004 | Azam et al. |
| 6,823,610 B1 | 11/2004 | Ashley |
| 6,871,812 B1 | 3/2005 | Chang |
| 6,877,256 B2 | 4/2005 | Martin et al. |
| 6,899,720 B1 | 5/2005 | McMillan |
| 6,922,917 B2 | 8/2005 | Kerns et al. |
| 6,938,913 B2 | 9/2005 | Elkington |
| 6,945,543 B2 | 9/2005 | De Bortoli et al. |
| D510,183 S | 10/2005 | Tresser |
| 6,976,972 B2 | 12/2005 | Bradshaw |
| 6,993,859 B2 | 2/2006 | Martin et al. |
| D521,226 S | 5/2006 | Douglas et al. |
| 7,073,279 B2 | 7/2006 | Min |
| 7,076,843 B2 | 7/2006 | Sakabayashi |
| 7,082,701 B2 | 8/2006 | Dalgaard et al. |
| 7,096,559 B2 | 8/2006 | Johnson et al. |
| 7,134,224 B2 | 11/2006 | Elkington et al. |
| 7,266,911 B2 | 9/2007 | Holzer et al. |
| 7,281,341 B2 | 10/2007 | Reagan et al. |
| 7,293,373 B2 | 11/2007 | Reagan et al. |
| 7,331,126 B2 | 2/2008 | Johnson |
| 7,343,701 B2 | 3/2008 | Pare et al. |
| 7,367,522 B2 | 5/2008 | Chen |
| 7,386,947 B2 | 6/2008 | Martin et al. |
| 7,392,602 B2 | 7/2008 | Reagan et al. |
| 7,401,423 B2 | 7/2008 | Reagan et al. |
| 7,490,458 B2 | 2/2009 | Ford |
| 7,568,298 B2 | 8/2009 | Kerns |
| 7,582,102 B2 | 9/2009 | Heinz et al. |
| 7,584,528 B2 | 9/2009 | Hu |
| 7,591,050 B2 | 9/2009 | Hammerslag |
| 7,597,675 B2 | 10/2009 | Ingimundarson et al. |
| 7,600,660 B2 | 10/2009 | Kasper et al. |
| 7,617,573 B2 | 11/2009 | Chen |
| 7,624,517 B2 | 12/2009 | Smith |
| 7,648,404 B1 | 1/2010 | Martin |
| 7,650,705 B2 | 1/2010 | Donnadieu et al. |
| 7,694,354 B2 | 4/2010 | Philpott et al. |
| 7,752,774 B2 | 7/2010 | Ussher |
| 7,757,412 B2 | 7/2010 | Farys |
| 7,774,956 B2 | 8/2010 | Dua et al. |
| D626,322 S | 11/2010 | Servettaz |
| 7,841,106 B2 | 11/2010 | Farys |
| 7,871,334 B2 | 1/2011 | Young et al. |
| 7,877,845 B2 | 2/2011 | Signori |
| 7,900,378 B1 | 3/2011 | Busse |
| 7,908,769 B2 | 3/2011 | Pellegrini |
| 7,947,061 B1 | 5/2011 | Reis |
| 7,950,112 B2 | 5/2011 | Hammerslag et al. |
| 7,954,204 B2 | 6/2011 | Hammerslag et al. |
| 7,963,049 B2 | 6/2011 | Messmer |

(56) References Cited

U.S. PATENT DOCUMENTS

| | | |
|---|---|---|
| 7,992,261 B2 | 8/2011 | Hammerslag et al. |
| D646,790 S | 10/2011 | Castillo et al. |
| 8,056,150 B2 | 11/2011 | Stokes et al. |
| 8,074,379 B2 | 12/2011 | Robinson, Jr. et al. |
| 8,091,182 B2 | 1/2012 | Hammerslag et al. |
| 8,109,015 B2 | 2/2012 | Signori |
| D663,850 S | 7/2012 | Joseph |
| D663,851 S | 7/2012 | Joseph |
| 8,215,033 B2 | 7/2012 | Carboy et al. |
| 8,231,074 B2 | 7/2012 | Hu et al. |
| D665,088 S | 8/2012 | Joseph |
| 8,235,321 B2 | 8/2012 | Chen |
| 8,245,371 B2 | 8/2012 | Chen |
| 8,257,293 B2 | 9/2012 | Ingimundarson et al. |
| 8,266,827 B2 | 9/2012 | Dojan et al. |
| 8,277,401 B2 | 10/2012 | Hammerslag et al. |
| 8,302,329 B2 | 11/2012 | Hurd et al. |
| 8,303,527 B2 | 11/2012 | Joseph |
| 8,308,098 B2 | 11/2012 | Chen |
| 8,353,087 B2 | 1/2013 | Chen |
| 8,353,088 B2 | 1/2013 | Ha |
| D677,045 S | 3/2013 | Voskuil |
| D679,019 S | 3/2013 | Siddle et al. |
| 8,434,200 B2 | 5/2013 | Chen |
| 8,490,299 B2 | 7/2013 | Dua et al. |
| 8,516,662 B2 | 8/2013 | Goodman et al. |
| 8,578,632 B2 | 11/2013 | Bell et al. |
| 8,652,164 B1 | 2/2014 | Aston |
| 8,713,820 B2 | 5/2014 | Kerns et al. |
| 8,795,385 B2 | 8/2014 | Bache |
| 8,984,719 B2 | 3/2015 | Soderberg et al. |
| 9,050,202 B2 | 6/2015 | Bache et al. |
| 9,072,341 B2 | 7/2015 | Jungkind |
| D735,987 S | 8/2015 | Hsu |
| 9,101,181 B2 | 8/2015 | Soderberg et al. |
| 9,125,455 B2 | 9/2015 | Kerns et al. |
| 9,138,030 B2 | 9/2015 | Soderberg et al. |
| 2002/0050076 A1 | 5/2002 | Borsoi et al. |
| 2002/0062579 A1 | 5/2002 | Caeran |
| 2002/0095750 A1 | 7/2002 | Hammerslag |
| 2002/0129518 A1 | 9/2002 | Borsoi ET AL. |
| 2002/0148142 A1 | 10/2002 | Oorei ET AL. |
| 2002/0166260 A1 | 11/2002 | Borsoi |
| 2002/0178548 A1 | 12/2002 | Freed |
| 2003/0079376 A1 | 5/2003 | Oorei ET AL. |
| 2003/0144620 A1 | 7/2003 | Sieller |
| 2003/0150135 A1 | 8/2003 | Liu |
| 2003/0177662 A1 | 9/2003 | Elkington et al. |
| 2003/0204938 A1 | 11/2003 | Hammerslag |
| 2004/0041452 A1 | 3/2004 | Williams |
| 2004/0211039 A1 | 10/2004 | Livingston |
| 2005/0054962 A1 | 3/2005 | Bradshaw |
| 2005/0060912 A1 | 3/2005 | Holzer ET AL. |
| 2005/0081339 A1 | 4/2005 | Sakabayashi |
| 2005/0081403 A1 | 4/2005 | Mathieu ET AL. |
| 2005/0087115 A1 | 4/2005 | Martin |
| 2005/0098673 A1 | 5/2005 | Huang |
| 2005/0102861 A1 | 5/2005 | Martin |
| 2005/0126043 A1 | 6/2005 | Reagan et al. |
| 2005/0172463 A1 | 8/2005 | Rolla |
| 2005/0184186 A1 | 8/2005 | Tsoi et al. |
| 2005/0198866 A1 | 9/2005 | Wiper et al. |
| 2006/0135901 A1 | 6/2006 | Ingimundarson et al. |
| 2006/0156517 A1 | 7/2006 | Hammerslag et al. |
| 2006/0179685 A1 | 8/2006 | Borel et al. |
| 2006/0185193 A1 | 8/2006 | Pellegrini |
| 2006/0287627 A1 | 12/2006 | Johnson |
| 2007/0006489 A1 | 1/2007 | Case, Jr. et al. |
| 2007/0063459 A1 | 3/2007 | Kavarsky |
| 2007/0068040 A1 | 3/2007 | Farys |
| 2007/0084956 A1 | 4/2007 | Chen |
| 2007/0113524 A1 | 5/2007 | Lander |
| 2007/0128959 A1 | 6/2007 | Cooke |
| 2007/0169378 A1 | 7/2007 | Sodeberg et al. |
| 2008/0016717 A1 | 1/2008 | Ruban |
| 2008/0060167 A1 | 3/2008 | Hammerslag et al. |
| 2008/0060168 A1 | 3/2008 | Hammerslag et al. |
| 2008/0066272 A1 | 3/2008 | Hammerslag et al. |
| 2008/0066345 A1 | 3/2008 | Hammerslag et al. |
| 2008/0066346 A1 | 3/2008 | Hammerslag et al. |
| 2008/0068204 A1 | 3/2008 | Carmen et al. |
| 2008/0083135 A1 | 4/2008 | Hammerslag et al. |
| 2008/0092279 A1 | 4/2008 | Chiang |
| 2008/0172848 A1 | 7/2008 | Chen |
| 2008/0196224 A1 | 8/2008 | Hu |
| 2009/0019734 A1 | 1/2009 | Reagan et al. |
| 2009/0071041 A1 | 3/2009 | Hooper |
| 2009/0090029 A1 | 4/2009 | Kishino |
| 2009/0172928 A1 | 7/2009 | Messmer et al. |
| 2009/0184189 A1 | 7/2009 | Soderberg et al. |
| 2009/0272007 A1 | 11/2009 | Beers et al. |
| 2009/0277043 A1 | 11/2009 | Graser et al. |
| 2010/0064547 A1 | 3/2010 | Kaplan |
| 2010/0101061 A1 | 4/2010 | Ha |
| 2010/0139057 A1 | 6/2010 | Soderberg et al. |
| 2010/0154254 A1 | 6/2010 | Fletcher |
| 2010/0175163 A1 | 7/2010 | Litke |
| 2010/0251524 A1 | 10/2010 | Chen |
| 2010/0299959 A1 | 12/2010 | Hammerslag |
| 2010/0319216 A1 | 12/2010 | Grenzke et al. |
| 2011/0000173 A1 | 1/2011 | Lander |
| 2011/0071647 A1 | 3/2011 | Mahon |
| 2011/0162236 A1 | 7/2011 | Voskuil et al. |
| 2011/0167543 A1 | 7/2011 | Kovacevich et al. |
| 2011/0191992 A1 | 8/2011 | Chen |
| 2011/0197362 A1 | 8/2011 | Chella et al. |
| 2011/0225843 A1 | 9/2011 | Kerns et al. |
| 2011/0258876 A1 | 10/2011 | Baker et al. |
| 2011/0266384 A1 | 11/2011 | Goodman et al. |
| 2012/0000091 A1 | 1/2012 | Cotterman et al. |
| 2012/0004587 A1 | 1/2012 | Nickel et al. |
| 2012/0005995 A1 | 1/2012 | Emery |
| 2012/0023717 A1 | 2/2012 | Chen |
| 2012/0101417 A1 | 4/2012 | Joseph |
| 2012/0102783 A1 | 5/2012 | Swigart et al. |
| 2012/0138882 A1 | 6/2012 | Moore et al. |
| 2012/0157902 A1 | 6/2012 | Castillo et al. |
| 2012/0167290 A1 | 7/2012 | Kovacevich et al. |
| 2012/0174437 A1 | 7/2012 | Heard |
| 2012/0228419 A1 | 9/2012 | Chen |
| 2012/0246974 A1 | 10/2012 | Hammerslag et al. |
| 2012/0310273 A1 | 12/2012 | Thorpe |
| 2013/0012856 A1 | 1/2013 | Hammerslag et al. |
| 2013/0014359 A1 | 1/2013 | Chen |
| 2013/0019501 A1 | 1/2013 | Gerber |
| 2013/0025100 A1 | 1/2013 | Ha |
| 2013/0091667 A1 | 4/2013 | Zerfas ET AL. |
| 2013/0091674 A1 | 4/2013 | Chen |
| 2013/0092780 A1 | 4/2013 | Soderberg et al. |
| 2013/0269219 A1 | 10/2013 | Burns et al. |
| 2013/0277485 A1 | 10/2013 | Soderberg et al. |
| 2013/0340283 A1 | 12/2013 | Bell et al. |
| 2013/0345612 A1 | 12/2013 | Bannister et al. |
| 2014/0082963 A1 | 3/2014 | Beers |
| 2014/0094728 A1 | 4/2014 | Soderberg et al. |
| 2014/0117140 A1 | 5/2014 | Goodman et al. |
| 2014/0123440 A1 | 5/2014 | Capra et al. |
| 2014/0123449 A1 | 5/2014 | Soderberg et al. |
| 2014/0208550 A1 | 7/2014 | Neiley |
| 2014/0221889 A1 | 8/2014 | Burns et al. |
| 2014/0257156 A1 | 9/2014 | Capra et al. |
| 2014/0290016 A1 | 10/2014 | Lovett et al. |
| 2014/0359981 A1 | 12/2014 | Cotterman et al. |
| 2015/0007422 A1 | 1/2015 | Cavanagh et al. |
| 2015/0014463 A1 | 1/2015 | Converse et al. |
| 2015/0026936 A1 | 1/2015 | Kerns et al. |
| 2015/0033519 A1 | 2/2015 | Hammerslag et al. |
| 2015/0059206 A1 | 3/2015 | Lovett et al. |
| 2015/0076272 A1 | 3/2015 | Trudel et al. |
| 2015/0089779 A1 | 4/2015 | Lawrence et al. |
| 2015/0089835 A1 | 4/2015 | Hammerslag et al. |
| 2015/0101160 A1 | 4/2015 | Soderberg et al. |
| 2015/0150705 A1 | 6/2015 | Capra et al. |
| 2015/0151070 A1 | 6/2015 | Capra et al. |

(56) References Cited

U.S. PATENT DOCUMENTS

| | | |
|---|---|---|
| 2015/0190262 A1 | 7/2015 | Capra et al. |
| 2015/0223608 A1 | 8/2015 | Capra et al. |
| 2015/0237962 A1 | 8/2015 | Soderberg et al. |
| 2015/0335458 A1 | 11/2015 | Romo |

FOREIGN PATENT DOCUMENTS

| | | |
|---|---|---|
| AT | 361808 | 4/1981 |
| CA | 2114387 | 1/1994 |
| CA | 2112789 | 8/1994 |
| CA | 2114387 | 8/1994 |
| CH | 41765 | 9/1907 |
| CH | 111341 | 11/1925 |
| CH | 199766 | 9/1938 |
| CH | 199766 | 11/1938 |
| CH | 204 834 A | 5/1939 |
| CH | 204 834 A | 8/1939 |
| CH | 523 669 | 7/1972 |
| CH | 562 015 | 5/1975 |
| CH | 577 282 | 7/1976 |
| CH | 612 076 | 7/1979 |
| CH | 537 164 | 7/1981 |
| CH | 624 001 | 7/1981 |
| CH | 471 553 | 12/1984 |
| CN | 2613167 | 4/2004 |
| CN | 201015448 | 2/2008 |
| DE | 555211 | 7/1932 |
| DE | 641976 | 2/1937 |
| DE | 1 661 668 | 8/1953 |
| DE | 7043154.8 | 11/1970 |
| DE | 1 785 220 | 5/1971 |
| DE | 2 062 795 | 6/1972 |
| DE | 23 41 658 | 3/1974 |
| DE | 24 14 439 | 10/1975 |
| DE | 29 00 077 A1 | 7/1980 |
| DE | 2914280 A1 | 10/1980 |
| DE | 31 01 952 A1 | 9/1982 |
| DE | 36 26 837 | 2/1988 |
| DE | 38 13 470 | 11/1989 |
| DE | 3822113 C2 | 1/1990 |
| DE | 9413147 | 6/1994 |
| DE | 43 02 401 A1 | 8/1994 |
| DE | 43 05 671 A1 | 9/1994 |
| DE | 9308037 | 10/1994 |
| DE | 43 26 049 A1 | 2/1995 |
| DE | 9315776 | 2/1995 |
| DE | 29503552.8 | 4/1995 |
| DE | 196 24 553 | 1/1998 |
| DE | 19945045 A1 | 3/2001 |
| DE | 201 16 755 U1 | 1/2002 |
| DE | 20 2010 000 354 U1 | 6/2010 |
| DE | 11 2013 005 273 T5 | 9/2015 |
| EP | 0 056 953 81 | 6/1969 |
| EP | 0 081 042 81 | 7/1972 |
| EP | 0 056 953 | 8/1982 |
| EP | 0 099 504 | 2/1984 |
| EP | 0 123 050 | 2/1984 |
| EP | 0 123 050 | 10/1984 |
| EP | 0 155 596 | 9/1985 |
| EP | 0 201 051 | 11/1986 |
| EP | 0 099 504 | 1/1987 |
| EP | 0 255 869 | 7/1987 |
| EP | 0 155 596 | 1/1988 |
| EP | 0 255 869 | 2/1988 |
| EP | 0 393 380 | 3/1990 |
| EP | 0 393 380 | 10/1990 |
| EP | 0 474 708 | 9/1993 |
| EP | 0 589 232 A1 | 3/1994 |
| EP | 0 589 233 A1 | 3/1994 |
| EP | 0 614 625 A1 | 9/1994 |
| EP | 0 651 954 A1 | 5/1995 |
| EP | 0 679 346 | 11/1995 |
| EP | 0 693 260 B1 | 1/1996 |
| EP | 0 717 942 | 6/1996 |
| EP | 0 858 619 | 8/1996 |
| EP | 0 734 662 A1 | 10/1996 |
| EP | 0 848 917 | 6/1998 |
| EP | 0 858 621 | 8/1998 |
| EP | 0 923 965 | 6/1999 |
| EP | 0 937 467 | 8/1999 |
| EP | 0 848 917 81 | 4/2000 |
| EP | 1163860 | 12/2001 |
| EP | 1 219 195 | 7/2002 |
| EP | 1 236 412 | 9/2002 |
| EP | 2298107 B1 | 3/2011 |
| EP | 2359708 | 8/2011 |
| FR | 1 349 832 | 3/1963 |
| FR | 1 404 799 | 7/1964 |
| FR | 1 404 799 | 7/1965 |
| FR | 2 019 991 A | 7/1970 |
| FR | 2 108 428 | 9/1971 |
| FR | 2 175 684 | 3/1972 |
| FR | 2.108.429 | 5/1972 |
| FR | 2 565 795 | 6/1984 |
| FR | 2 598 292 A1 | 11/1987 |
| FR | 2 726 440 A1 | 5/1996 |
| FR | 2 770 379 A1 | 5/1999 |
| FR | 2 814 919 A1 | 4/2002 |
| GB | 189911673 | 7/1899 |
| GB | 216400 | 5/1924 |
| GB | 2 449 722 A | 12/2008 |
| IT | 1220811 | 6/1990 |
| IT | PD 2003 A 000197 | 4/2003 |
| IT | PD 2003 A 000198 | 3/2005 |
| JP | 49-28618 | 3/1974 |
| JP | 51-2776 | 1/1976 |
| JP | 51-121375 | 10/1976 |
| JP | 51-131978 | 10/1976 |
| JP | 53-124987 | 3/1977 |
| JP | 54-108125 | 2/1978 |
| JP | 62-57346 | 4/1987 |
| JP | 63-80736 | 5/1988 |
| JP | H02-236025 | 9/1990 |
| JP | 7-000208 | 6/1995 |
| JP | 6-284906 | 2/1996 |
| JP | 3031760 | 9/1996 |
| JP | 3030988 | 11/1996 |
| JP | 8308608 | 11/1996 |
| JP | 3031760 | 12/1996 |
| JP | 10-199366 | 7/1998 |
| JP | 2001-197905 | 7/2001 |
| JP | 2004-016732 | 1/2004 |
| JP | 2004-041666 | 2/2004 |
| JP | 2009-504210 | 2/2009 |
| KR | 20-0367882 | 11/2004 |
| KR | 20-0400568 | 8/2005 |
| KR | 10-0598627 | 7/2006 |
| KR | 10-0953398 | 4/2010 |
| KR | 10-1025134 B1 | 3/2011 |
| KR | 10-1028468 | 4/2011 |
| KR | 10-1053551 | 7/2011 |
| WO | WO 94/27456 | 12/1994 |
| WO | WO 95/03720 | 2/1995 |
| WO | WO 1995/03720 | 2/1995 |
| WO | WO 95/11602 | 5/1995 |
| WO | WO 98/33408 | 8/1998 |
| WO | WO 98/37782 | 9/1998 |
| WO | WO 99/09850 | 3/1999 |
| WO | WO 99/15043 | 4/1999 |
| WO | WO 99/43231 | 9/1999 |
| WO | WO00/53045 | 9/2000 |
| WO | WO 00/53045 | 9/2000 |
| WO | WO 2000/76337 A1 | 12/2000 |
| WO | WO 01/08525 | 2/2001 |
| WO | WO 01/15559 | 3/2001 |
| WO | WO 02/051511 | 7/2002 |
| WO | WO 2004/093569 | 11/2004 |
| WO | WO 2005/013748 A1 | 2/2005 |
| WO | WO/2007/016983 | 2/2007 |
| WO | WO 2008/015214 | 2/2008 |
| WO | WO/2008/033963 | 3/2008 |
| WO | WO/2009/134858 | 11/2009 |
| WO | WO 2010/059989 A2 | 5/2010 |
| WO | WO 2012/165803 A2 | 12/2012 |

(56) References Cited

FOREIGN PATENT DOCUMENTS

| WO | WO/2015/035885 | 3/2015 |
|---|---|---|
| WO | WO 2015/179332 A1 | 11/2015 |
| WO | WO 2015/181928 A1 | 12/2015 |

OTHER PUBLICATIONS

U.S. Appl. No. 09/956,601, filed Sep. 18, 2001, Hammerslag.
ASOLO® Boot Brochure Catalog upon information and belief date is as early as Aug. 22, 1997, 12 pages.
La Sportiva, A Technical Lightweight Double Boot for Cold Environments, 1 page. Accessed on May 27, 2015. Retrieved from http://www.sportiva.com/products/footwear/mountain/spantik.
"Strength of materials used to make my Safety Harnesses," Elaine, Inc. Jul. 9, 2012. Retrieved from <https://web.archive.org/web/20120709002720/http://www.childharness.ca/strength_data.html> on Mar. 17, 2014, 2 pages.
International Search Report and Written Opinion for PCT/US2013/032326 dated Jun. 14, 2013, 27 pages.
International Preliminary Report on Patentability for PCT/US2013/032326 dated Sep. 16, 2014, 6 pages.
International Search Report and Written Opinion for PCT/US2013/057637 dated Apr. 7, 2014, 34 pages.
International Preliminary Report on Patentability for PCT/US2013/057637 dated Mar. 3, 2015, 9 pages.
International Search Report and Written Opinion for PCT/US2013/068342 dated Apr. 7, 2014, 29 pages.
International Preliminary Report on Patentability for PCT/US2013/068342 dated May 5, 2015, 9 pages.
International Search Report and Written Opinion for PCT/US2014/014952 dated Apr. 25, 2014, 17 pages.
International Preliminary Report on Patentability for PCT/US2014/014952 dated Aug. 11, 2015, 9 pages.
International Search Report and Written Opinion for PCT/US2014/066212 dated Apr. 22, 2015, 16 pages.
International Search Report and Written Opinion for PCT/US2014/032574 dated Oct. 31, 2014, 19 pages.
International Search Report and Written Opinion for PCT/US2014/045291 dated Nov. 6, 2014, 12 pages.
International Search Report and Written Opinion for PCT/US2014/013458 dated May 19, 2014, 12 pages.
International Preliminary Report on Patentability for PCT/US2014/013458 dated Jul. 28, 2015, 7 pages.
International Search Report and Written Opinion for PCT/US2013/068814 dated Jun. 9, 2014, 18 pages.
International Preliminary Report on Patentability for PCT/US2013/068814 dated May 12, 2015, 12 pages.
Notice of Reasons for Rejection from the Japanese Patent Office dated Feb. 26, 2015 for design application No. 2014-015570, 4 pages.
Receipt of Certificate of Design Registration No. 1529678 from the Japanese Patent Office for design application No. 2014-015570 dated Jun. 26, 2015, 1 page.
International Search Report and Written Opinion for PCT/US2014/055710 dated Jul. 6, 2015, 19 pages.
International Search Report and Written Opinion for PCT/US2014/054420 dated Jul. 6, 2015, 21 pages.
The Preliminary Rejections from the Korean Intellectual Property Office for Application No. 30-201434959 dated Aug. 7, 2015, is not translated into English. The document requests a renaming of the application to be in accordance with Korean patent law, 5 pages total.
The Preliminary Rejections from the Korean Intellectual Property Office for Application No. 30-201434959 dated Apr. 7, 2015, is not translated into English. The document requests a revision of the drawings to be in accordance with Korean patent law, 6 pages total.
Certificate of Design Registration No. 30-809409 dated Aug. 3, 2015 from the Korean Intellectual Property Office for Appln No. 30-2015-11475, 2 pages.
Certificate of Design Registration No. 30-809410 dated Aug. 3, 2015 from the Korean Intellectual Property Office for Appln No. 30-2015-11476, 2 pages.
European Search Report for EP 14168875 dated Oct. 29, 2014, 9 pages.
International Search Report and Written Opinion for PCT/US2014/020894 dated Jun. 20, 2014, 12 pages.
International Preliminary Report on Patentability for PCT/US2014/020894 dated Sep. 8, 2015, 7 pages.
International Search Report and Written Opinion for PCT/US2014/041144 dated Dec. 10, 2014, 13 pages.
International Preliminary Report on Patentability for PCT/US2014/032574 dated Oct. 6, 2015, 12 pages.
International Search Report and Written Opinion for PCT/US2014/046238 dated Nov. 21, 2014, 17 pages.
Office Action dated Oct. 8, 2015 from the German Patent and Trademark Office for Appln No. 402015100191.2, regarding the title of the invention, 2 pages.
Anonymous, "Shore durometer," Wikipedia, the free encyclopedia, Mar. 10, 2012, XP002747470, Retrieved from the Internet: URL: https://en.wikipedia.org/w/index.php?title=Shore_durometer &oldid=481128180 [retrieved on Oct. 20, 2015] * shore A, shore D, durometer, polymer, rubber, gel; the whole document *, 6 pages.
Notice of Reasons for Rejection from the Japanese Patent Office dated Oct. 5, 2015 for design application No. 2015-004923, 4 pages.
"Save Tourniquet," 3 pages. Copyright 2015. Accessed on Dec. 11, 2015. Retrieved from http://www.savetourniquet.com/.
Office Action for EP 14 810 068.8 dated Jun. 19, 2017, 3 pages.

\* cited by examiner

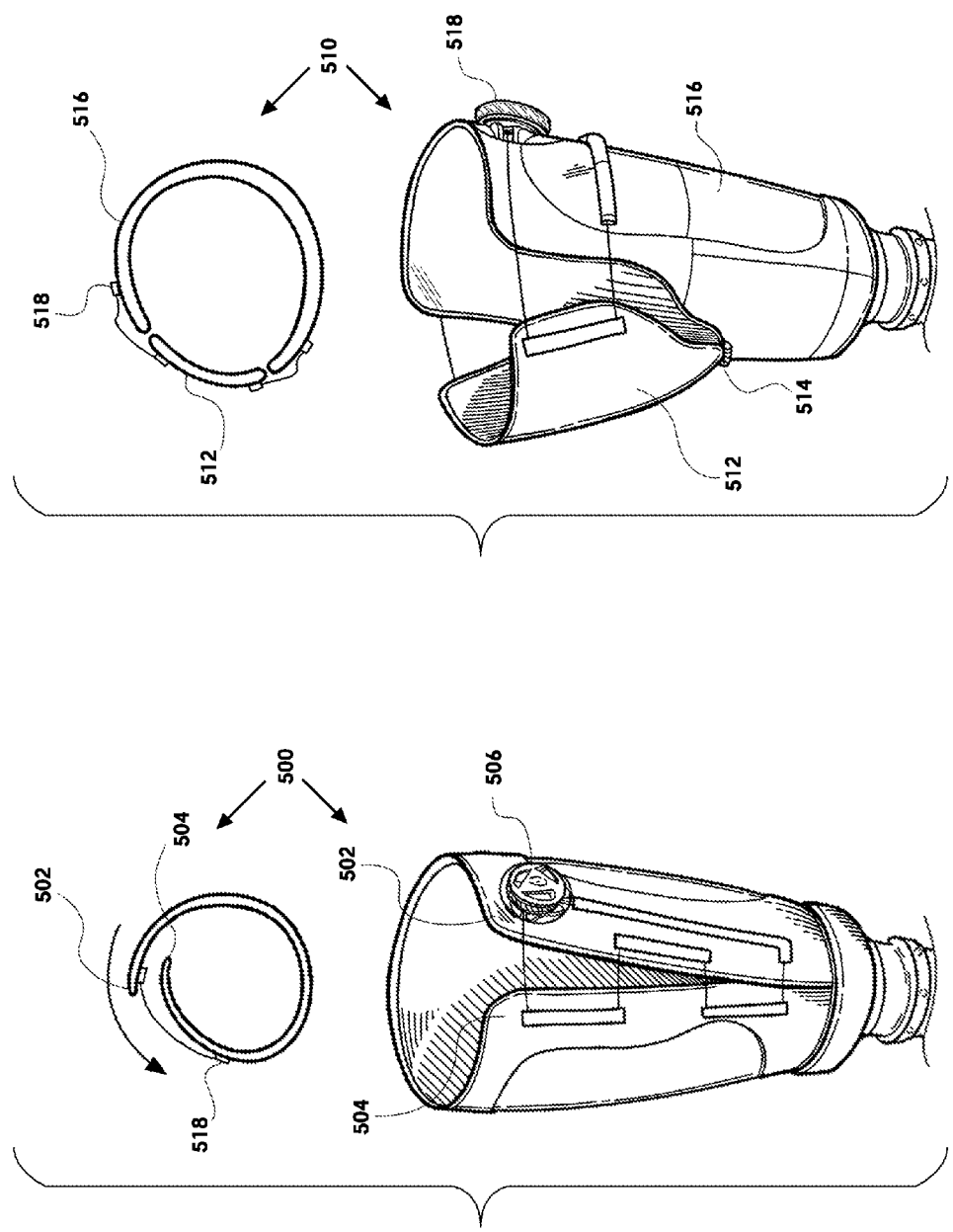

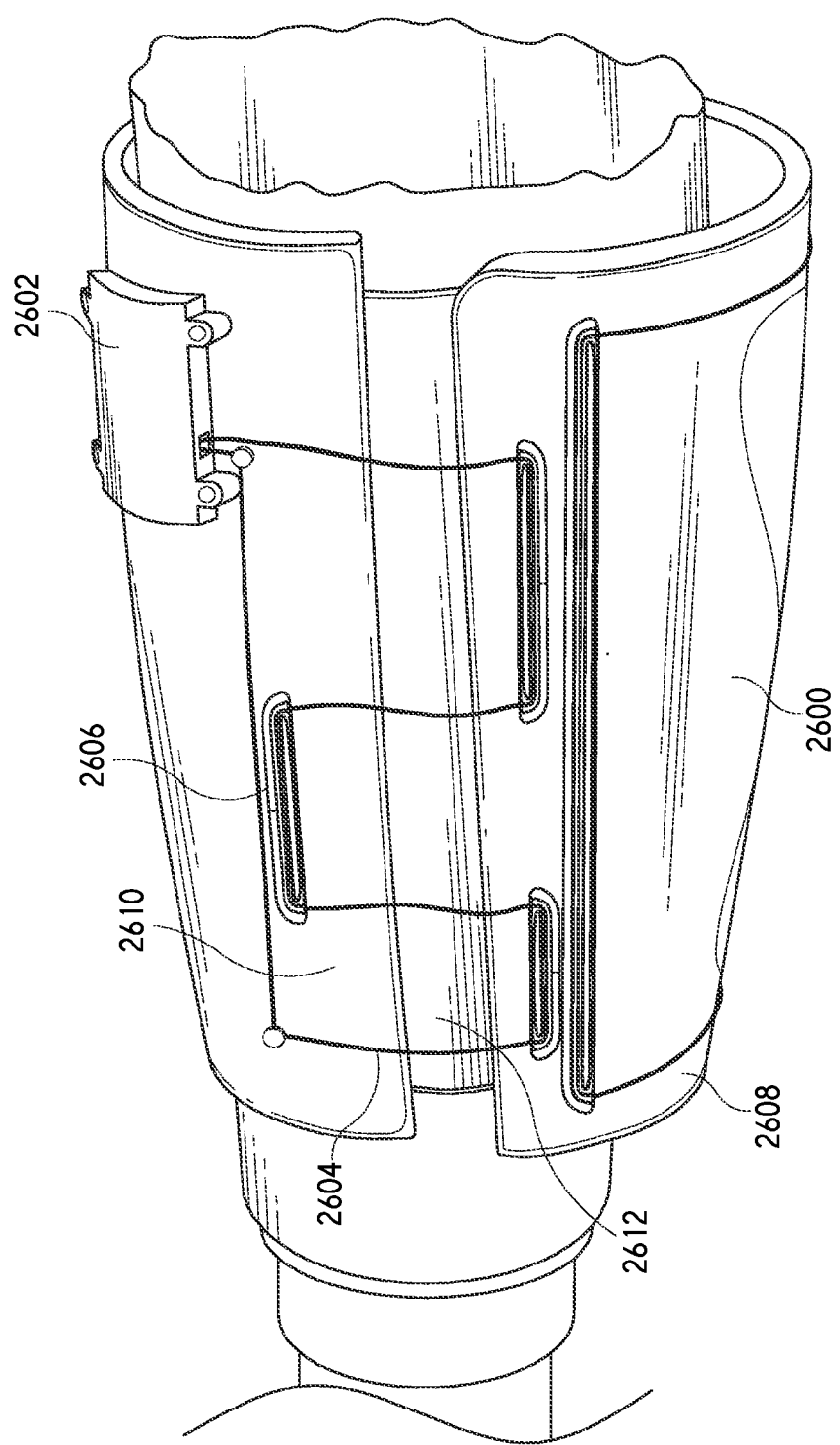

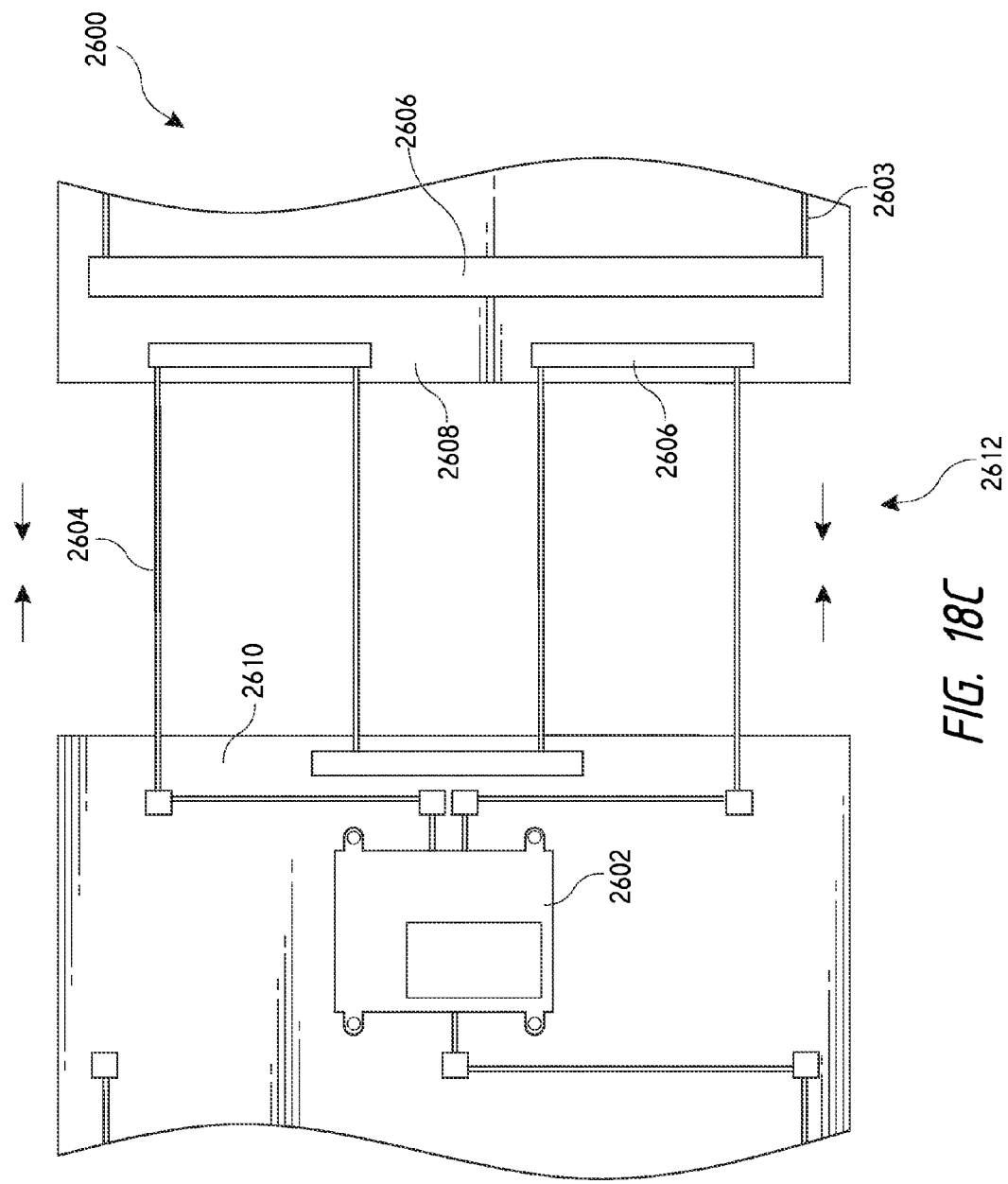

METHODS AND DEVICES FOR PROVIDING AUTOMATIC CLOSURE OF PROSTHETICS AND ORTHOTICS

CROSS-REFERENCES TO RELATED APPLICATIONS

This application claims the benefit of U.S. Provisional Application No. 61/905,753, filed on Nov. 18, 2013, and titled "Methods and Devices for Providing Automatic Closure of Prosthetics and Orthotics," the entire disclosure of which is incorporated by reference herein for all purposes.

BACKGROUND OF THE INVENTION

The present embodiments relate generally to medical braces, devices, and other articles including tensioning systems.

Medical braces are typically fit about a limb and tightened to secure the brace about the limb. Conventional tightening for braces often require a user to use both hands in securing the brace about a limb. For example, Velcro® straps and buckles often require the user to grasp the strap or the body of the brace to hold the brace or strap in position while the strap is secured to the brace. Properly fitting such braces may be difficult and/or challenging for patients, especially when the patient is dexterity challenged or the brace is being fit to the arm or hand.

BRIEF SUMMARY OF THE INVENTION

The present invention generally provides improved systems for closing and tightening an article, such as a brace about a user's limb. According to one aspect, a method for automatically opening and closing a brace about a limb is provided. The method involves a brace having: a tensioning device having a first mode of operation and a second mode of operation and a first tension member that is coupled with the tensioning device and tensionable thereby to effect tightening of the brace about the limb. The method includes operating the tensioning device in the first mode of operation and operating the tensioning device in the second mode of operation. Operating the tensioning device in the first mode of operation effects tensioning of the first tension member to close and tighten the brace about the limb and operating the tensioning device in the second mode of operation effects loosening of the first tension member and effects opening of the brace from about the limb. In some embodiments the brace also includes a second tension member that is coupled with the tensioning device and is tensionable thereby to effect opening of the brace from about the limb. In such embodiments, operating the tensioning device in the second mode of operation tensions the second tension member while loosening the first tension member. The second tension member may be coupled with the brace so that tensioning of the second tension member loosens and opens the brace from about the limb.

The first tension member may be routed along a first path about the brace that is configured to close and tighten the brace upon tensioning of the first tension member and the second tension member may be routed along a second path about the brace that is configured to open and loosen the brace upon tensioning of the second tension member. The first path and the second path may be configured so that an amount of displacement of the second tension member about the second path is proportional or equivalent to an amount of displacement of the first tension member about the first path.

In some embodiments, the tensioning device may be a reel based closure system having a knob that is rotatable in a first direction and a second direction. In such embodiments, rotation of the knob in the first direction corresponds to the first mode of operation of the tensioning device and rotation of the knob in the second direction corresponds to the second mode of operation of the tensioning device. In other embodiments, the tensioning device may be a motorized device having an internal mechanism that effects tensioning of the first tension member and simultaneous loosening of the second tension member in the first mode of operation and that effects tensioning of the second tension member and simultaneous loosening of the first tension member in the second mode of operation. In such embodiments, the brace may also include a control unit that is communicatively coupled with the motorized tensioning device and the method may further include: receiving a first input at the control unit; communicating a first instruction from the control unit to the motorized tensioning device; in response to the first instruction, operating the motorized tensioning device in the first mode of operation to tension the first tension member and close and tighten the brace about the limb; receiving a second input via the control unit; communicating a second instruction from the control unit to the motorized tensioning device; and in response to the second instruction, operating the motorized tensioning device in the second mode of operation to tension the second tension member and open and loosen the brace from about the limb.

According to another aspect, a brace is provided. The brace includes: a tensioning device having a first mode of operation and a second mode of operation, a first tension member that is coupled with the tensioning device and tensionable thereby to effect tightening of the brace about the limb, and a second tension member that is coupled with the tensioning device and tensionable thereby to effect opening of the brace from about the limb. The tensioning device is configured so that: operating the tensioning device in the first mode of operation effects tensioning of the first tension member to close and tighten the brace about the limb and operating the tensioning device in the second mode of operation effects tensioning of the second tension member to loosen and open the brace from about the limb.

In some embodiments, the tensioning device may be configured so that: operating the tensioning device in the first mode of operation effects loosening of the second tension member while simultaneously tensioning the first tension member and operating the tensioning device in the second mode of operation effects loosening of the first tension member while simultaneously tensioning the second tension member. The first tension member may be routed about the brace along a first path that is configured to close and tighten the brace upon tensioning of the first tension member and the second tension member may be routed about the brace along a second path that is configured to open and loosen the brace upon tensioning of the second tension member. In such embodiments, the first path and the second path may be configured so that an amount of displacement of the second tension member about the second path is proportional or equivalent to an amount of displacement of the first tension member about the first path.

In some embodiments, the tensioning device is a reel based closure system having a knob that is rotatable in a first direction and a second direction. In such embodiments, rotation of the knob in the first direction corresponds to the first mode of operation and rotation of the knob in the second direction corresponds to the second mode of operation. In other embodiments, the tensioning device is a motorized device having an internal mechanism that effects tensioning of the first tension member and simultaneous loosening of the second tension member in the first mode of operation and that effects tensioning of the second tension member and simultaneous loosening of the first tension member in the second mode of operation. In such embodiments, the brace may further include a control unit that is communicatively coupled with the motorized tensioning device. The control unit may be configured to: receive a first input; communicate a first instruction to the motorized tensioning device to effect operation of the motorized tensioning device in the first mode of operation; receive a second input; and communicate a second instruction to the motorized tensioning device to effect operation of the motorized tensioning device in the second mode of operation.

According to another aspect, a lacing system for opening and closing an article is provided. The lacing system includes: a tensioning device having a first mode of operation and a second mode of operation, a first tension member that is coupled with the tensioning device and tensionable thereby, and a second tension member that is coupled with the tensioning device and tensionable thereby. The tensioning device is configured to: effect tensioning of the first tension member to close and tighten the article upon operation of the tensioning device in the first mode of operation and effect tensioning of the second tension member to loosen and open the article upon operation of the tensioning device in the second mode of operation.

The first tension member may be routed about the article along a first path that is configured to close and tighten the article upon tensioning of the first tension member and the second tension member may be routed about the article along a second path that is configured to open and loosen the article upon tensioning of the second tension member. In such embodiments, the first path and the second path are configured so that an amount of displacement of the second tension member about the second path is proportional or equivalent to an amount of displacement of the first tension member about the first path.

In some embodiments, the tensioning device is a reel based closure system having a knob that is rotatable in a first direction and a second direction. In such embodiments, rotation of the knob in the first direction corresponds to the first mode of operation and rotation of the knob in the second direction corresponds to the second mode of operation. In other embodiments, the tensioning device is a motorized device having an internal mechanism that effects tensioning of the first tension member and simultaneous loosening of the second tension member in the first mode of operation and that effects tensioning of the second tension member and simultaneous loosening of the first tension member in the second mode of operation. In such embodiments, the lacing system further includes a control unit that is communicatively coupled with the motorized tensioning device. The control unit may be configured to: receive a first input, communicate a first instruction to the motorized tensioning device to effect operation of the motorized tensioning device in the first mode of operation, receive a second input, and communicate a second instruction to the motorized tensioning device to effect operation of the motorized tensioning device in the second mode of operation.

According to another aspect, a lacing system is provided. The lacing system includes: a tensioning device, a tensioning mechanism that is operated via the tensioning device, and a plurality of tension members that are coupled with the tensioning mechanism and tensionable thereby. The plurality of tension members are arranged longitudinally about an opening of an article and configured to narrow a gap of the opening upon tensioning of the plurality of tension members in order to tighten the article. Operation of the tensioning mechanism effects a simultaneous and repeatable tensioning of each tension member of the plurality of tension members to achieve a relatively uniform tightening of the article.

In some embodiments, at least one tension member of the plurality of tension members is adjustably coupled with the article so that adjustment of the tension member effects tensioning of the respective tension member upon operation of the tensioning mechanism. The at least one tension member of the plurality of tension members may be adjustably coupled with the article via: an adjustable terminating end, a teeter mechanism, a lock mechanism, and/or a buckle. In some embodiments, the article is a brace.

In some embodiments, the tensioning mechanism includes an elongate member that is moveable longitudinally relative to the opening of the article upon operation of the tensioning device. In such embodiments, each tension member may be positioned longitudinally along the elongate member. A proximal end of the elongate member may be coupled with a lace that is tensioned via operation of the tensioning device to move the elongate member longitudinally relative to the opening of the article.

In another embodiment, the tensioning mechanism includes an elongate member that is positioned longitudinally along the opening of the article. In such embodiments, each tension member is positioned longitudinally along the elongate member and the elongate member is configured to rotate about a longitudinal axis upon operation of the tensioning device to effect winding of the plurality of tension members about the elongate member. At least one of the plurality of tension members may be a strap.

In another embodiment, the tensioning mechanism may be further configured to equalize the tension in each tension member of the plurality of tension members during tensioning of the plurality of tension members. The tensioning mechanism may also be configured to equalize the tension in each tension member of the plurality of tension members subsequent to tensioning of the plurality of tension members. In such embodiments, a lace may be coupled with the tensioning mechanism and the tensioning device. The lace may be tensionable via operation of the tensioning device to effect movement of the tensioning mechanism and thereby tighten the article. The tensioning mechanism may be configured to pivot to equalize the tension in each tension member. The tensioning mechanism may include a first tension equalizer and a second tension equalizer. The first tension equalizer may effect equalizing the tension between a first and second tension member and the second tension equalizer may effect equalizing the tension between the a third tension member and the first and second tension members. In such embodiments, the first tension equalizer may be a pulley about which the first and second tension members are slidingly positioned and the second tension equalizer may be a pivotable coupling between the third tension member and the first and second tension members.

According to another aspect, a method of configuring an article with a lacing system is provided. The method includes providing a lacing system that includes: a tensioning device, a tensioning mechanism that is operated via the tensioning device, and a plurality of tension members that are coupled with the tensioning mechanism and tensionable thereby. The method also includes coupling the tensioning device with an article and coupling each tension member of the plurality of tension members with the article so that the plurality of tension members are arranged longitudinally about an opening of an article and configured to narrow a gap of the opening upon tensioning of the plurality of tension members in order to tighten the article. The tensioning mechanism is configured so that operation of the tensioning mechanism effects a simultaneous and repeatable tensioning of each tension member of the plurality of tension members to achieve a relatively uniform tightening of the article.

In some embodiments, at least one tension member is adjustably coupled with the article so that adjustment of the tension member effects tensioning of the respective tension member upon operation of the tensioning mechanism. The at least one tension member may be adjustably coupled with the article via: an adjustable terminating end, a teeter mechanism, a lock mechanism, and/or a buckle. In some embodiments, the article is a brace.

In one embodiment, the tensioning mechanism is an elongate member that is moveable longitudinally relative to the opening of the article upon operation of the tensioning device. In this embodiment, the method further includes coupling each tension member longitudinally along the elongate member. In another embodiment, the tensioning mechanism is an elongate member that is coupled with the article longitudinally along the opening of the article. In this embodiment, each tension member is coupled longitudinally along the elongate member and the elongate member is configured to rotate about a longitudinal axis upon operation of the tensioning device to effect winding of the plurality of tension members about the elongate member. In another embodiment, the tensioning mechanism is further configured to equalize the tension in each tension member of the plurality of tension members during tensioning of the plurality of tension members. In this embodiment, the tensioning mechanism may be further configured to equalize the tension in each tension member of the plurality of tension members subsequent to tensioning of the plurality of tension members. In this embodiment, the tensioning mechanism may include a first means of tension equalization and a second means of tension equalization. The first means of tension equalization may effect equalizing the tension between a first and second tension member and the second means of tension equalization may effect equalizing the tension between the a third tension member and the first and second tension members.

According to another aspect, a lacing system for tightening an article about a limb is provided. The lacing system includes: a tensioning device that is coupleable with the article, a tension member that is coupled with the tensioning device and tensionable thereby, and a pressure member that is coupleable with the article and operable with the tension member so as to be moveable between a first position and a second position relative to the article upon tensioning of the tension member. When the pressure member is in the first position, an opening of the article comprises a surface area. When the pressure member is in the second position, the pressure member is displaced into the opening of the article to reduce the surface area and thereby apply inward pressure to the limb.

In one embodiment, the pressure member includes opposing ends that are coupled with the article and a middle portion that is not coupled with the article. In this embodiment, tensioning of the tension member causes the middle portion of the pressure member to flex inward into the opening of the article. In this embodiment, the pressure member may be configured so that an amount of flexing of the middle portion of the pressure member corresponds with an amount of tension induced in the tension member. This configuration may enable infinitesimal amounts of pressure to be applied to the limb. In some instances, one of the opposing ends of the pressure member may be slidably coupled with the article and one of the opposing ends may be fixedly coupled with the article so that upon tensioning of the tension member, the slidable opposing end slides toward the fixed opposing end.

In another embodiment, the pressure member may include a first member and a second member that is moveably coupled with the first member. Tensioning of the tension member may cause the second member to move relative to the first member and inward into the opening of the article. The pressure member may be configured so that an amount of movement of the second member relative to the first member and inward into the opening of the article corresponds with an amount of tension induced in the tension member. This configuration may enable infinitesimal amounts of pressure to be applied to the limb. In this embodiment, the pressure member may also include a third member that couples the second member with the first member and effects movement of the second member inward into the opening of the article upon tensioning of the tension member. The third member may be a compliant mechanism or may pivotably couple the second member with the first member, such as via a hinge component.

In another embodiment, the pressure member includes a first member and a second member with the second member slidably coupled with the first member so as to be slidable between a proximal end and a distal end of the first member. Sliding of the second member from the proximal end to the distal end of the first member may cause the first member to displace inward into the opening of the article. The first member may have a tapered configuration between the proximal and distal ends so that sliding of the second member along the tapered configuration of the first member effects an increased amount of displacement of the first member inward into the opening of the article. This configuration may enable infinitesimal amounts of pressure to be applied to the limb.

According to another aspect, a lacing system for tightening an article about a limb is provided. The lacing system includes: a tensioning device that is coupleable with the article, a tension member that is coupled with the tensioning device and tensionable thereby, and a pressure member that is coupleable with the article and positionable so that an inner surface of the pressure member faces radially inward relative to an opening of the article. The pressure member is operable with the tension member so as to displace radially into the opening of the article upon tensioning of the tension member to reduce the opening of the article and thereby apply pressure to the limb.

According to another aspect, a method of configuring an article with a lacing system is provided. The method include providing a lacing system that includes: a tensioning device, a tension member that is coupled with the tensioning device and tensionable thereby, and a pressure member. The method also includes coupling the tensioning device with the article and coupling the pressure member with the article so that an inner surface of the pressure member faces radially inward relative to an opening of the article. The pressure member is operable with the tension member so as to displace radially into the opening of the article upon tensioning of the tension member to reduce the opening of the article and thereby apply pressure to the limb.

In one embodiment, coupling the pressure member with the article includes coupling opposing ends of the pressure member with the article while a middle portion of the pressure member remains uncoupled from the article so that tensioning of the tension member causes the middle portion of the pressure member to flex radially inward into the opening of the article. In this embodiment, the method may further include slidably coupling one of the opposing ends of the pressure member with the article and fixedly coupling the other opposing end with the article so that, upon tensioning of the tension member, the slidable opposing end slides toward the fixed opposing end.

In another embodiment, the pressure member may include a first member and a second member that is moveably coupled with the first member. In this embodiment, tensioning of the tension member may cause the second member to move relative to the first member and radially into the opening of the article. In this embodiment, the pressure member may further include a third member that couples the second member with the first member and effects movement of the second member radially into the opening of the article upon tensioning of the tension member.

In another embodiment, coupling the pressure member with the article may include slidably coupling a second member with a first member so that the second member is slidable between a proximal end and a distal end of the first member. In this embodiment, sliding of the second member from the proximal end to the distal end of the first member may cause the first member to displace radially into the opening of the article. In this embodiment, the first member may have a tapered configuration between the proximal and distal ends so that sliding of the second member along the tapered configuration of the first member effects an increased amount of displacement of the first member radially into the opening of the article.

BRIEF DESCRIPTION OF THE DRAWINGS

The present invention is described in conjunction with the appended figures:

FIGS. 5A-D illustrate a tightening system coupled with prosthetic shells of various shape.

FIGS. 18A-C illustrate a tensioning system that may be used to open and close an article, such as a prosthetic device.

Figure 1:
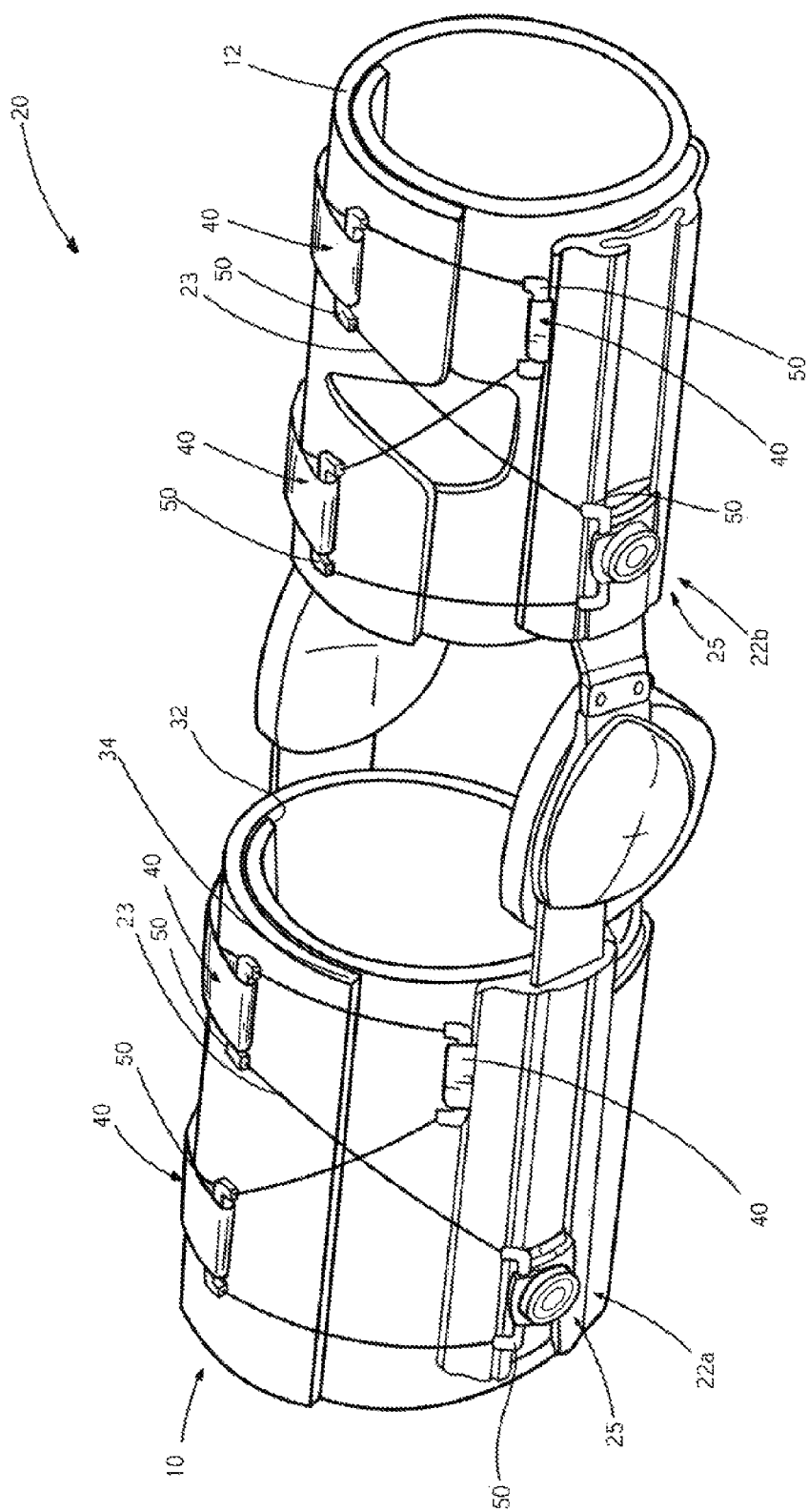
FIGS. 1-3 illustrate a general embodiment of a tightening system that utilizes a reel based tensioning system and components thereof.

In the appended figures, similar components and/or features may have the same numerical reference label. Further, various components of the same type may be distinguished by following the reference label by a letter that distinguishes among the similar components and/or features. If only the first numerical reference label is used in the specification, the description is applicable to any one of the similar components and/or features having the same first numerical reference label irrespective of the letter suffix.

DETAILED DESCRIPTION OF THE INVENTION

Embodiments described herein provide various tightening systems and/or closure devices that may be used with various articles includes braces, footwear, hats, gloves, prosthetics, orthotics, or other apparel or devices to open and close the article, such as to allow a user to don and doff the article. In a specific embodiment, the article may be a prosthetic or orthotic device that is worn by the user to support and/or provide a desired therapy to a limb. For convenience in describing the embodiments herein, the tightening systems and/or closure devices will be mainly described as being used with prosthetic devices, although it should be realized that the embodiments are equally applicable to orthotic devices and/or other article.

As described herein, the tightening system means any system, mechanism, or component thereof that is designed to tighten a prosthetic device about an individual's limb. The closure device may be any component of the tightening system that is used to tighten the prosthetic device about the limb. Conventional tightening systems often include various straps (e.g., Velcro straps), vacuum or suction systems, lace, socks or liners for the limb, and the like. For ease in describing the embodiments herein, the tightening system/closure devices will be referred to generally as "tightening systems" or various components thereof, such as lace or tension members, guides for lace or tension members, reel based closure devices or assemblies, and the like.

In some embodiments, conventional tightening systems often include predetermined component locations (e.g., lace or strap locations) that provide relatively standard distributions of pressure regardless of the unique characteristics of the individual (e.g., limb size, limb configuration, and the like). The embodiments described herein provide adjustable and/or customizable tightening system configurations that enhance the closure and/or fit for the prosthetic to meet a variety of user needs. In some embodiments prosthetic closure customization is achieved by integrating removable guides into arrays of guide receiving components, which allows a user to insert and remove guides to create a unique prosthetic tightening configuration that provides customized support and conforms to the user's unique limb characteristics and/or other needs. For example, the embodiments described herein allow users and/or doctors to alter the configuration of the tightening system so as to create a customized prosthetic fit and/or to avoid tensioning or applying pressure to a certain area of the body that may be pressure sensitive. In other embodiments, the customized fit may be used to create void areas in order to "off-load" or reduce the pressure exerted on a certain area, such as, for example, to reduce pressure in a diabetic walker and the like.

In other embodiments, easy adjustment of the prosthetic may be made possible without the need to remove the prosthetic from the user's limb. In some embodiments, the tightening systems described herein can be incorporated into an off-the-shelf prosthetic to add an additional element of adjustability and/or can be implemented with a custom-made prosthetic device.

The tightening systems described herein, or components thereof, offer solutions to many problems associated with conventional tightening systems for prosthetics. In many of the embodiments described herein, tightening systems may be easily adjusted to create custom pressure zones, allowing for customization of fit for comfort and/or therapeutic purposes. Further, the tightening systems described herein can increase the ease and efficiency associated with adjusting a prosthetic device for a proper fit.

As described in greater detail below, in some embodiments, the tightening system may include a reel based closure device or system, which may include a reel assembly, lace, and one or more lace guides that tighten the prosthetic device via tensioning of the lace via the reel assembly. The use of a reel based tensioning system may significantly increase the customization of the prosthetic device by allowing the prosthetic to be more tailored or custom fit to a patient. For example, the lace of the system may be easily wound around custom placed/positioned, custom designed, and/or custom fit lace guides that are coupled with the prosthetic device in order to create a customized and/or unique lace path about the medical brace. The lace path may be tailored or customized to the patient to provide increased and/or decreased zonal tensioning and/or pressure about the patient's limb that promotes optimal fit and minimizes potential pressure issues. As used herein, zonal tensioning means differentially tightening one or more specific areas or "zones" of the prosthetic device with the tightening system. Zonal tensioning may be preferred when increased pressure is desired in one or more areas/zones and/or decreased pressure is desired in one or more zones. The tightening systems described herein allows the user to control the zonal tensioning applied to the prosthetic device as desired.

The reel assembly of the lacing system may be operated to quickly and conveniently tension the lace and thereby tighten the prosthetic device about the unique or customized lace path so as to apply zonal pressure as desired to the patient's limb. In some embodiments, snap-in or easily coupled lace guides may be utilized to form or create the unique or customized lace path about the prosthetic device. As such, customization of the prosthetic device, which may be an off-the-shelf prosthetic/component or a specially designed prosthetic/component, is relatively straightforward and easy, and/or development and production of such prosthetic/components is relatively straightforward and easy. These advantages are not provided by conventional prosthetic tightening systems.

For convenience in describing the embodiments, the disclosure generally describes the tightening system using a reel based closure device or tensioning system. However, it should be realized that any tightening system or mechanism may be used to tighten the prosthetic device and that the disclosure is not limited to only the tightening system embodiments disclosed herein. For example, the tightening system may include or utilize various pull cords, pull straps, strap members, lace locks or clamps, and the like, or any combination thereof, to tighten the prosthetic device.

Figure 2:
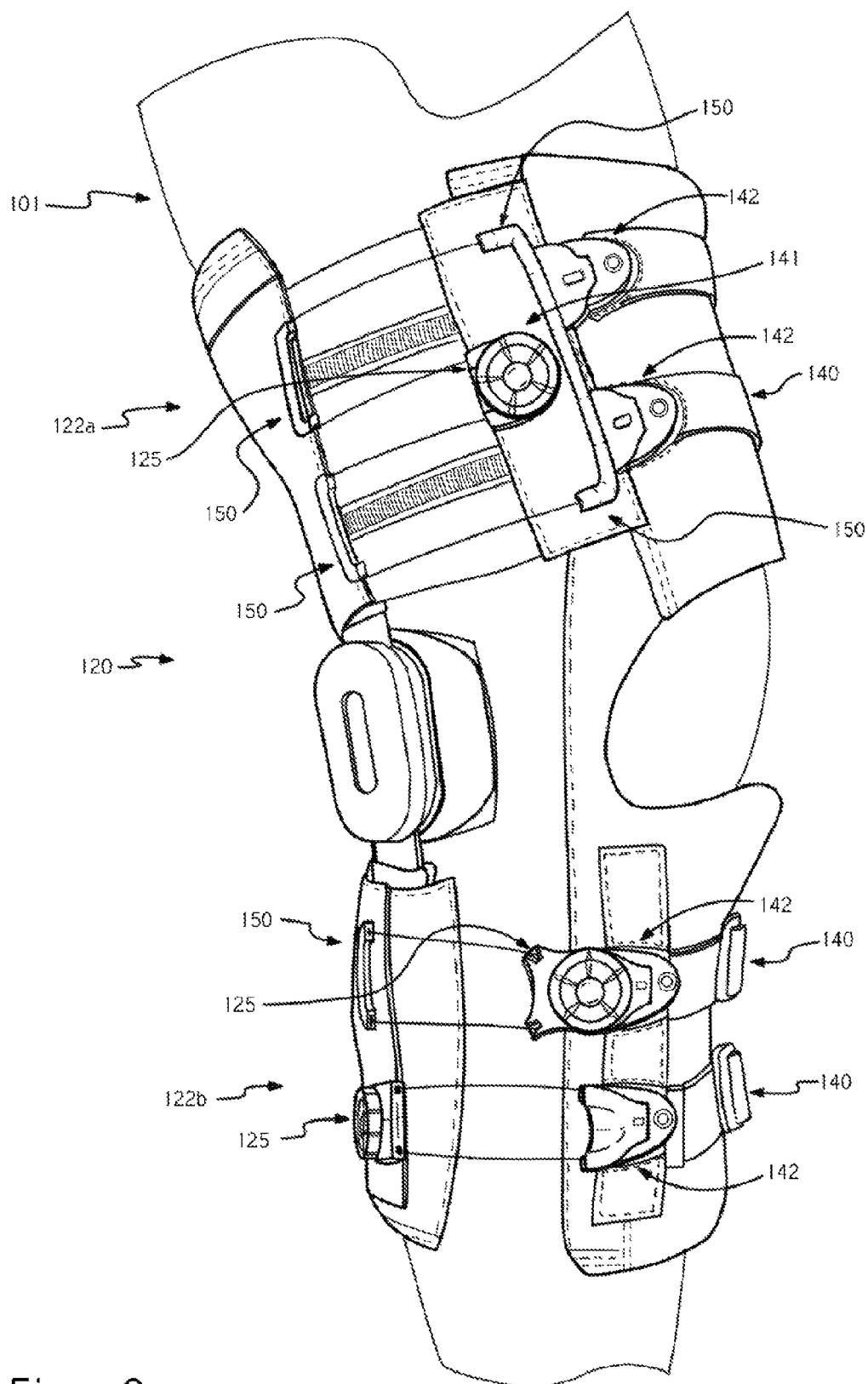
Figure 3:
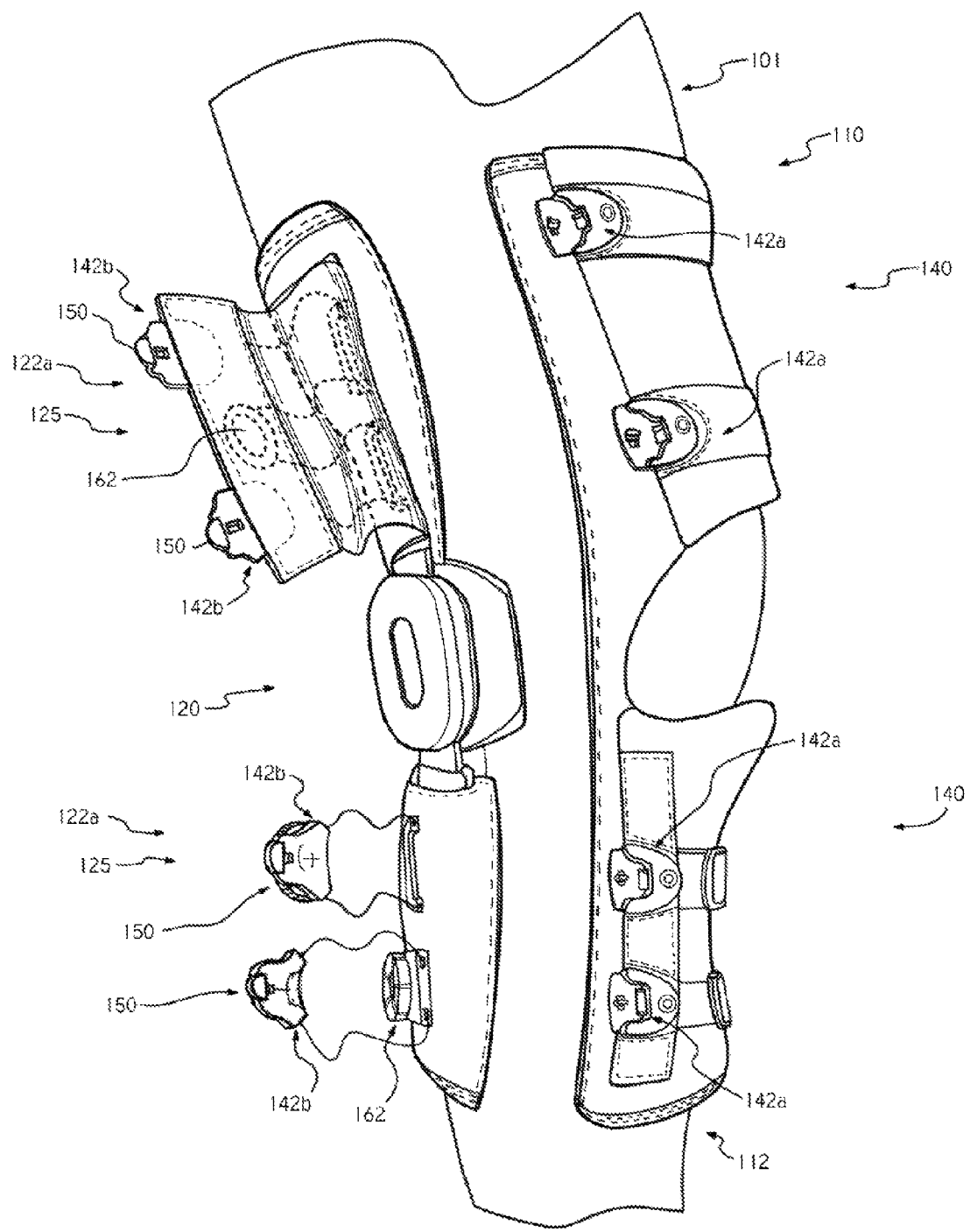
Figure 4A:
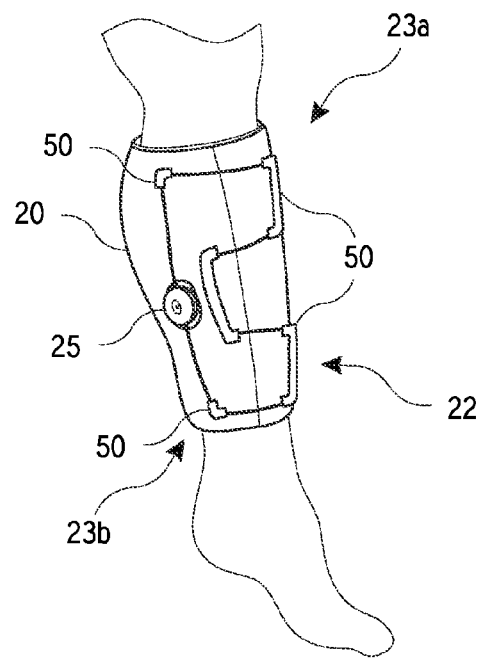
FIGS. 4A-D illustrate a brace using the tightening systems described herein adjusting to fit a conical shaped object.
Figure 4B:
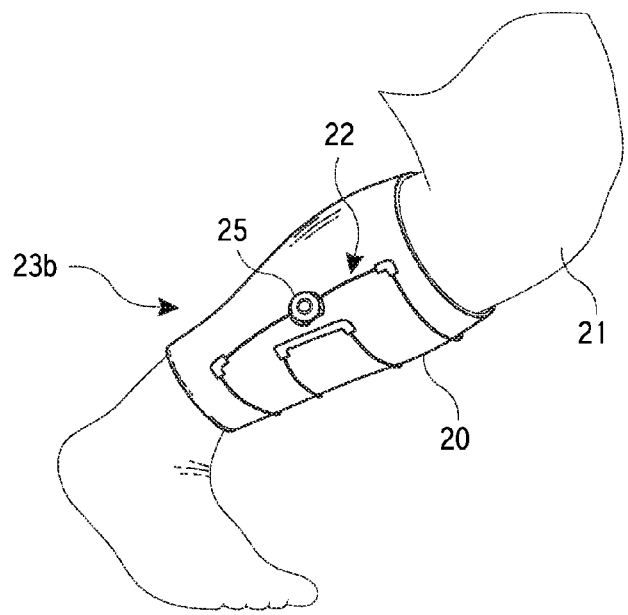
Figure 4C:
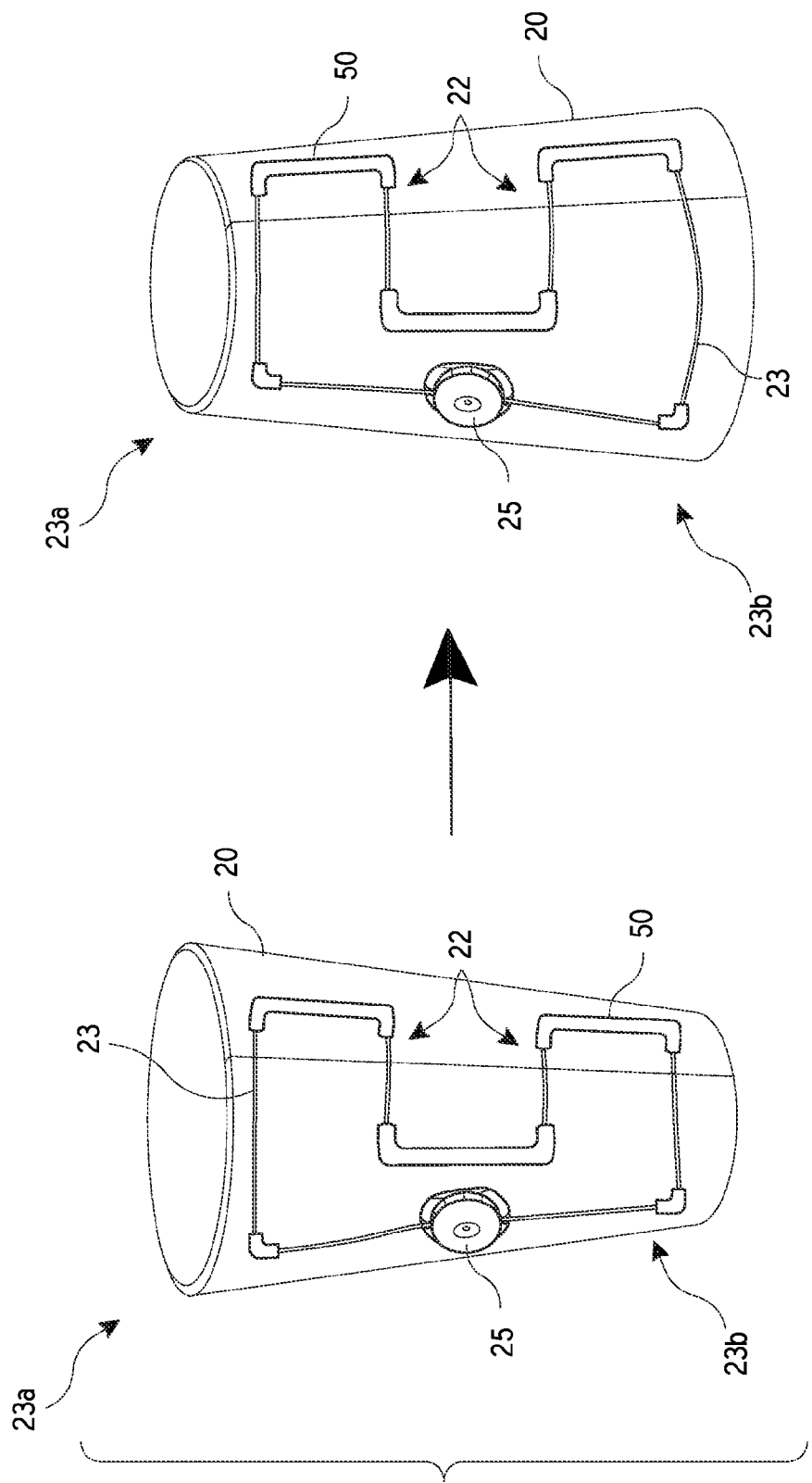
Figure 4D:
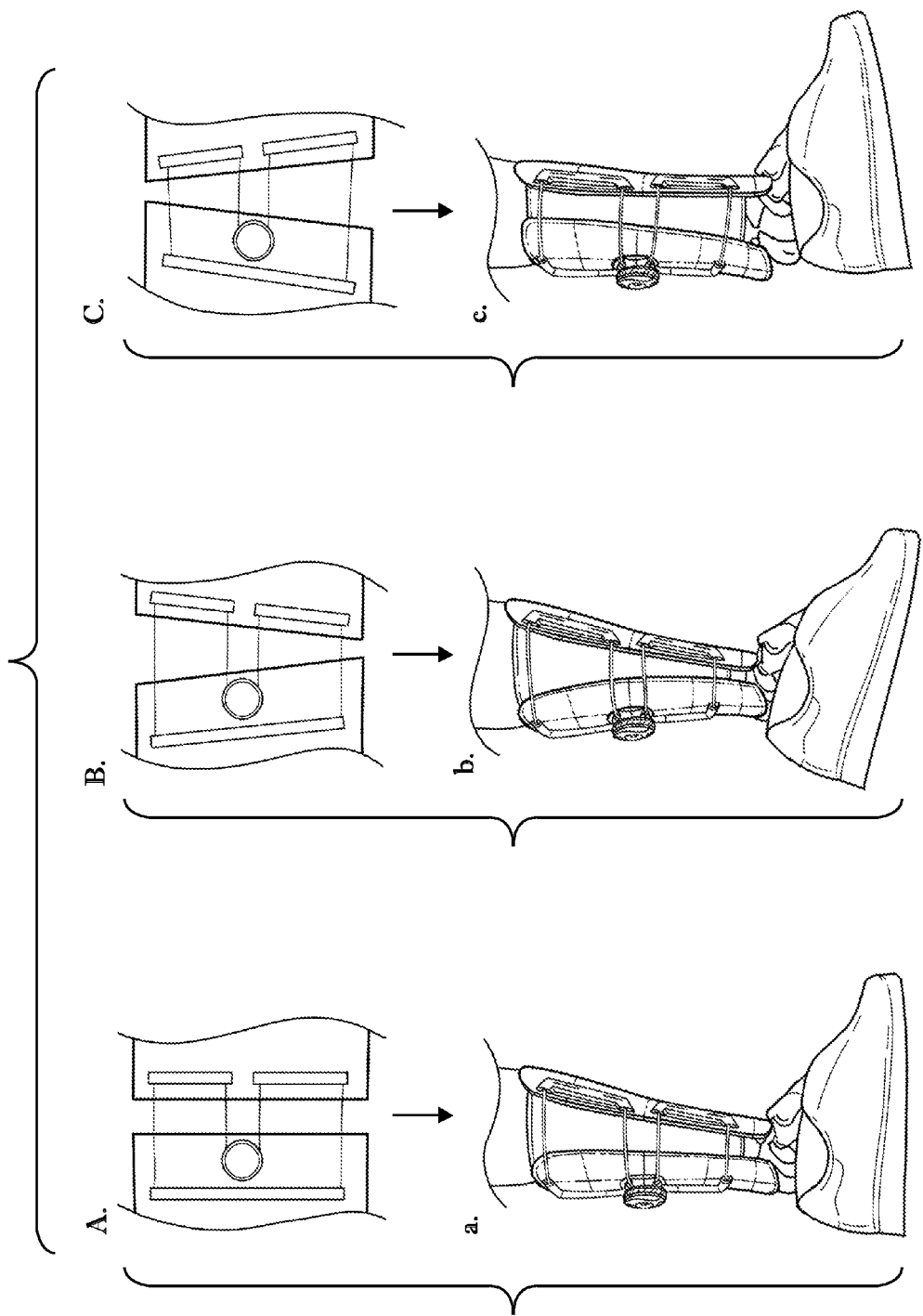

FIGS. 1-3 provide a general description of a tightening system that utilizes a reel based tensioning system and components thereof. FIGS. 1-3 provide an overview of general reel based systems. It should be realized, however, that the reel based system described in FIGS. 1-3 is only a general overview and that modifications may be made to the reel based system or components thereof in the various embodiments described herein.

Referring to FIG. 1, illustrated is an embodiment of an orthopedic brace 20. The orthopedic brace 20 generally comprises a knee brace that is tightened around a wearer's leg such that the knee brace substantially surrounds and protects the wearer's knee. Brace 20 may be tightened using a lacing configuration comprising two reel based tensioning systems 22a, 22b. The orthopedic brace of the illustrated embodiment is particularly concerned with relieving and/or supporting the knee joint. Although this illustrated embodiment shows the reel based tensioning systems applied to a knee braces, it is to be understood that the principles discussed herein are readily applicable to any of a variety of orthopedic braces, including ankle braces, wrist braces, foot braces, elbow braces and many other types of orthopedic braces well known to those of skill in the art.

In some embodiments, the configuration of tightening system comprises two distinct reel based tensioning systems 22a, 22b (hereinafter reel based systems). In some embodiments, each reel based system 22 includes a lace or cable 23 that is threaded through portions of the orthopedic brace and attached at opposite ends to a tightening mechanism 25 or reel assembly (hereinafter reel assembly 25), which includes a control such as a lever, crank or knob that can be manipulated to retract the lace 23. The reel assembly 25 may include a mechanism of release, such as a button or lever, for disengaging the reel assembly 25, to permit the lace 23 to be withdrawn freely. In other embodiments, the reel assembly 25 may be pulled upward to allow an internal spool to spin and the lace to be pulled freely. In yet another embodiment, the reel assembly 25 may be unwound (e.g., counterclockwise) to release the spool and allow the lace to be pulled, or to unwind the lace. As shown in FIG. 1, the lace 23 may be threaded in a crossing pattern along a generally forward-facing portion of the brace 20, between two generally parallel rows of side retaining members or straps 40. In another embodiment, the lace 23 may be threaded or run laterally across the brace 20. The straps 40 may consist of a strip of material attached to the brace 20 so as to define a space in which guides 50 are positioned. The lace 23 slides through the guides 50 during tightening and untightening of the lace 23. A more thorough description of the brace 20 and reel based systems, 22a & 22b, is provided in U.S. Pat. No. 8,277,401, the entire disclosure of which is incorporated by reference herein.

The orthopedic brace 20 shown in FIG. 1 is constructed to fit a wearer's leg. The upper cuff 10 is formed to fit the wearer's thigh and curves around the thigh, generally conforming to the wearer's musculature. The lower cuff 12 is similar in construction to the upper cuff 10, and is formed to fit and curve around the wearer's calf. In some embodiments, the upper and lower cuffs 10, 12 are formed from a relatively lightweight, breathable material. In some embodiments, the cuffs 10, 12 are manufactured from a cloth, fabric, or foam-like material, or a thermoformable or non-thermoformable plastic material as would be well-known to those skilled in the art.

As shown, each of the cuffs 10, 12 are generally formed from a single piece of material that is wrapped around itself, forming two ends 32, 34 that are drawn towards each other and, in fact, may overlap. Although the ends 32, 34 are shown in an overlapping position, it should be understood that these ends might also be sized to be separated by some distance when the orthopedic brace 20 is tightened. Generally, the lace 23 may be tensioned to draw the ends 32, 34 past each other and thereby tighten the orthopedic brace 20 about the wearer's limbs. As is readily understood in the art, the two ends 32, 34 of brace 20 are designed to be open and fit about a patient's leg. The two ends 32, 34 are then positioned over the leg and brace 20 is tightened as described above.

FIGS. 2 and 3 illustrate another brace 120 being fit over a wearer's leg 101. Brace 120 includes a reel based system (e.g., 122a and 122b) that is described in more detail in U.S. Pat. No. 8,277,401 incorporated herein. Brace 120 also includes a rough adjustment feature that permits further opening of the brace 120 to facilitate attachment of the brace 120 to a wearer's leg 101, while still providing the reel assembly/tightening mechanism 125 for final tightening. The rough adjustment feature may be variable length retaining members 140 that allow brace 120 to fit a wider variety of wearer's legs. In one embodiment, the variable length retaining member 140 includes adjustable straps. In other embodiments, a panel 141 that includes one or more components of the reel based system (e.g., reel assembly, lace, guides, and the like) may be used. The panel 141 may be coupled with a reel assembly 125 to provide gross or macro adjustment of the brace 120 and/or tightening of the brace about a limb. In some embodiments, retaining members 140 are configured to be releasably engaged with guides 150 positioned opposite the reel assembly 125 and/or attached to the panel 141.

The engagement may be by way of a quick release mechanism 142, such as those described in U.S. patent application Ser. No. 14/071,435, filed Nov. 4, 2013, entitled "Coupling Members for Closure Devices and Methods," the entire disclosure of which is incorporated by reference herein. In other embodiments, Fastex® buckles (shown), Velcro® or other similar mechanisms known to those of skill in the art may be used. As shown in greater detail in FIG. 3, each quick release mechanism 142 may include a female component 142a and a male component 142b that are coupled over the wearer's leg 101 to allow brace 120 to be donned and doffed. Exemplary embodiments of male and female components, 142b and 142a, are described in the '435 U.S. patent application incorporated hereinabove. In some embodiments, the female component 142a may be attached to the guide 150 while the male component 142b is attached to the retaining member, though the arrangement of components may be switched as needed. The opposite end of the retaining member 140 may be attached to the brace such that tension in the lacing system 122 causes tension on the retaining member 140 when the quick released mechanism 142 is engaged, thereby compressing the cuffs around the wearer's limb.

Reel based system 122 may include additional gross adjustment features in combination with the quick release mechanism 142 to provide a rough or gross adjustment of the closing pressure of the brace 120 prior to use of the reel assembly 125. For example, the reel based system 122 may include ladder locks (e.g., Fastex Slider®) which allow the retaining members 140 to be lengthened or shortened as needed. Though shown with two retaining members 140, as with the other embodiments disclosed herein in some embodiments, the number of retaining members 140 may vary. In some embodiments, three, four, five, six or more retaining members 140 may be desirable.

FIG. 3 shows one embodiment of the brace 120 in a partially open configuration. The quick release mechanism 142 have been disconnected leaving the guides 150 attached to the brace and releasing one end of the retaining member 140. To remove the brace 120, the user may open the cuffs 110, 112 and slide the brace from the user's leg 101. Prior to releasing the quick release mechanism 142, the user may release tension in the reel based system 122 by releasing the reel assembly 125, for example, by pulling outwards on the knobs 162. Alternatively, the user may release the reel assembly 125 after releasing the quick release mechanism 142 to facilitate reattachment of the brace 120 by providing additional slack in the system without adjusting the retaining members 140 themselves.

As shown in FIGS. 4A-D, one advantage of using the above described brace 20 and/or 120 is the increased ability of the brace 20 to fit a conical shape or an adjusting shape, such as a leg 21, arm, or any other body part of the individual. The ability of the brace 20 to fit a conical shape is provided by the reel based system 22. As the brace 20 is fit about a conical shape (e.g., the leg 21) and the lace 23 is tensioned/wound via the reel assembly 25, an upper portion 23a of the brace 20 contacts the conically shaped object. As the lace 23 is further tensioned, the lace 23 causes the brace to adjust until the lower portion 23b of the brace 20 also contacts the conically shaped object (e.g., the leg 21). Additional tensioning of the lace 23 will result in an approximately equal tensioning throughout the lace 23 and equal tightening of the brace, which provides a relative even pressure on the conically shaped object. As such, the brace 20 fits well on a conical shape.

Similarly, the brace 20 is able to adjust to changes in the shape of the object, such as changes in the shape of a leg 21 (or other body part) due to flexing and/or relaxing of the muscle. For example, as leg 21 is flexed and assumes a more cylindrical shape, the lace 23 is able to slide within, or relative to, the guides 50 so that a bottom portion 23b of the brace opens or widens as a top portion 23a contracts or shrinks. Conventional braces typically do not adjust in this manner and as such, when a patient flexes their leg 21 (or other body part), the brace 20 is typically forced to move or migrate about the body part, such as downward against the knee or ankle. In the embodiments described herein, because the lace 23 is able to slide relative to the brace 20 and guides 50, and the brace 20 is able to adjust to changes in shape, the fit or hold of the brace about the body part is increased and migration of the brace 20 is limited or eliminated.

Figure 5D:
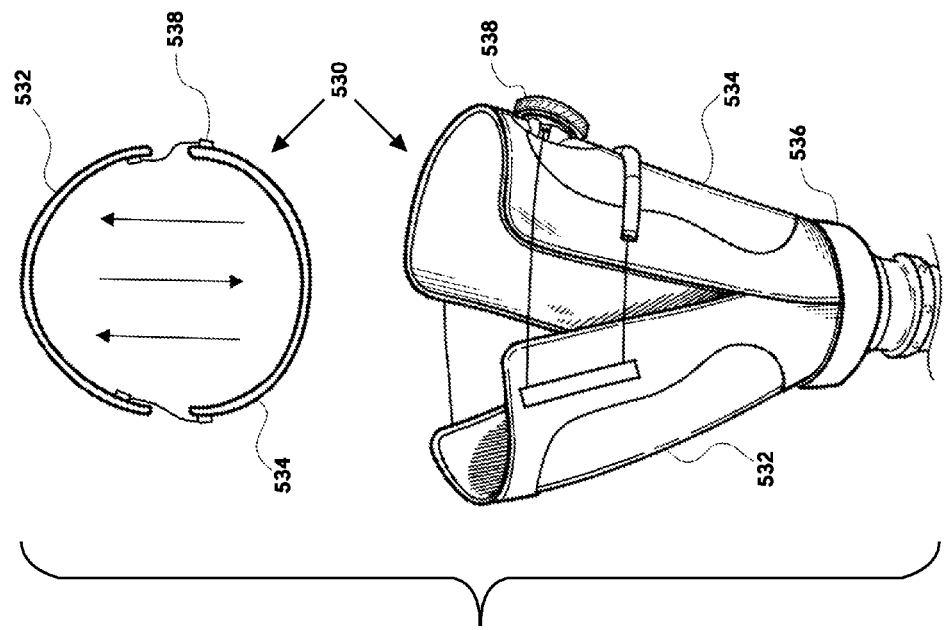
Figure 5C:
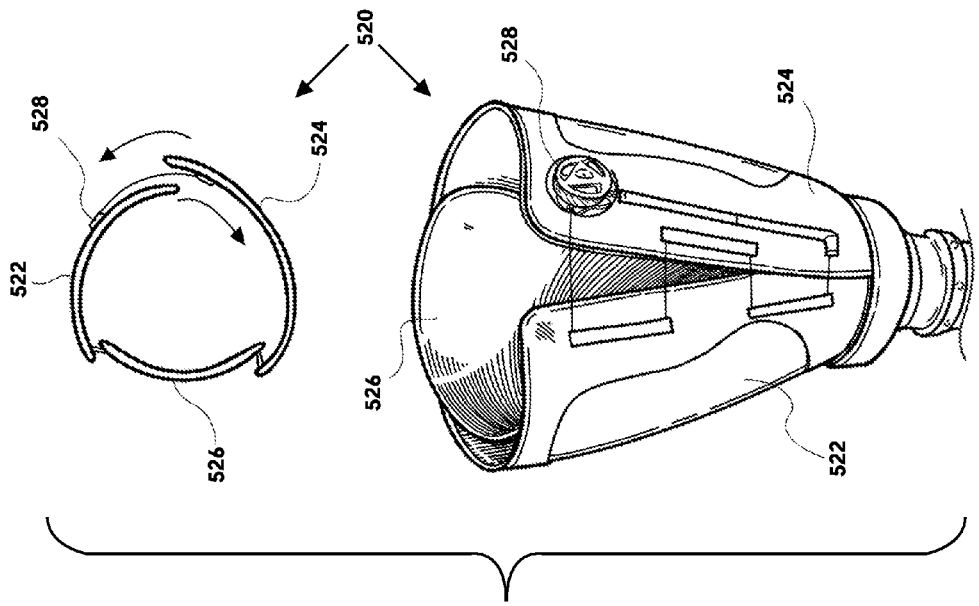

Referring now to FIGS. 5A-D, illustrated is a tightening system coupled with prosthetic shells of various shape. For example, in FIG. 5A a prosthetic 500 is a single canopy shell where a single tube shaped prosthetic element encircles a user's limb. An outer edge 502 of the shell 500 can extend and be slidably positioned over an inner edge 504 of the shell 500 to secure a user's limb within the shell 500. A reel based tensioning system 506 can be used to adjust the tightness or fit of the prosthetic shell 500 about the limb and/or to secure the prosthetic shell 500 to the limb. In FIG. 5B, a prosthetic shell 510 can include a hinged portion 512 that is coupled with a main body portion 516. For example, hinged portion 512 can include a hinge element 514 that may be positioned near a middle portion of the prosthetic shell 510. An upper portion of the hinged portion 512 can be separate from the main body portion 516 of shell 510, and can pivot relative thereto via hinge element 514. The upper portion of hinged portion 514 may be coupled with a reel based tensioning system 518 that is configured to control pivoting of the hinged portion 512. The reel based tensioning system 518 can be loosened to pivot the hinged portion 512 away from main body portion 516, which allows for insertion and/or removal of a limb into the prosthetic shell 500. The reel based tensioning system 518 can also be tightened to create a secure fit of the prosthetic shell 500 about the limb. In FIG. 5C, a double canopy prosthetic shell 520 can be used. Double canopy shell 520 can include a three-piece shell arrangement in which two side segments 522 and 524 are slidably positioned over a fixed back segment 526. One of the two side segments, 522 or 524, can be slidable positioned in front of the other side segment, 522 or 524. The two side segments, 522 and 524, can be adjusted using a reel based tensioning system 528 to constrict the three prosthetic shell segments (522, 524, and 526) about the user's limb and thereby ensure a proper fit. Reel based tensioning system 528 can be loosened to radially open the three-segment shell 520 to allow insertion and/or removal of a limb into the prosthetic shell 520. The reel based tensioning system 528 can also be tightened to constrict the three-segment shell 520 about the limb. In FIG. 5D, a two-segment clamshell construction may be used to form a prosthetic shell 530. The two-segments 532 and 534 of the prosthetic shell 530 may be pivotally coupled at a base 536 of the prosthetic shell 530 to allow the first segment 532 to be pivoted relative to the second segment 534. In this configuration, the first segment 532 can be pivoted away from the second segment 534 by loosening the reel based tensioning system 538 and thereby allow for insertion or removal of a limb into the prosthetic shell 530. Similarly, the first segment 532 can be pivoted closer to the second segment 534 by tightening the reel based tensioning system 538 to constrict or tighten the prosthetic shell 530 about a user's limb. The lace of the reel based tensioning system 538 can span an open portion of the first segment 532 and second segment 534 to couple the two segments together. The use of the reel based tensioning systems on prosthetic and/or orthotic devices can not only ensure a proper fit, but can also ensure that adjustments of tightness, fit, and/or comfort can easily be made throughout the day by tightening or loosening the lace.

Figure 6:
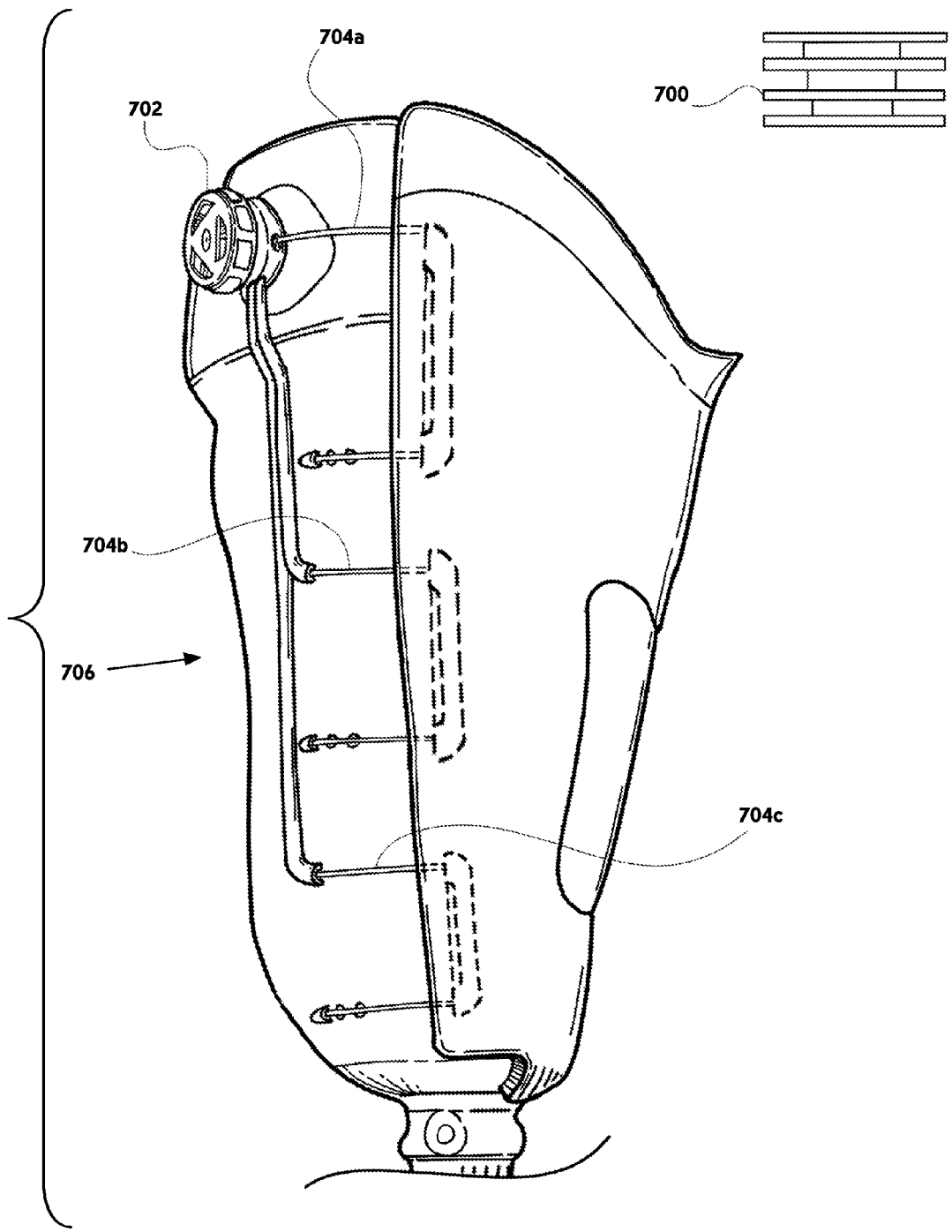
FIG. 6 illustrates a lace configuration of a brace and a multi-tiered spool that may be used to differentially tension multiple laces with a single reel assembly.

In some embodiments, a reel assembly may utilize spools that can store multiple laces. These reel assemblies may allow multiple zones or areas of a brace to be differentially adjusted using a single reel assembly. For example, FIG. 6 shows a three-tiered spool 700 that may be used to differentially tension three laces with a single reel assembly 702. The reel assembly 702 is able to tension or loosen all of the laces 704a, 704b, and 704c simultaneously. In some embodiments, a proximal end of each of the three laces 704a, 704b, and 704c can terminate at or near the reel assembly 702 while a distal end of each lace 704a, 704b, and 704c terminates on the prosthetic shell 706, preferably on the same side. In some embodiments, the lace termination ends can be varied to vary the length of lace available for tensioning a respective zone and thereby create differential tension in one or more zones of the prosthetic shell 706. Various embodiments of reel based tensioning systems that may be used to create zonal pressure and/or vary lace ends are described in U.S. patent application Ser. No. 14/073,773, filed Nov. 6, 2013, entitled "Devices and Methods for Adjusting the Fit of Footwear," the entire disclosure of which is incorporated by reference herein.

Figure 7A:
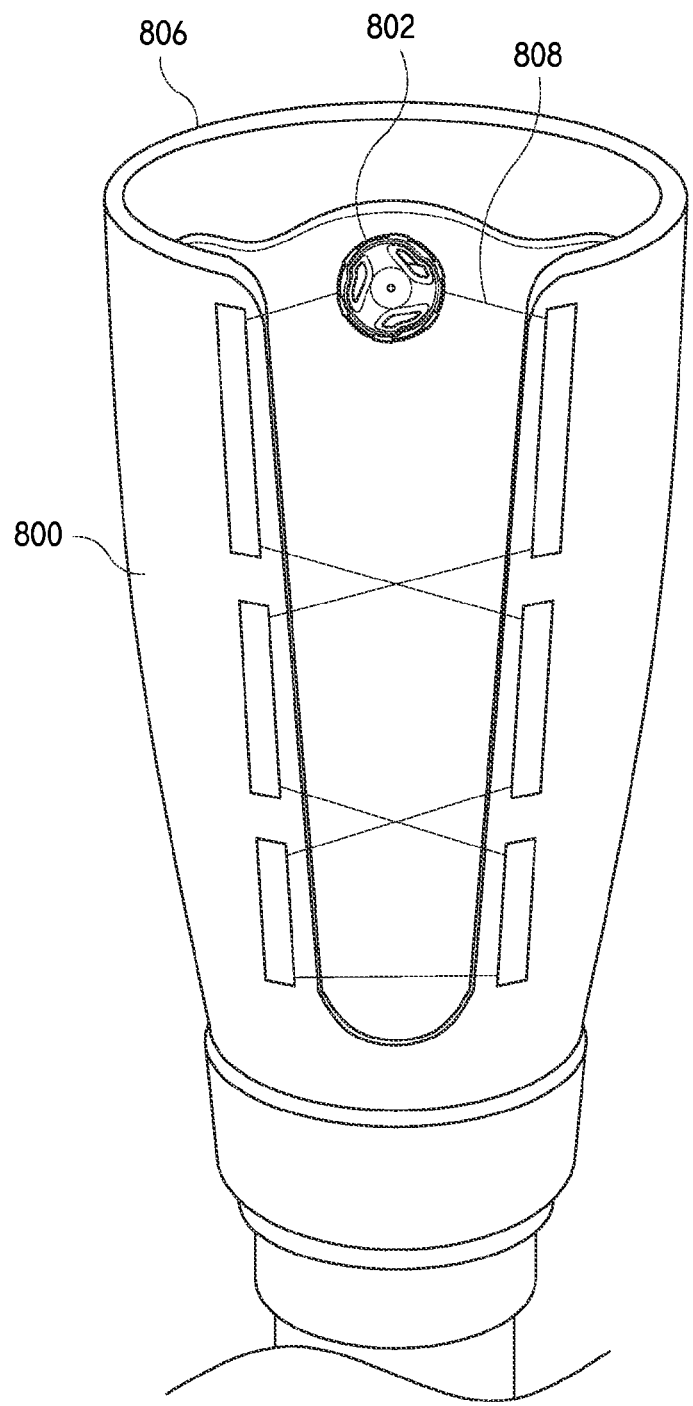
FIGS. 7A-D illustrate various embodiments of using a lace or tension member to close and tighten a brace.
Figure 7B:
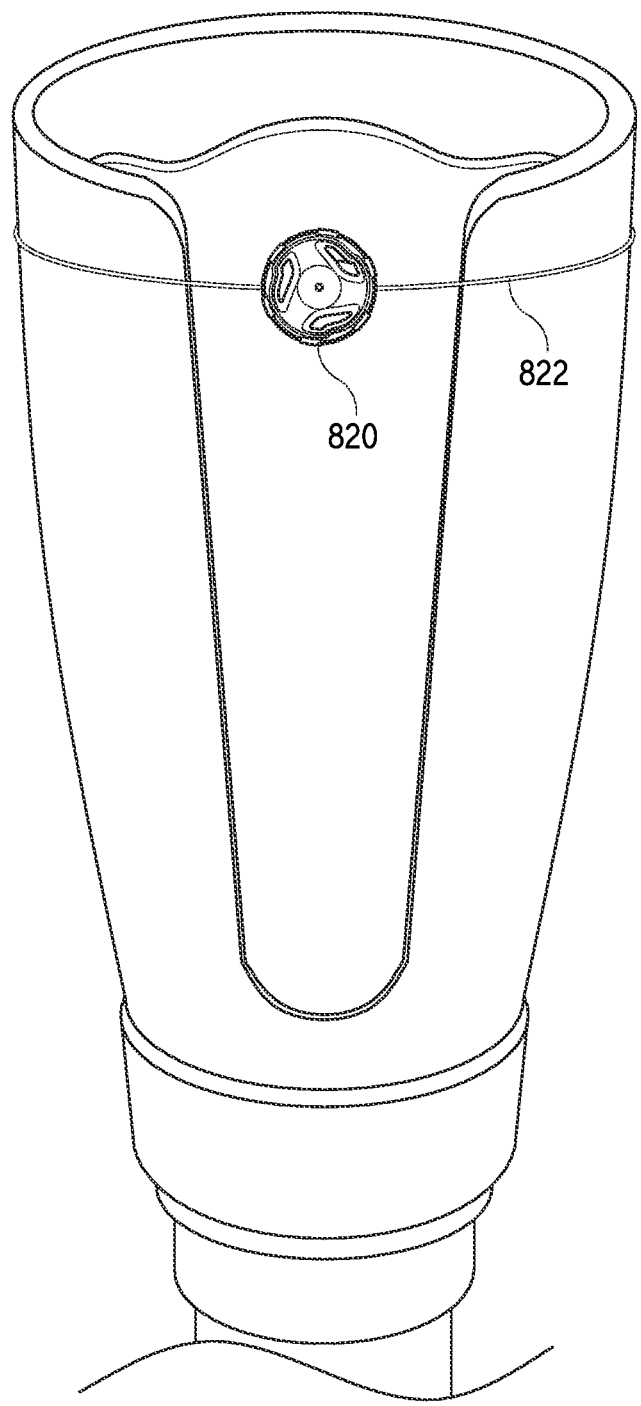
Figure 7C:
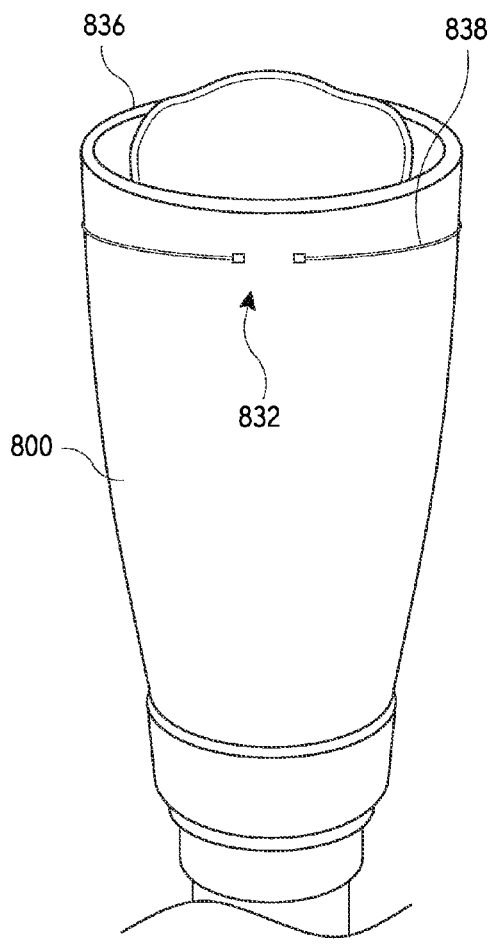
Figure 7D:
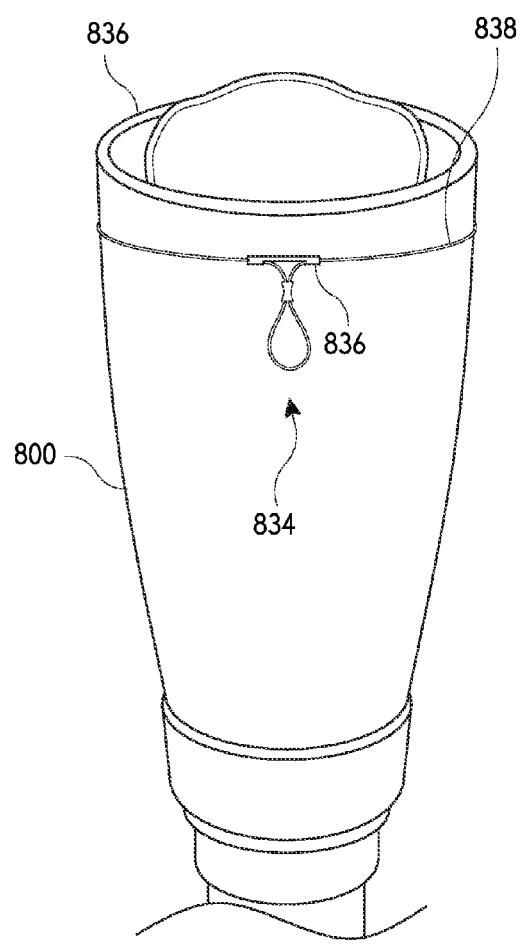

FIGS. 7A-D illustrate various embodiments of using a lace or tension member to close and tighten a brace. For example, FIG. 7A shows a reel assembly 802 that creates a pressure zone along a longitudinal opening of a prosthetic shell 800. In some embodiments, a second reel assembly can also be coupled with the shell 800 and operable to tension a zone of the shell. In some embodiments, the second reel assembly may be placed on the shell 800 opposite the first reel assembly 802, such as on a back of the shell 800. The second reel assembly can create a pressure zone along a separate portion of the shell 800, for example, along a collar 806 of the shell 800 to compress the top portion or region of the shell 800 about the limb. The second reel assembly can be positioned in line with a lace 808, or away from the lace 808. In embodiments wherein the second reel assembly is positioned away from the lace 808, a displaceable guide may be used to tension the lace 808 as the second reel assembly 804 is operated. The displaceable guide may be pulled toward the second reel assembly 804 to tension the lace 808. Alternatively, a single reel assembly may be used to adjust the collar portion of shell 800 and the longitudinal opening of the shell 800. FIG. 7B illustrates an embodiment in which a reel assembly 820 is coupled with a lace 822 that wraps circumferentially around the brace. The lace 822 is tensionable to squeeze or constrict the top portion of the brace about a user's limb. FIGS. 7C and 7D illustrate embodiments in which distal ends of a lace 838 may be attached to the brace. In FIG. 7C, the distal end of the lace 832 may be fixedly attached with the brace 800. In this embodiment, tensioning of the lace 838 effects squeezing or closure of the collar portion 836 of the brace 800 about the user's limb. In FIG. 7D, the distal end 834 of the lace 838 is adjustably coupled with the brace 800. In this embodiment, the distal end 834 may be pulled through a lace guide 836 to effect an initial closer of the collar portion 836 of the brace 800 about the limb. The distal end 834 may then be crimped or locked in position so that further tensioning of the lace 838 via a tensioning mechanism further tightens the collar portion 836 of the brace 800 about the limb. In this manner, the lace 838 can be used to perform a macro or gross adjustment of the brace 800 about the limb.

Figure 8:
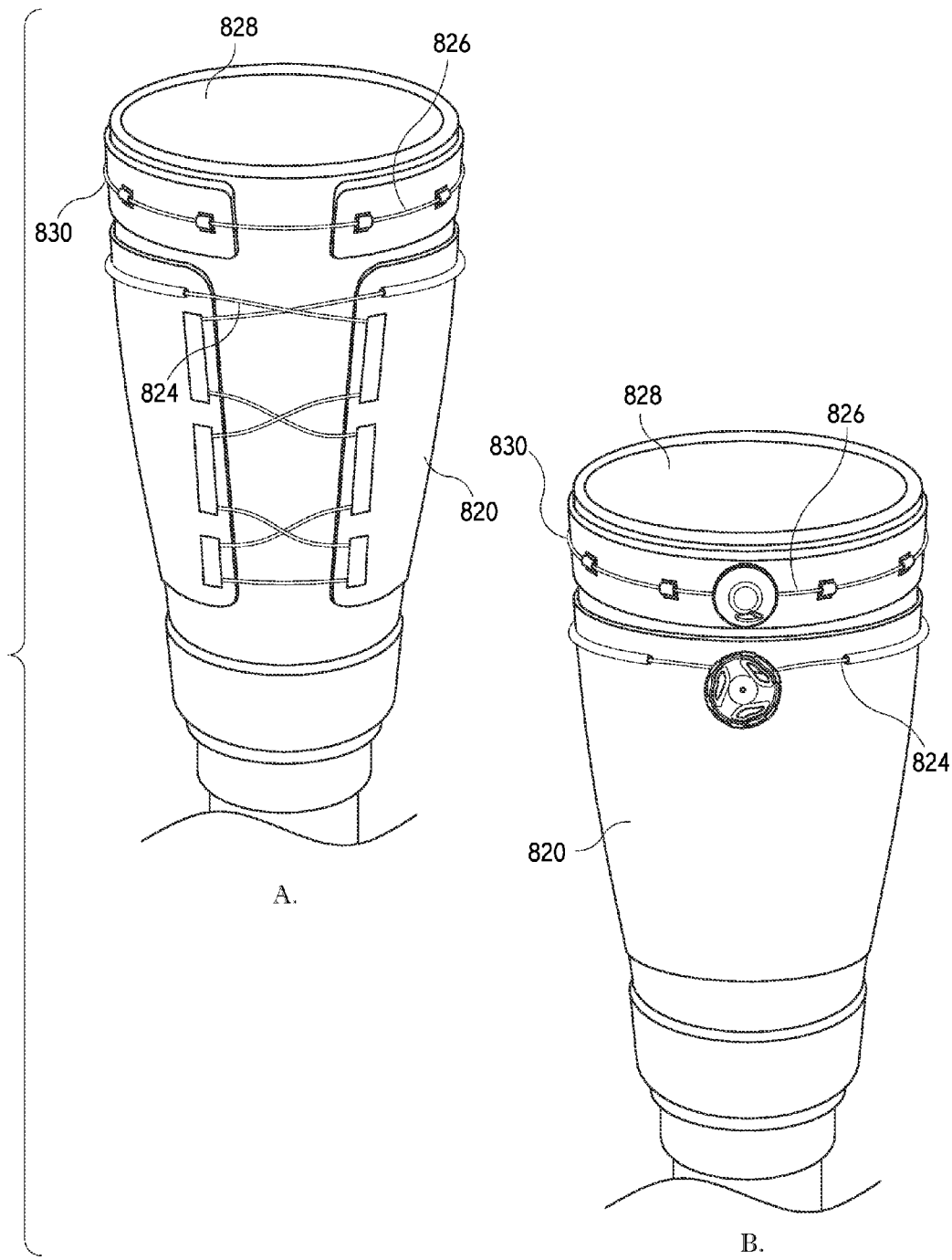
FIG. 8 illustrates padded members that can be used to create one or more pressure zones for a reel based tensioning system.

In some embodiments, padded members may be used to create pressure points within a brace. The padded members can be included to focus pressure, distribute pressure, and/or create a more comfortable fit for the user. Padded members may be created from foam, gel, or other spongy and/or flexible materials. For example, in FIG. 8, padded members can be included to create one or more pressure zones for reel based tensioning systems 824 and 826. A shell 820 can include a pressure zone along a longitudinal opening of the shell 820. Shell 820 can also include a second pressure positioned near or along a collar 828 of the shell 820. The collar pressure zone 828 includes one or more padded members 822, which are radially displaceable through windows positioned circumferentially around the shell's collar 828. In some embodiments, the padded members 822 may be positioned at approximately equal intervals around the prosthetic 820, or at other locations that would ensure a proper and/or comfortable fit for the user. As lace 830 is tensioned, the padded members 822 are displaced radially inward through the windows to reduce the volume of the prosthetic against the user's limb and thereby increase the pressure against the limb. In other embodiments, the padded member 822 may press against a resilient material or diaphragm that in turn presses against the user's limb.

Figure 9:
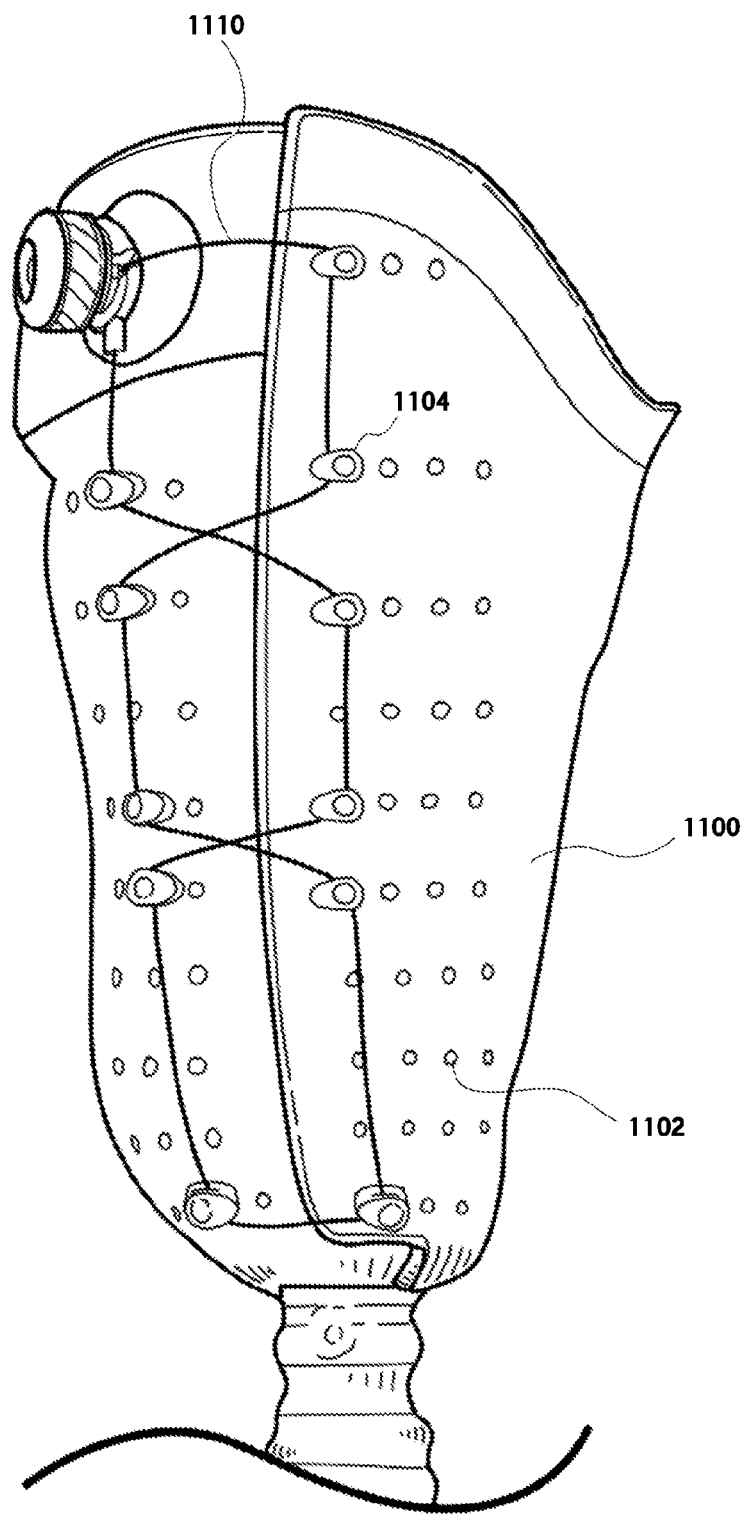
FIG. 9 illustrate a prosthetic shell that may be used to create a customized lace path about the prosthetic shell in order to provide a customized fit of the shell about the limb.

In some embodiments, customized lace paths may be created on a prosthetic by utilizing the appropriate lace guides. For example, FIG. 9 shows a single canopy shell 1100 having multiple rivet holes 1102. Guides having rivets or pegs can be inserted into the rivet holes 1102 to create a desired lace path that produces a desired pressure or prosthetic tightening arrangement. Any guide that can be riveted or snapped into the rivet holes 1102 can be used. For example, a guide 1104 can be used to direct segments of a lace 1110 in different directions along the shell 1100. Various riveted guides can be used to create different radii to alter the tension that is applied at a specific portion of the shell 1100 and can be selected to reduce friction within a lace system.

Figure 11A:
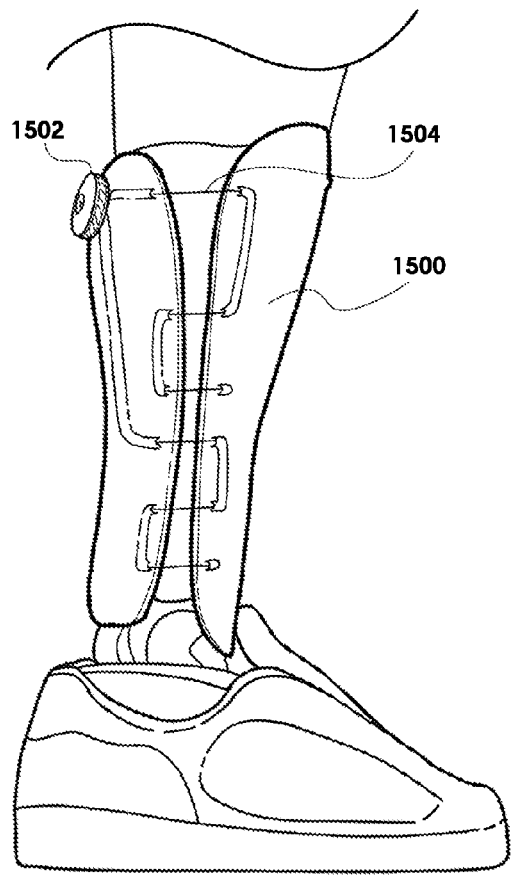
FIGS. 11A and 11B illustrate teeter mechanisms that may be incorporated into or coupled with a prosthetic shell to allow differential tensioning or tightening of different areas or zones of the prosthetic shell.
Figure 11B:
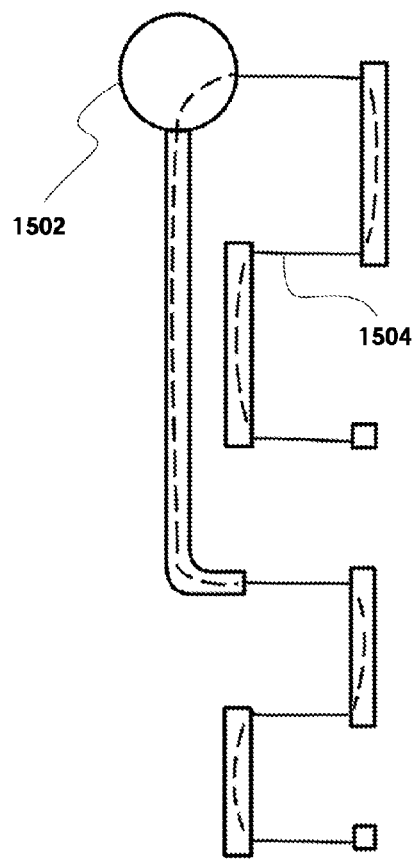

FIGS. 11A and 11B illustrate teeter mechanisms that may be incorporated into or coupled with a prosthetic shell to allow differential tensioning or tightening of different areas or zones of the prosthetic shell. As used herein, a teeter mechanism refers to any device that is capable of increasing the lace length in one zone of a prosthetic device while decreasing the lace length in another zone of the prosthetic device. The teeter mechanisms may include a reel assembly that allows the lace to be pulled through, or otherwise moved, relative to the reel assembly and then locked in position. In this manner, the lace length in multiple zones may be adjusted by the use of a teeter mechanism. As shown in FIG. 11B, by using a teeter mechanism 1502, a user can adjust the pressure applied by a prosthetic shell 1500 in multiple zones by pulling a portion of the lace 1504 to one side of a reel 1506 or the other and locking the lace 1504 in position relative to the teeter mechanism 1502. The lace 1504 may be locked in position by rotating a knob of the teeter mechanism 1502 or otherwise operating a lock or locking mechanism. In this manner, when the lace 1504 is tensioned via a reel assembly, the pressure within each zone on either side of the teeter mechanism 1502 is varied. In some embodiments, the reel assembly may be the same device as the teeter mechanism. For example, the teeter mechanism 1502 may include a lumen that allows the lace 1504 to be pulled through the teeter mechanism. The teeter mechanism 1502 may then be operated as described above (e.g., rotating a knob) to tension the lace 1504 and thereby tighten the brace about a user's limb. As shown in FIG. 11A, the teeter mechanism 1502 may be used to vary the pressure within an upper zone and lower zone of the prosthetic device, and thereby vary the pressure applied to the limb in the upper and lower regions of the prosthetic device respectively. Various embodiments of teeter mechanisms are further described in the '773 application, which is incorporated by reference herein.

In some instances it may be desired to use a lacing system to simultaneously tension multiple tension members or laces. In such embodiments, the lacing system may include a tensioning device, a tensioning mechanism that is operated via the tensioning device, and a plurality of tension members or laces that are coupled with the tensioning mechanism and tensionable thereby. The plurality of tension members may be arranged longitudinally about an opening of an article and configured to narrow a gap of the opening upon tensioning of the plurality of tension members in order to tighten an article, such as a prosthetic or orthotic brace as described herein. In such embodiments, operation of the tensioning mechanism effects a simultaneous and repeatable tensioning of each tension member to achieve a relatively uniform tightening of the article. As used herein, the term simultaneous tensioning means that the each of the tension members is tensioned at roughly the same time and is not depending on tensioning a proximal portion of the tension member. For example, in conventional systems where a single or a few tension members or laces are employed in tightening an article, the distal portions of the tension member are not tensioned until the proximal portions of the tension member are tensioned. Given the frictional loses that are experienced in conventional systems, the distal portions of the tension member may not fully tension until the tension member shifts about the article and/or within one or more lace guides. As a result, the distal portions of the article that are tensioned via the distal portions of the tension member may not immediately tighten in relation to the proximal portions.

As also used herein, the term repeatable tensioning means that the tensioning of each tension member may be roughly equivalent each time the tensioning device is operated. Stated differently, each tension member may be configured to tighten an article at a given or desired rate in relation to the other tension members. Afterwards, each subsequent operation of the tensioning device may effect tightening of the article at the given or desired rate. The use of conventional systems, where the distal portion of the tension member is tensioned only after tensioning of the proximal portion, does not result in repeatable tensioning or tightening of an article. For example, due to frictional and other loses, the proximal portion of the article typically tightens before the distal portion of the article. The tightness of the article then may equalize or normalize over time as the tension member shift about the article and/or within one or more lace guides. As such, the tensioning or tightening of the tension member and article varies. In contrast, by using the embodiments described herein, the tensioning of each tension member and corresponding tightening of the article is repeatable and relatively uniform in relation to conventional systems.

In some embodiments, one or more of the plurality of tension members is adjustably coupled with the article. For example, the distal end of the tension member may be moved or repositioned about the article, which results in a different lace tension being produced in the tension member. Adjustment of the tension member in this manner may be used to achieve a different or differential tensioning of the respective tension member upon operation of the tensioning mechanism. The tension members may be adjustably coupled with the article via: an adjustable terminating end, a teeter mechanism, a lock mechanism, a buckle, and the like.

Figure 12A:
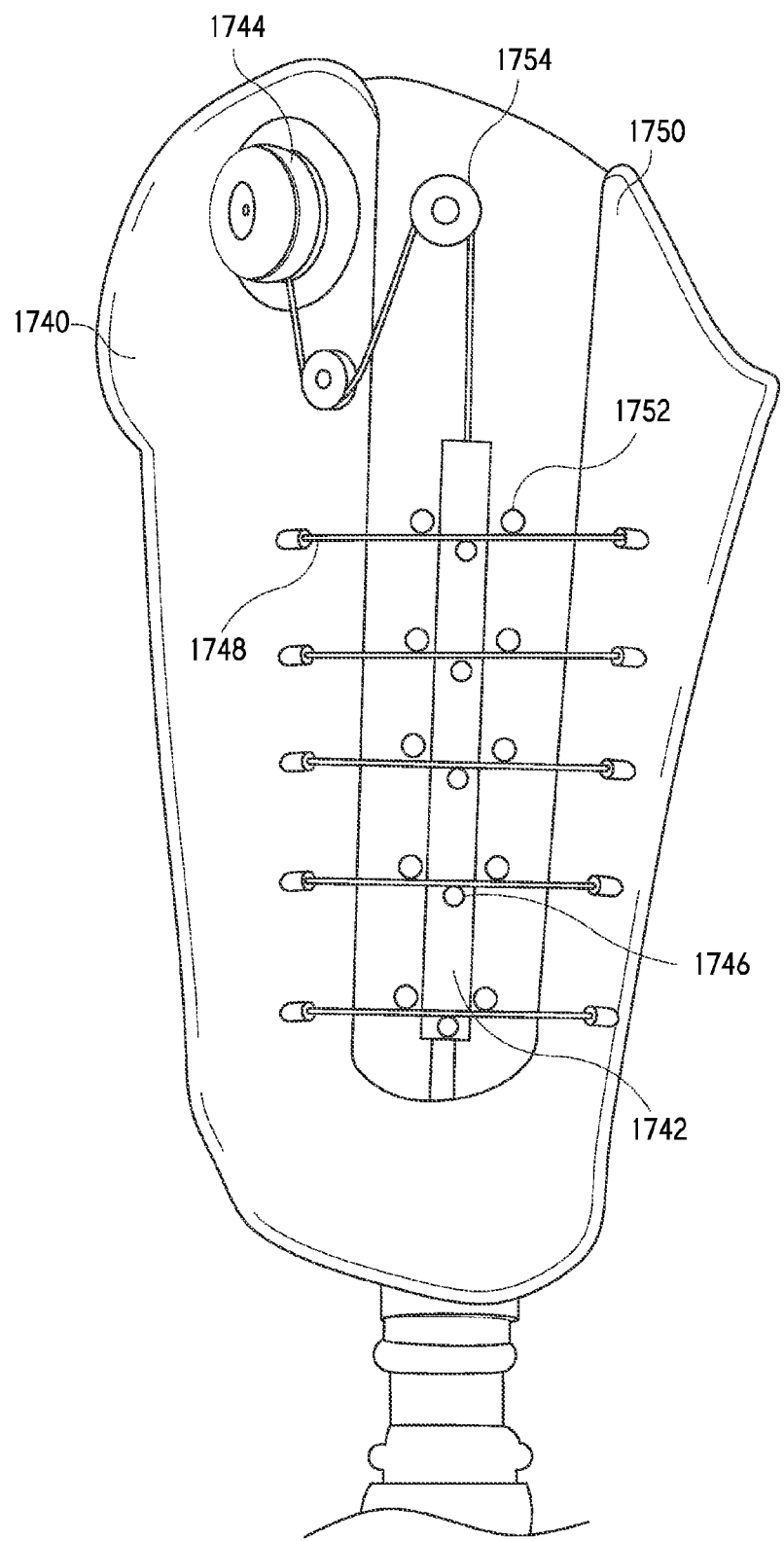
FIGS. 12A-C and 16A-17C illustrate embodiments of lacing systems that may be used to simultaneously tension multiple tension members or laces.
Figure 12B:
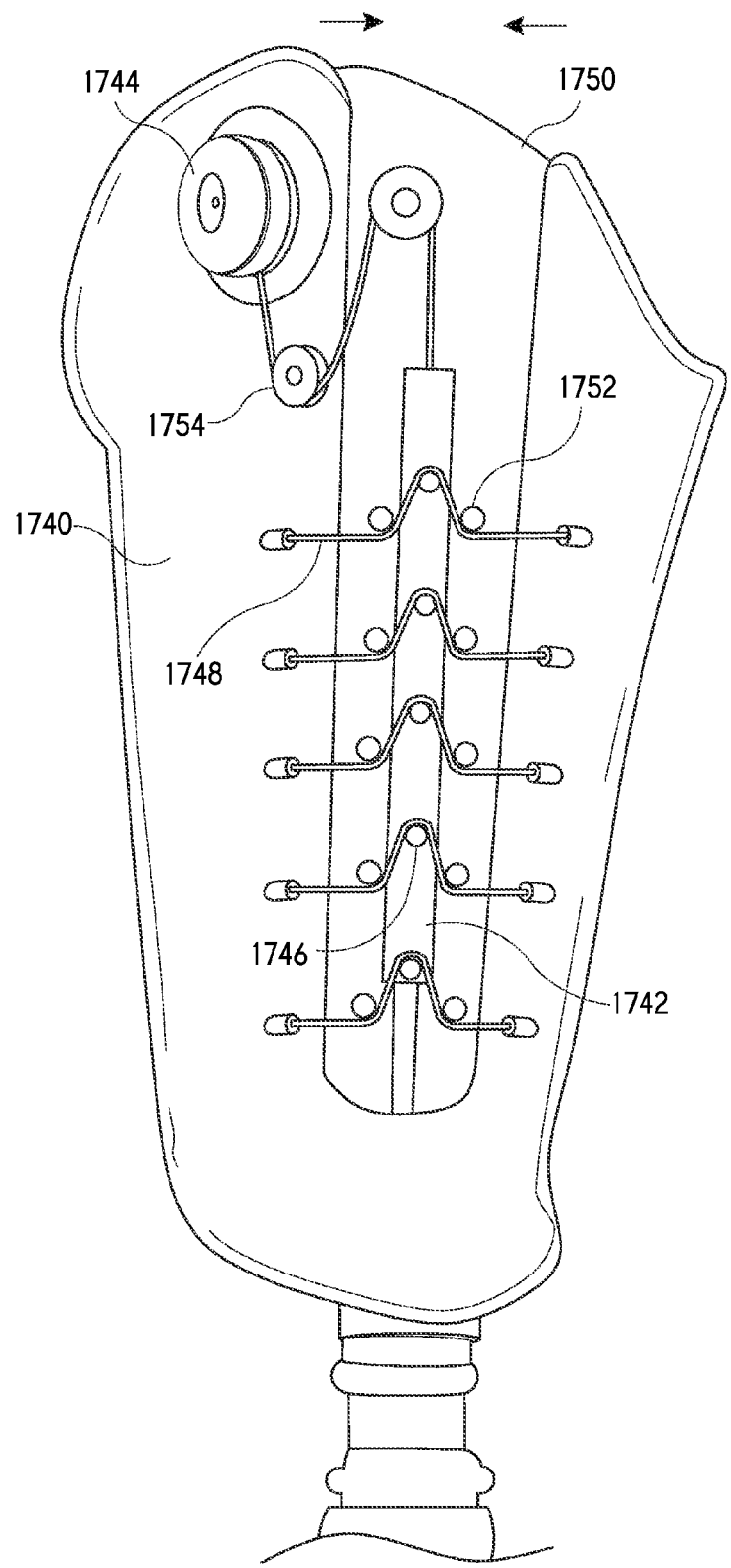
Figure 12C:
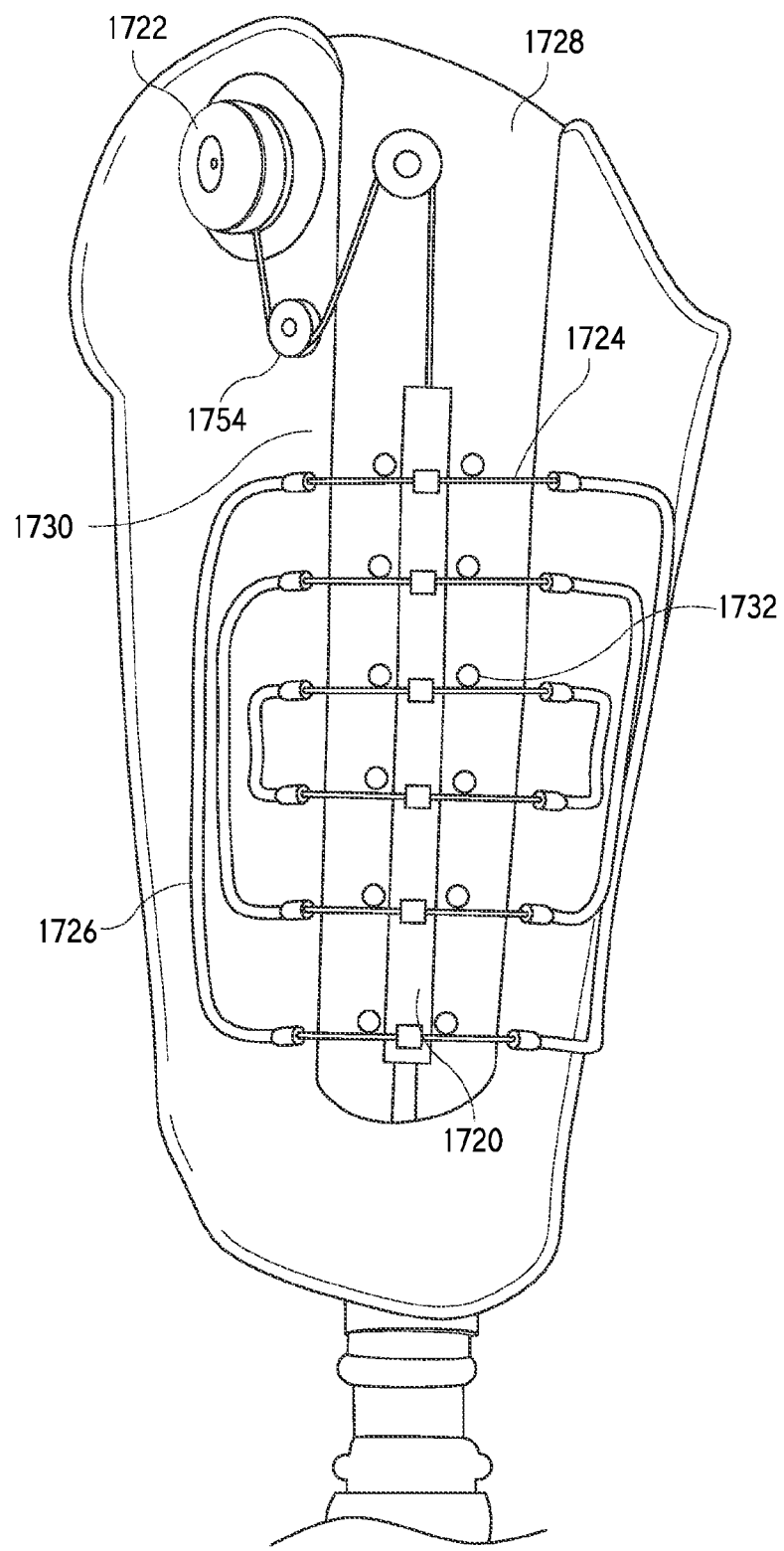

FIGS. 12A-C and 16A-17C illustrate embodiments of lacing systems that may be used to simultaneously tension multiple tension members or laces. FIGS. 12A-C illustrate embodiments of elongate members or tension bars (hereinafter tension bars) that may be used to tension a plurality of laces relatively uniformly. In FIG. 12C, a tension bar 1720 is coupled with a reel based tensioning system 1722 as well as with multiple transverse laces 1724 that span a compression gap 1728 of a prosthetic shell 1730. As the reel based tensioning system 1722 is tightened, the tension bar 1720 displaces longitudinally upward from a first position in which the laces are relatively loose, to a second position in which the laces are tensioned. Displacing the tension bar 1720 to the second position may consist of pulling the tension bar 1720 upward and towards the reel based tensioning system 1722. In some embodiments, the transverse laces 1724 that span the compression gap 1728 may contact and slide about posts 1732 as the tension bar 1720 is pulled toward the reel assembly 1722. The posts 1732 may control the radius of curvature of the laces 1724 and direct the closure force inward and/or across the gap 1728 as the tension bar 1720 tensions the transverse laces 1724. As the tension bar 1720 tensions the transverse laces 1724, the transverse laces 1724 pull the opposing sides of the compression gap 1728 inward to compress the prosthetic device about the limb. In some embodiments, rollers, bearings, or other components may be used instead of posts 1732 to direct the transverse laces 1724.

As shown in FIG. 12C, the transverse laces 1724 are slidingly disposed within or about guides 1726 on opposing sides of the compression gap 1728. A single transverse lace 1724 is coupled with the tension bar 1720 at two distinct longitudinal positions. The lace 1724 is able to slide within a guide 1726 between the two distinct longitudinal positions. In this manner, the tension within the multiple laces is dynamically equalized or balanced. By using guides 1726 of different lengths, the relative amount of pressure applied to the limb at different positions of the shell 1720 can be controlled. Since the laces 1724 are able to slide within the guides 1726 and thereby adjust, the lace tension in this embodiment may be equalized or balanced to a greater degree than other embodiments.

FIGS. 12A and 12B illustrate an embodiment of a prosthetic shell 1740 using a tension bar 1742 as previously described to create a uniform compression along a compression zone of the shell 1740. In the illustrated embodiment, a reel based tensioning system 1744 is coupled with the tension bar 1742 and is operable to tension a plurality of laces 1748 that span a compression gap 1750 of the shell 1740. The laces 1748 are attached on opposing ends with the prosthetic shell 1740 and span the gap 1750. A middle portion of the laces 1748 contact posts 1746 and 1752 as described above to direct the closure force laterally across the gap 1750 and thereby pull opposing sides of the gap 1750 towards one another. In this manner, the shell 1740 may be constricted or compressed against the limb of the individual to secure the shell 1740 to the limb. In some embodiments, the reel based tensioning system 1744 directly pulls or tensions the tension bar 1742. In other embodiments, pulleys 1754 or other components may be used to direct the force applied by the reel assembly 1744 to the tension bar 1742. By selecting the appropriate pulley 1754, or pulley system, the force applied to the tension bar 1742 can be enhanced to achieve a desired compression characteristic. Unlike the embodiment of FIG. 12C, the lace 1748 of FIGS. 12A and 12B is not disposed within guides that route the lace between two positions of the tension bar 1742. Rather, each individual lace segment 1748 is attached at opposing ends with the shell 1740 and disposed across the gap 1750 so that the lace 1748 is roughly orthogonal to the gap 1750.

Figure 16A:
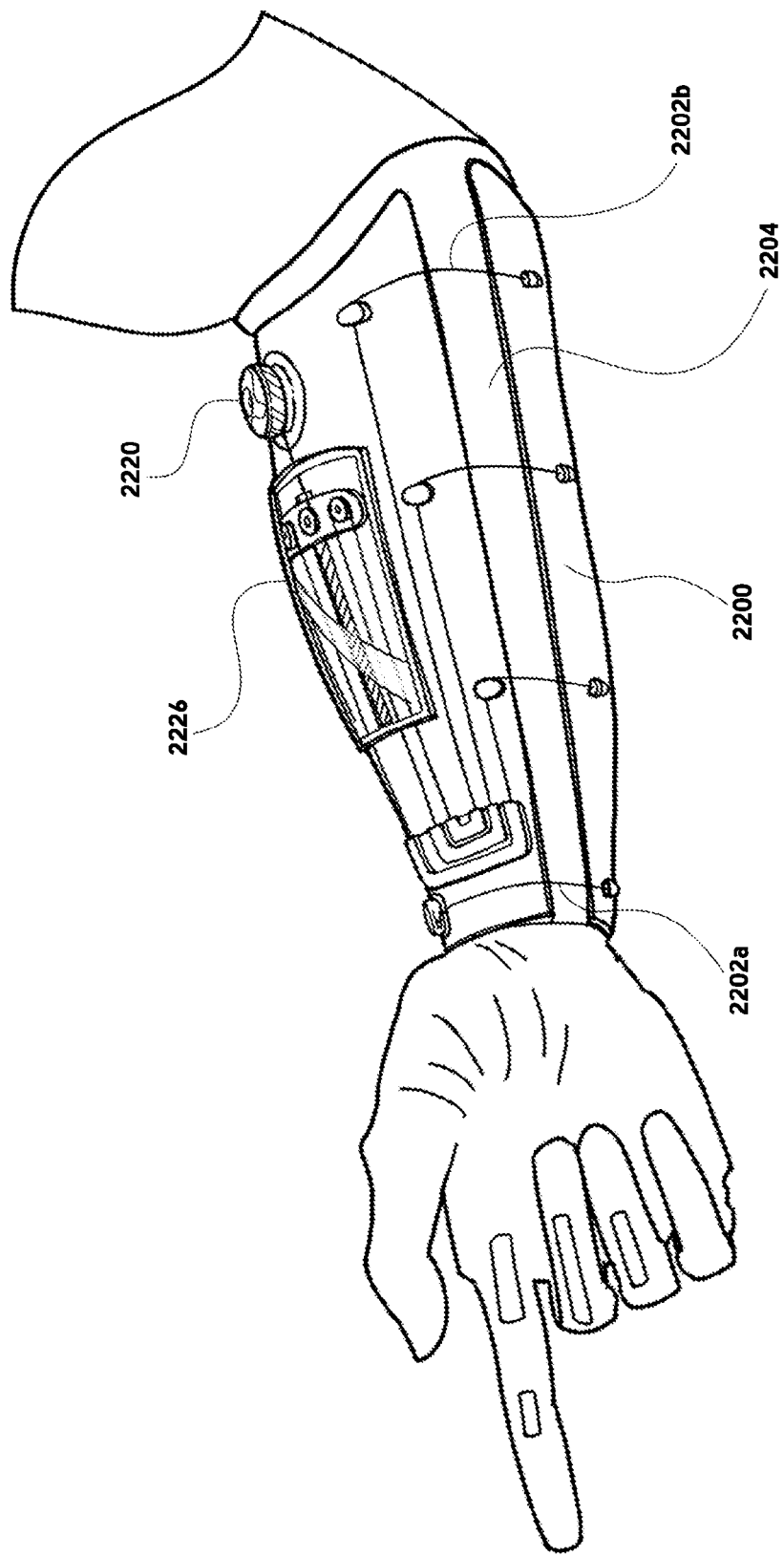
Figure 16B:
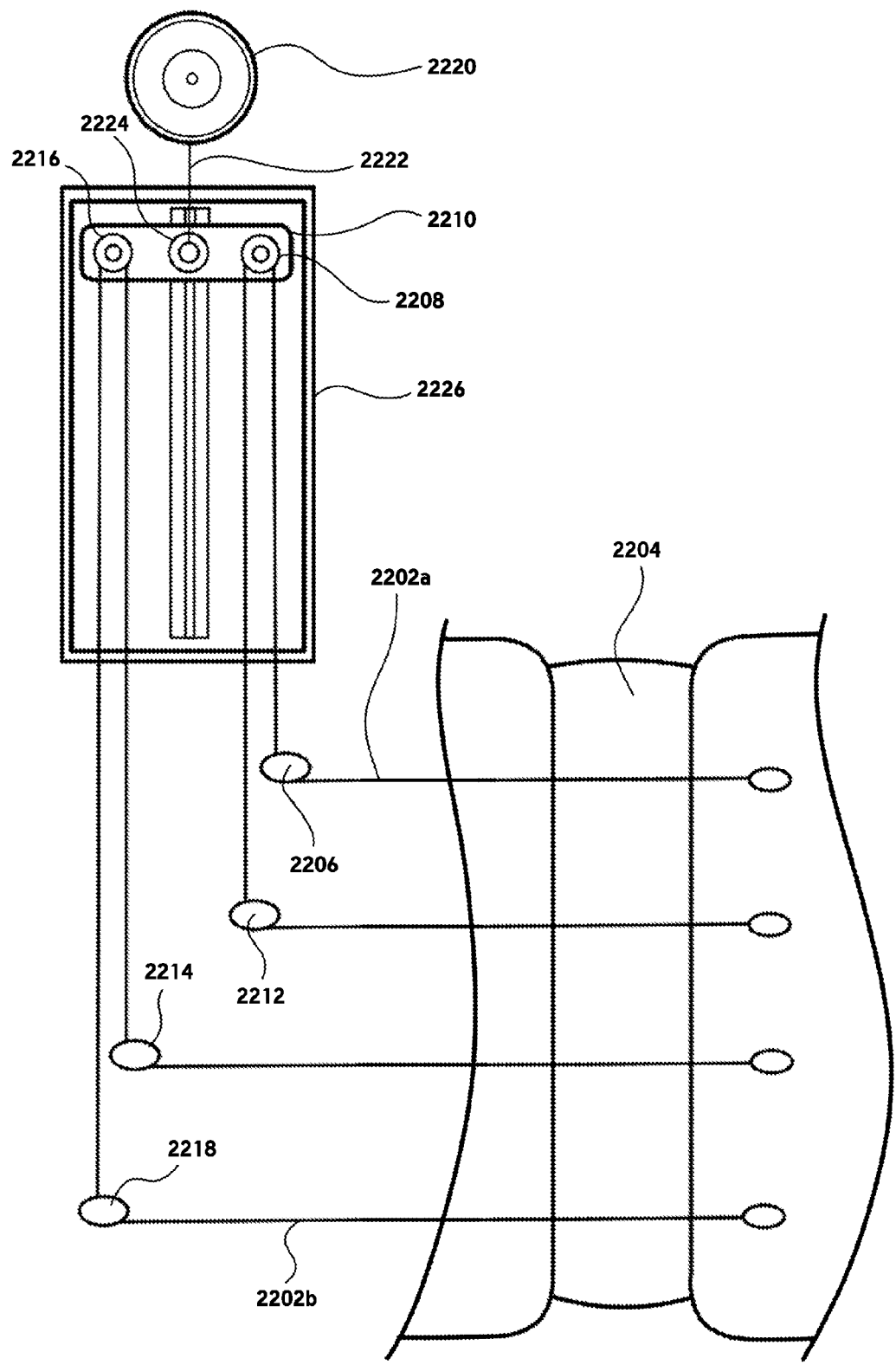

Referring now to FIGS. 16A and 16B, illustrated are other embodiments of tensioning mechanism that may be used to tension a plurality of laces relatively uniformly. Specifically, FIGS. 16A and 16B illustrate an embodiment of a reel based tensioning system that may be used to ensure an equal lace tension is achieved in a plurality of tension members or laces that cross an opening or compression gap 2204 on an article, such as a prosthetic shell 2200. The tensioning mechanism is configured to equalize the tension in each lace during tensioning of the laces. In some embodiments, the tensioning mechanism may also be configured to equalize the tension in each lace subsequent to tensioning of the laces. In other embodiments, the tension of the lace may be locked or set using a lock mechanism (e.g., cam, clamp, ferrule, and the like) after an initial tensioning of the laces so that further tensioning of the laces effects a differential tensioning of the laces. As illustrated in FIGS. 16A and 16B, a pair of laces, 2202*a* and 2202*b*, span the compression gap 2204 with each lace, 2202*a* and 2202*b*, being coupled with a tension or stabilization component 2210 (hereinafter stabilization component 2210) that equalizes the tension in each lace, 2202*a* and 2202*b*. Specifically, a first lace 2202*a* extends from a first side of the prosthetic shell 2200, across gap 2204, around a first post 2206 attached to the prosthetic shell 2200, around a first shaft or pulley 2208 of the stabilization component 2210, around a second post 2212, and back across gap 2204 to a termination point on the first side of the prosthetic shell 2200. Unequal tension in either side of the first lace 2202*a* will result in the first lace 2202*a* sliding around the first pulley 2208 until the tension in the first lace 2202*a* is roughly equalized. In this manner, the first pulley 2208 functions as a first tension equalizer to equalize the tension between a first and second portion of the first lace 2202*a*. The first and second portions of the first lace 2202*a* function essentially as first and second laces or tension members, since each portion of the lace tightens a different portion of the article or brace.

A second lace 2202*b* likewise extends from the first side of the prosthetic 2200, across gap 2204, around a third post 2214 attached to prosthetic shell 2200, around a second pulley 2216 of the stabilization component 2210, around a forth post 2218, and back across gap 2204 to a termination point on the first side of the prosthetic shell 2200. Unequal tension in either side of the second lace 2202*b* will result in the second lace 2202*b* sliding around the second pulley 2216 until the tension in the second lace 2202*b* is roughly equalized. In this manner, the second pulley 2216 functions like the first tension equalizer to equalize the tension between a first and second portion of the second lace 2202*b*. The first and second portions of the second lace 2202*b* function essentially as first and second laces or tension members, since each portion of the lace tightens a different portion of the article or brace.

The stabilization component 2210 is coupled with a reel assembly 2220 via a third lace 2222. As the reel assembly 2220 is operated (e.g., a knob of the reel assembly 2220 rotated) the stabilization component 2210 is pulled toward the reel assembly 2220 to tension the first lace 2202*a* and second lace 2202*b*. The stabilization component 2210 is pivotably coupled with the third lace 2222 via a pin or pivot component 2224 such that unequal tension in the first lace 2202*a* and the second lace 2202*b* causes the stabilization component 2210 to pivot about pin 2224 until the tension in each lace, 2202*a* and 2202*b*, is equalized. In this manner, the stabilization component 2210 functions as a second tension equalizer to equalize the tension between the first and second portions of the first lace 2202*a* and the first and second portions of the second lace 2202*b*. In some embodiments, the stabilization component 2210 may be housed within a clear housing 2226 that is coupled with the prosthetic shell 2200 so that the operation of the stabilization component 2210 is visible to a user.

As shown in FIGS. 16A and 16B, the configuration of the first and second laces, 2202*a* and 2202*b* result in a lace pattern that extends parallel across the compression gap 2204. The parallel arrangement of the laces, 2202*a* and 2202*b*, ensures that the lace tension is directed across the gap to maximize the closure force applied by the laces. Further, the use of multiple laces across the compression gap 2204 increases the closing power applied by reel assembly 2220. FIG. 16A also illustrates a slight variation of the load balancing reel based tensioning system in that the laces, 2202*a* and 2202*b*, or some portion thereof, are slidably positioned within a guide member that is positioned near one end of the prosthetic shell. The use of the guide member allows the laces to be traversed across the gap near the housing 2226.

Figure 17A:
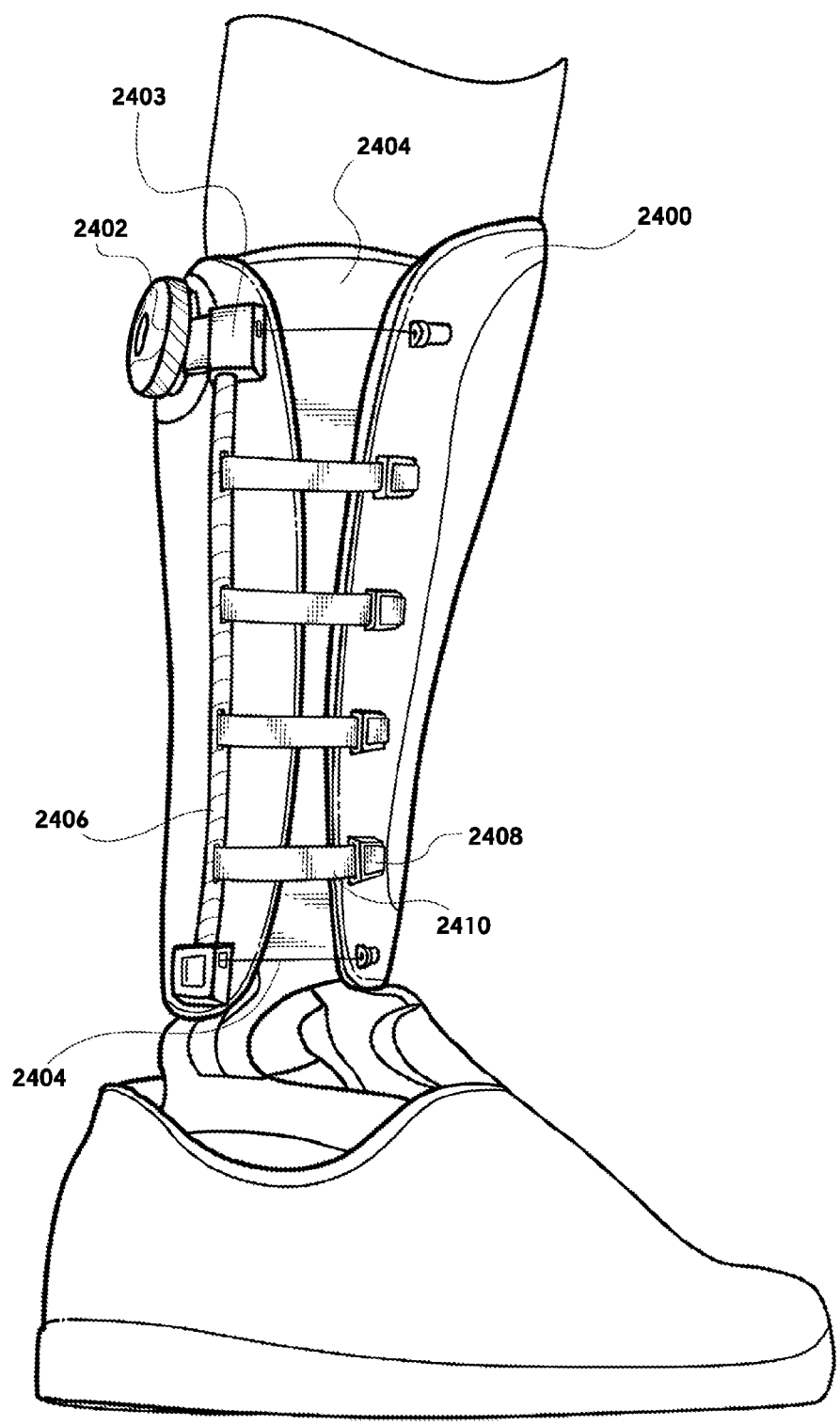
Figure 17B:
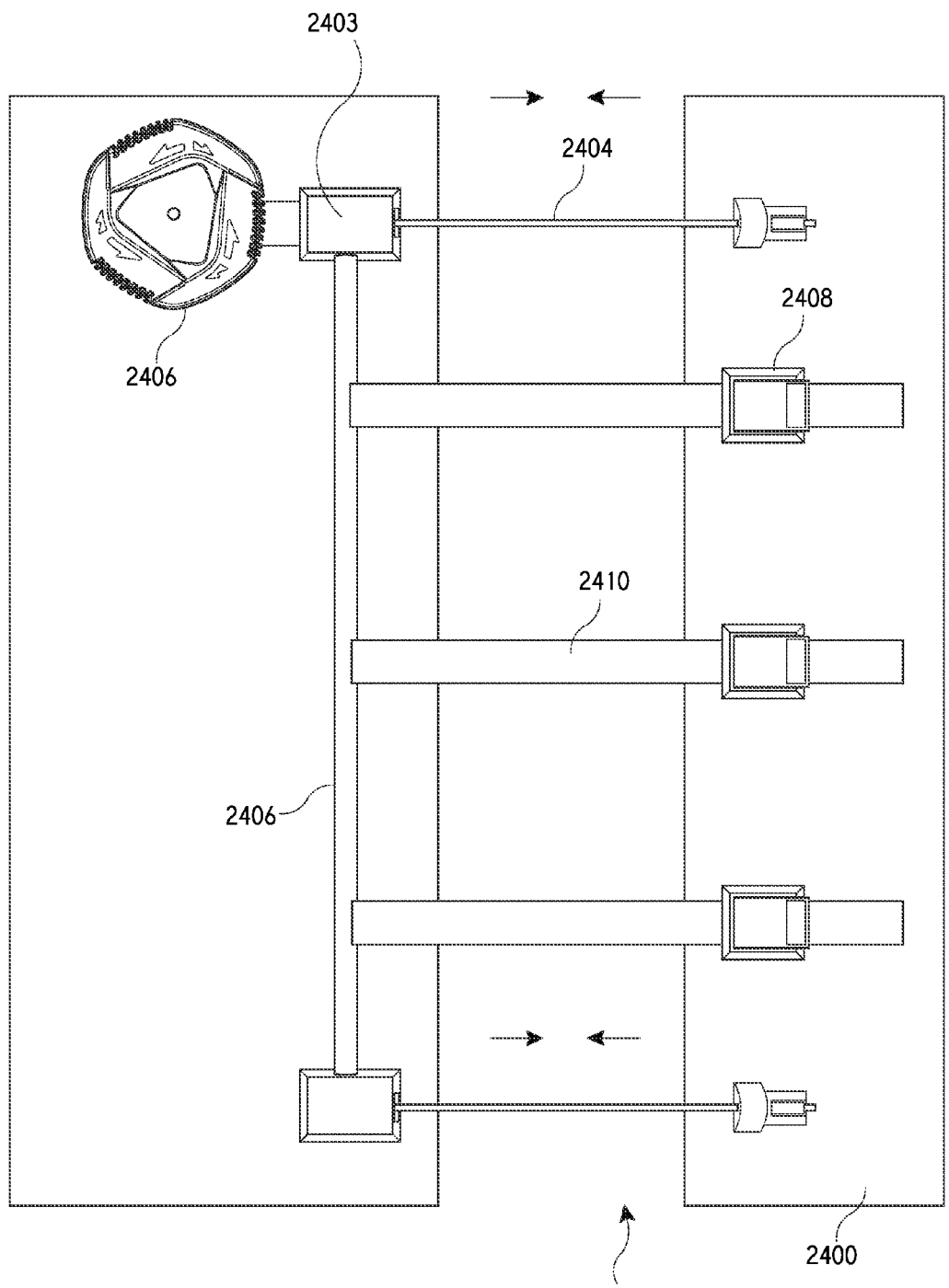
Figure 17C:
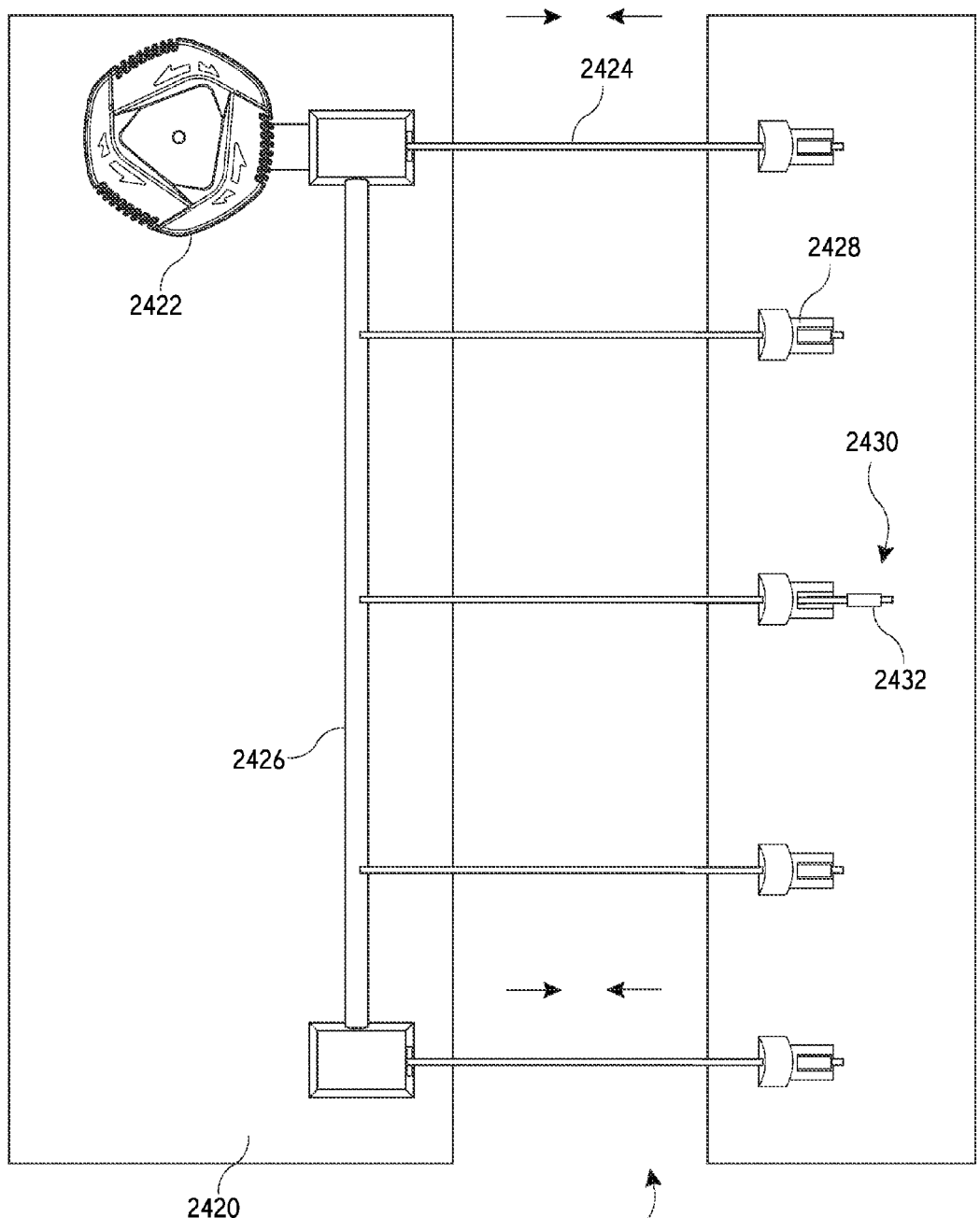

Referring now to FIGS. 17A-C, illustrated are yet other embodiments of elongate members that may be used to tension a plurality of laces relatively uniformly. Specifically, a torsion bar or flexible tensioning shaft may allow a plurality of laces to be approximately equally tensioned. In some embodiments, the length of the laces may be adjusted to allow the torsion bar to apply zonal tightening of the prosthetic shell. FIGS. 17A-C illustrate embodiments of an elongate member, torsion bar, or elongate tensioning shaft 2406 (hereinafter elongate shaft 2406) that may be used to tighten a prosthetic shell 2400. The elongate shaft 2406 extends along the prosthetic shell 2400 and couples with a plurality of tension members that span an opening or gap 2412 of the prosthetic shell 2400. The tension member may be lace 2404, straps 2410, or a combination thereof as shown in FIG. 17B. In some embodiments, the lace 2404 or strap 2410 length from the elongate shaft 2406 to a distal termination point may be adjusted so that tensioning of the lace 2404 or strap 2410 via the elongate shaft 2406 provides a custom zonal fit or tightness. To vary the length, the lace or strap ends may be adjusted and terminated, such as by using a buckle 2408, clamp, cam, lock, and the like. Additional embodiments of adjusting the lace or strap ends are provided in the '773 application, which is incorporated by reference herein.

In some embodiments, the lace 2404 or strap 2410 may be coupled with the elongate shaft 2406 by inserting an end of the lace 2404 or strap 2410 through a slot (not shown) in the elongate shaft 2406. The lace 2404 or strap 2410 may then be wound on itself via rotation of the elongate shaft 2406 about a longitudinal axis of the shaft 2406. Rotation of the elongate shaft 2406 is caused via operation of reel assembly 2402 and/or one or more gear mechanisms 2403. In some embodiments, the flexible tensioning shaft 2406 may run through tubing (not shown) inside or external to the prosthetic shell 2400, or may extend along an outer surface of the prosthetic shell 2400 and be coupled therewith using one or more bearings or locks (not shown).

In some embodiments, the lace 2404 or strap 2410 of one or more zones may be set at a desired tension and the elongate shaft 2406 rotated (e.g., via reel assembly 2402) to differentially tighten the zone or zones. If a different tightness in one or more zones is subsequently desired, the coupling of the lace ends may be adjusted (e.g., via buckles 2408) so as to shorten or length the lace in the desired zones and thereby achieve differential tightness upon subsequent operation of the reel assembly 2402. The lace ends and/or lace length may then be "locked out" so that a desired tension is achieved in the one or more zones.

The buckle 2408 may be used to determine an initial tension and then subsequently "locked out" so that the lace in individual zones are displaced or wound about the elongate shaft 2406 by approximately the same amount. For example, the lace 2404 or strap 2410 may be initially tensioned and each lace 2404 or strap 2410 may be locked in position via buckle 2408 so that additional operation of the reel assembly 2402 winds the laces 2404 or straps 2410 in each zone about the elongate shaft 2406 by roughly the same amount.

As shown in FIG. 17C, an elongate shaft 2426 may extend along a prosthetic 2420 to tension a plurality of zones and reduce a gap 2432. The lace 2424 length from the elongate shaft 2426 to each of the zones may be adjusted so that tensioning of the lace 2424 via the elongate shaft 2426 provides a custom fit. The lace ends 2430 may be adjusted and terminated as described herein, such as by using a slidable lace stop 2432 configured to fit within a recess of a guide 2428. The lace end 2430 can be pulled through the guide 2428 and the lace stop 2432 coupled with the lace to shorten or lengthen the lace between elongate shaft 2426 and guide 2428 and thereby initially tension the lace 2424. The lace 2424 may then be wound on itself via the elongate shaft 2426 and a reel assembly 2422. In some embodiments, the elongate shaft 2426 may run through tubing (not shown) inside or external to the prosthetic 2420, or may extend along an outer surface of the prosthetic 2420 and be coupled therewith using one or more bearings or locks (not shown).

According to one embodiment, a method of configuring an article with a lacing system includes providing a lacing system that includes: a tensioning device, a tensioning mechanism that is operated via the tensioning device, and a plurality of tension members that are coupled with the tensioning mechanism and tensionable thereby. The method also includes coupling the tensioning device with an article and coupling each tension member of the plurality of tension members with the article so that the plurality of tension members are arranged longitudinally about an opening of an article and configured to narrow a gap of the opening upon tensioning of the plurality of tension members in order to tighten the article. As described herein, in such embodiments, the tensioning mechanism is configured so that operation of the tensioning mechanism effects a simultaneous and repeatable tensioning of each tension member of the plurality of tension members to achieve a relatively uniform tightening of the article.

One or more of the tension members may be adjustably coupled with the article so that adjustment of the tension member effects tensioning of the respective tension member upon operation of the tensioning mechanism. The one or more tension members may be adjustably coupled with the article via: an adjustable terminating end, a teeter mechanism, a lock mechanism, a buckle, and the like.

In one embodiment, the tensioning mechanism may be an elongate member that is moveable longitudinally relative to the opening of the article upon operation of the tensioning device. In such embodiments the method may further include coupling each tension member of the plurality of tension members longitudinally along the elongate member. In another embodiment, the tensioning mechanism may be an elongate member that is coupled with the article longitudinally along the opening of the article. In such embodiments, each tension member may be coupled longitudinally along the elongate member and the elongate member may be configured to rotate about a longitudinal axis upon operation of the tensioning device to effect winding of the plurality of tension members about the elongate member. In yet another embodiment, the tensioning mechanism may be configured to equalize the tension in each tension member of the plurality of tension members during and/or subsequent to tensioning of the plurality of tension members. In such embodiments, the tensioning mechanism may include a first means of tension equalization (e.g., a pulley and the like) and a second means of tension equalization (e.g., a pivotable stabilization component and the lie). The first means of tension equalization may effect equalizing the tension between a first and second tension member and the second means of tension equalization may effect equalizing the tension between the a third tension member and the first and second tension members.

In some instances it may be desired to tighten an article via one or more pressure inducing components. For example, it may be desirable to fit a brace about a user's limb via one or more pressure components that apply on inward pressure on the limb. The pressure components may be configured to apply the inward radial pressure via changing a volume of the article. For example, a lacing system for tightening an article about a limb may include: a tensioning device that is coupleable with the article, a tension member that is coupled with the tensioning device and tensionable thereby, and a pressure member that is coupleable with the article. The pressure member may be operable with the tension member and moveable between a first position and a second position relative to the article upon tensioning of the tension member. When the pressure member is in the first position, an opening of the article may have a given surface area. When the pressure member is in the second position, the pressure member may displace into the opening of the article to reduce the surface area and thereby apply inward pressure to the limb. In this manner, the pressure member may effect a volume change of the article to fit the article about the limb.

In another embodiment, a lacing system for tightening an article about a limb may include a tensioning device that is coupleable with the article, a tension member that is coupled with the tensioning device and tensionable thereby, and a pressure member that is coupleable with the article and positionable so that an inner surface of the pressure member faces radially inward relative to an opening of the article. The pressure member is operable with the tension member to displace radially into the opening of the article upon tensioning of the tension member to reduce the opening of the article and thereby apply pressure to the limb.

Figure 13A:
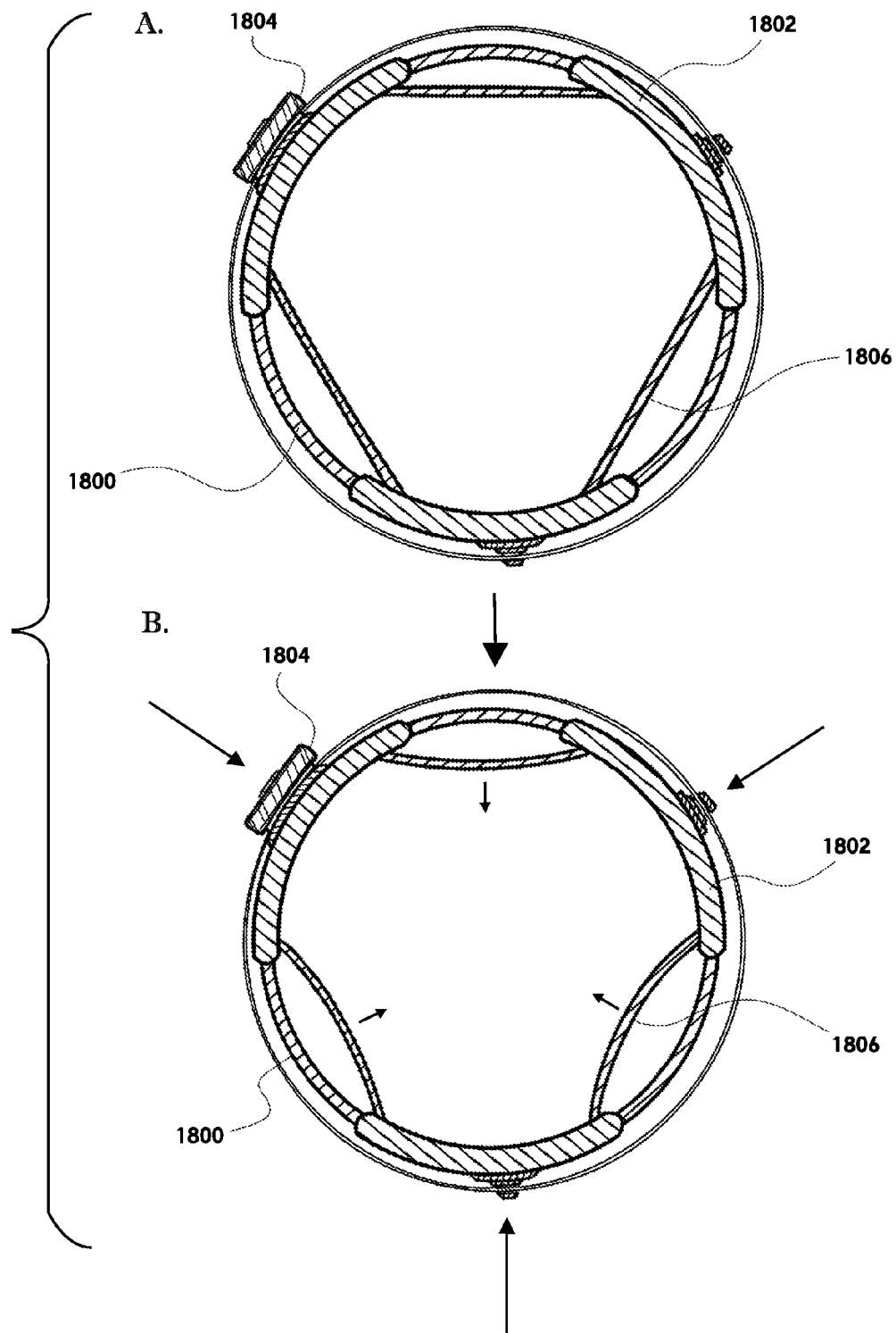

FIGS. 10 and 13A-14D illustrate embodiments of pressure members that function to decrease the effective volume of a prosthetic shell and thereby compress a limb. FIG. 13A illustrates a shell 1800 having multiple pressure or padded members 1802. Pressure or padded members 1802 (hereinafter padded member 1802) are arranged so that an inner surface of the pressure members 1802 faces an opening of the shell 1800. The pressure members can be spaced equidistant from each other as shown in the illustrated embodiment, or can be placed at other intervals as desired to create a desired compression characteristic. A reel based tensioning system 1804 is coupled to the outside of the shell 1800. The reel based tensioning system 1804 is configured to create radial pressure around the shell 1800 by reducing a diameter of the shell 1800 via lace that is positioned around the shell 1800. Specifically, the reel based tensioning system 1804 is configured to reduce a diameter or surface area of the opening of the shell 1800 that is defined by the inner surfaces of the shell 1800 and pressure member. As the radial pressure is increased via reduction in the shell's opening diameter, the padded members 1802 are forced or flexed radially inward. Flex members 1806 may be coupled with the padded members 1802 such that when the padded members 1802 move radially inward, the flex members 1806 bow inwardly. To achieve flexing of the flex members 1806, the flex members 1806 have opposing ends that are coupled or attached to the shell 1800 and a middle portion that is unconnected from the shell 1800. As the flex members 1806 bow inward, the volume within the shell 1800 is decreased and the shell 1800 is compressed around the user's limb. In some embodiments, opposing ends of the flex member 1806 may be fixedly or pivotally coupled with adjacent padded members 1802. In some embodiments, one of the opposing ends of the flex member s1806 may be slidably coupled with the shell 1800 while the other end is fixedly coupled with the shell 1800. Upon tensioning of the tension member, the slidable opposing end may slide toward the fixed opposing end, which causes the middle portion to flex or bow into the opening of the shell 1800 thereby reducing the diameter and/or surface area of the opening.

Figure 13B:
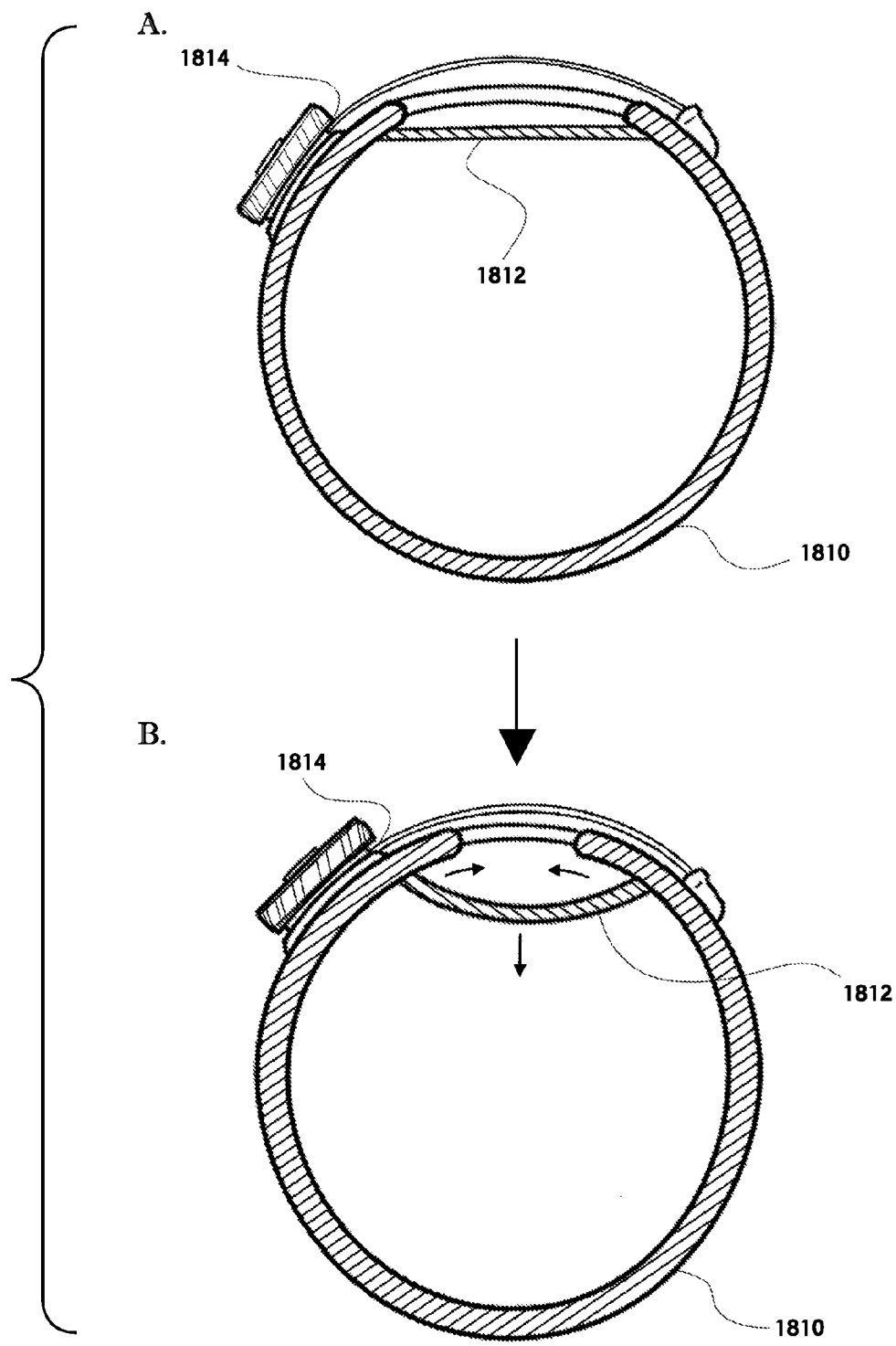

FIG. 13B illustrates another embodiment of a shell 1810 having a flex member 1812. In FIG. 13B, the flex members 1812 is positioned across an opening or gap of the prosthetic shell 1810. A reel based tensioning system 1814 is configured to reduce or close the opening or gap of the shell 1810 and thereby cause the flex member 1812 to flex radially inward to reduce the volume of the shell 1810. Closure of the opening or gap may be effected by spanning lace across the opening or gap and tensioning the lace with a reel assembly as described herein. The flex members, 1806 or 1812, may be configured so that an amount of flexing of the middle portion of the flex members corresponds with an amount of tension that is induced in the tension member. Stated differently, the degree to which the flex members flex or bow into the opening of the respective shell may directly correlate with the tension that is induced in the tension member. As such, infinitesimal amounts of pressure may be applied to the limb via the flex or pressure members.

Figure 13C:
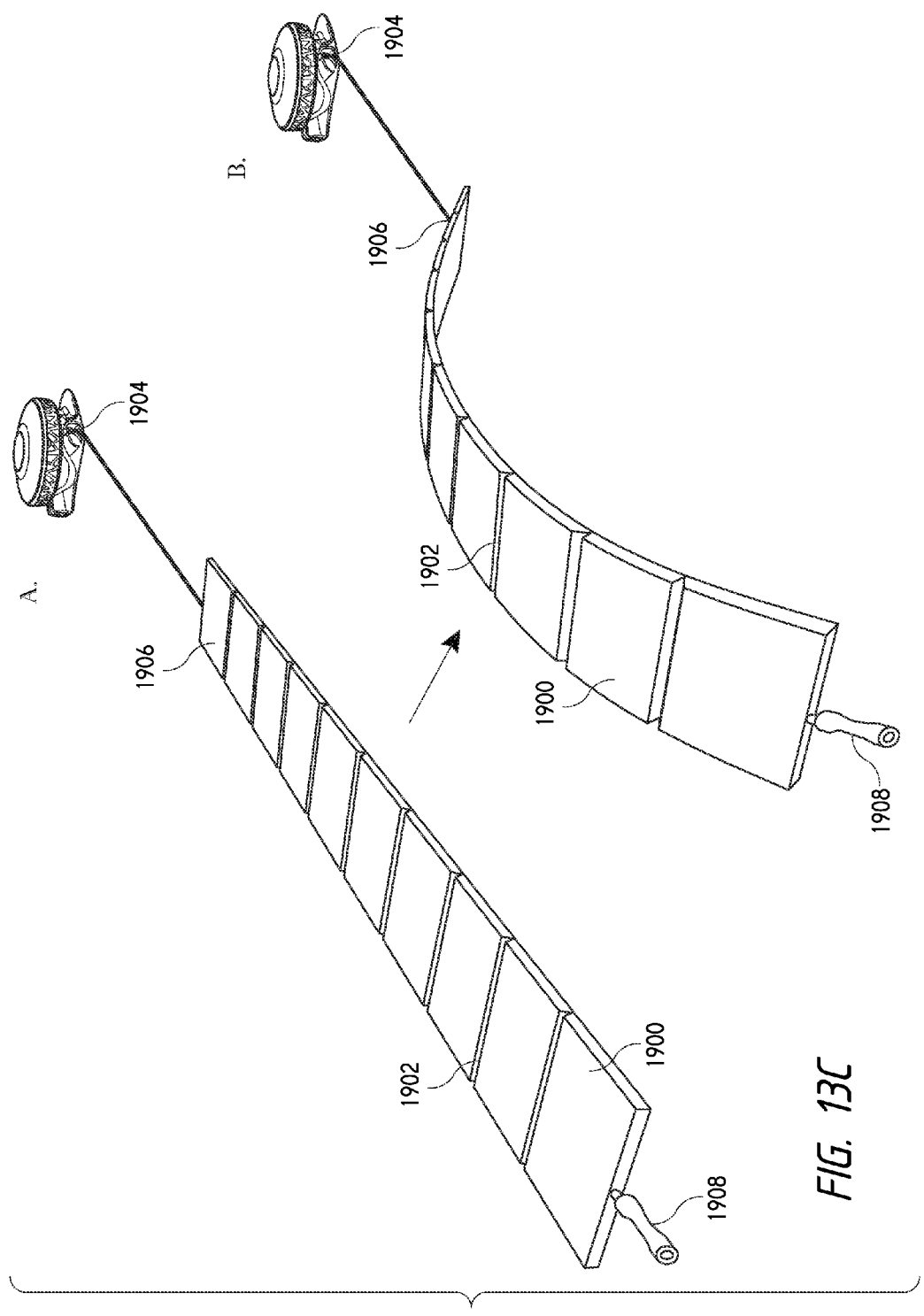

FIG. 13C illustrates an embodiment using a flexible panel 1900 that may be used to decrease a volume of a prosthetic shell. In one embodiment, panel 1900 includes transverse or lateral slits 1902 that are arranged roughly orthogonal to the longitudinal length of the panel 1900. The panel 1900 is coupled with a reel based tensioning system 1904, such as by inserting a plug or stop member through an aperture of a distal end 1908 of the panel. The plug or stop member may contact the distal end 1908 of the panel as the reel based tensioning system 1904 is tightened and thereby compress the panel 1900. The slits 1902 allow the panel 1900 to bend or flex upward as the panel 1900 is compressed. To increase the volume in a shell, a proximal end 1906 of the panel 1900 nearest the reel based tensioning system 1904 can be fixedly secured to the shell. As the reel based tensioning system 1904 is tightened, the unfixed distal end 1908 of the panel 1900 is compressed toward the fixed end 1906, which forces the flexible panel 1900 to bend inward and against a limb positioned within the prosthetic, thereby increasing pressure on the limb.

Figure 14A:
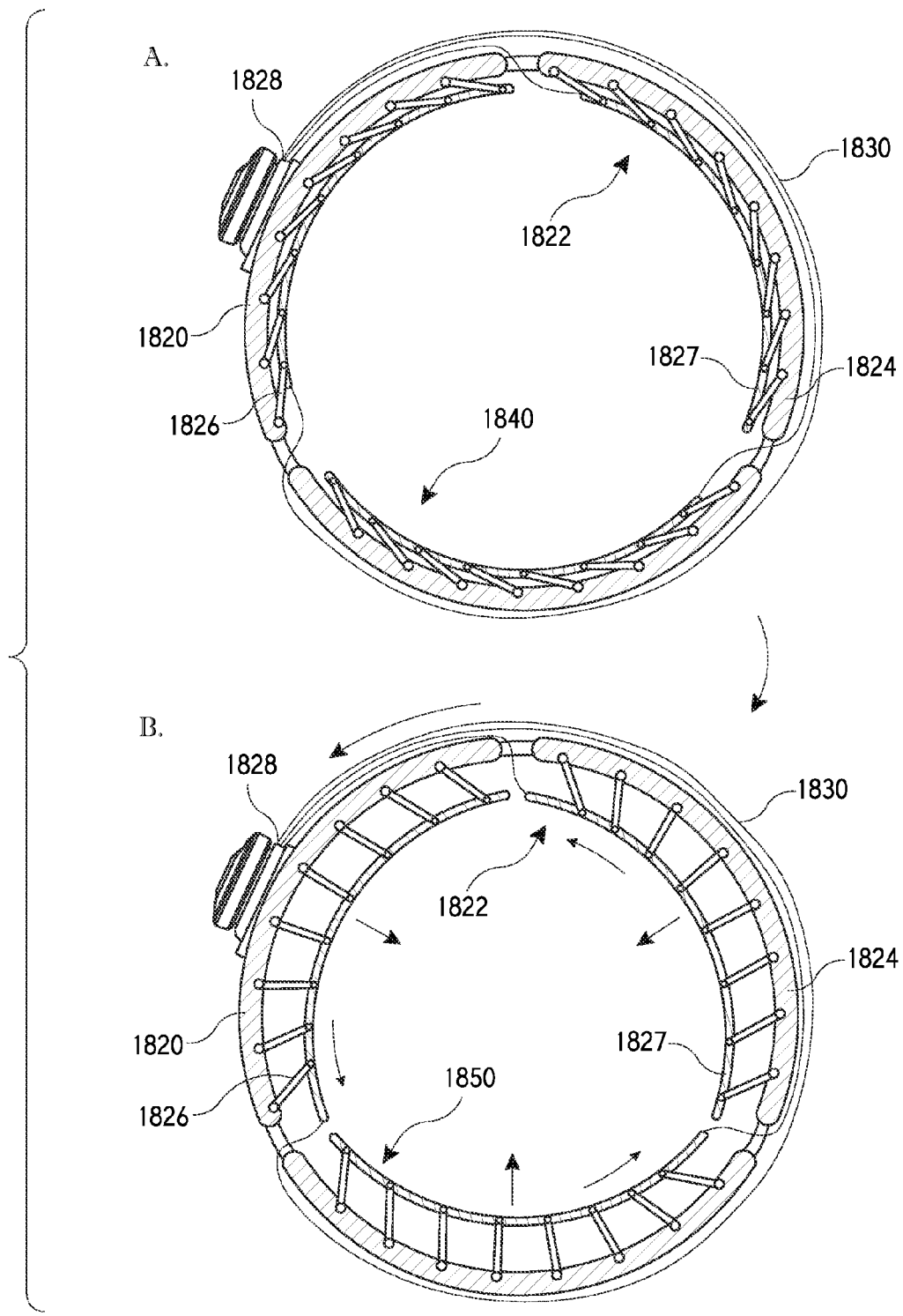

FIGS. 14A-D illustrate another embodiment of a prosthetic shell 1820 utilizing one or more extendable pressure members or panels 1822 (hereinafter pressure panels 1822). The pressure panels 1822 may include two or more parallel rails or members 1824 that are coupled together via multiple connectors 1826. The connectors 1826 may be compliant mechanisms or may be connected to the rails or member 1824 via hinges. The pressure panels 1822 are arranged so that an outer member of the panels 1822 faces an opening of the shell 1820. The pressure panels 1822 create radial pressure on user's limb positioned within the shell 1820 by reducing a diameter or surface area of the opening of the shell 1820 that is defined by the inner surface of the shell 1820 and the outer member of the pressure panels 1822. The pressure panels 1822 reduce the opening's diameter or surface area by the outer member of the pressure panels 1822 moving radially inward into the opening as described herein below. For example, as shown in FIG. 14A, the pressure panel 1822 can be moved between two positions: a collapsed position 1840 in which the parallel members are folded or lie relatively flat against one another, and an extended position 1850, in which the parallel members are offset or displaced away from one another. Displacement of the parallel members increases the volume occupied by the pressure panels 1822. Movement of the two parallel members between the collapsed and extended positions is achieved via the connectors 1826. Additionally, in the extended position 1850, the hinged connectors 1824 are roughly perpendicular relative to the parallel members 1824.

As shown in FIG. 14A, an inner member 1824 of the parallel members of each pressure panel 1822 may be coupled to an inner surface of the shell 1820. A lace of a reel based tensioning system 1828 may be coupled to a proximal end of the outer member 1827 of the parallel members. As the lace of the reel based tensioning system 1828 is tensioned, the proximal end of the outer member 1827 is pulled toward the reel based tensioning system 1828, which causes the pressure panels 1822 to displace into the extended position 1850. This increases the volume occupied by the pressure panels 1822 within the shell 1820 and causes the outer member 1827 to press against a limb positioned within the shell 1820.

Figure 14B:
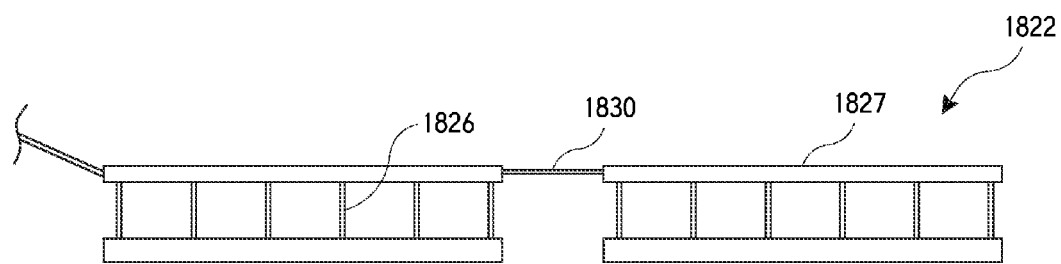
Figure 14C:
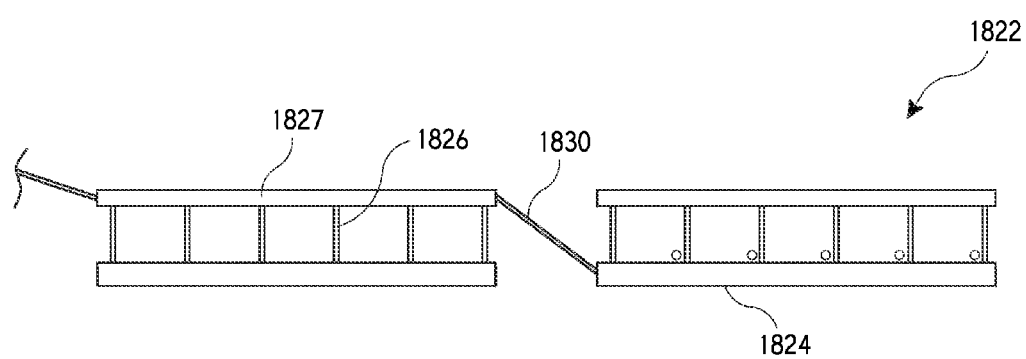
Figure 14D:
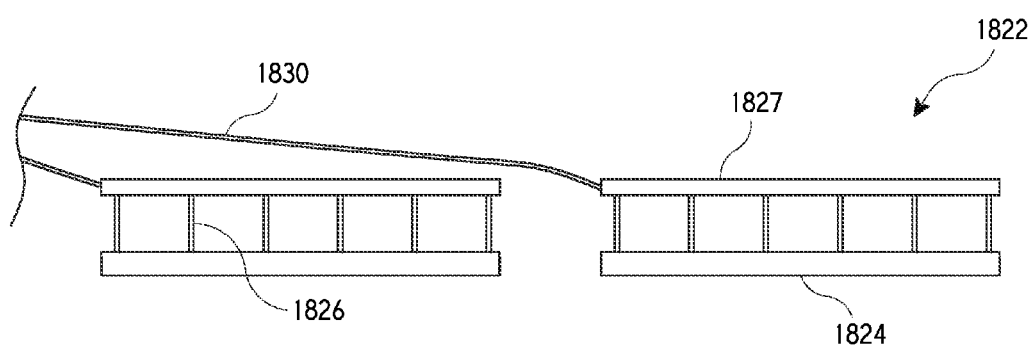

FIGS. 14B-D illustrate the pressure panels 1822 being coupled with the reel based tensioning system 1828 in a variety of ways. For example, a single lace 1830 may be threaded through the outer member 1824 such that as the lace 1830 is tensioned, each pressure panel 1822 displaces or moves at the same rate. In another embodiment, a first lace 1830 may be coupled with a proximal end of an outer member 1827 of a first pressure panel while a second lace is coupled with a distal end of the first pressure panel's outer member and with a proximal end of an inner member of a second pressure panel that is positioned distally of the first pressure panel. The second lace may cause the inner member to move proximally relative to the outer member of the second pressure panel, which causes the pressure panel to radially expand as previously described. In yet another embodiment, the pressure panels 1822 may each be coupled with a separate lace 1830 that is in turn coupled with the reel based tensioning system 1828. In such an embodiment, the pressure panels 1822 can be configured to extend at the same rate, or the length of lace 1830 to one or more of the pressure panels 1822 can be varied to a vary the rate at which one or more pressure panels extend. The outer and inner members of the pressure panels 1822 are configured so that an amount of movement of the outer member 1827 relative to the inner member 1824 and inward into the opening of the shell 1820 corresponds with an amount of tension that is induced in the tension member. Stated differently, the degree to which the outer member 1827 moves relative to the inner member 1824 and into the opening of the shell 1820 is directly correlated with the tension that is induced in the tension member. As such, infinitesimal amounts of pressure may be applied to the limb via the pressure panels be tensioning the tension members to a given degree.

Figure 10:
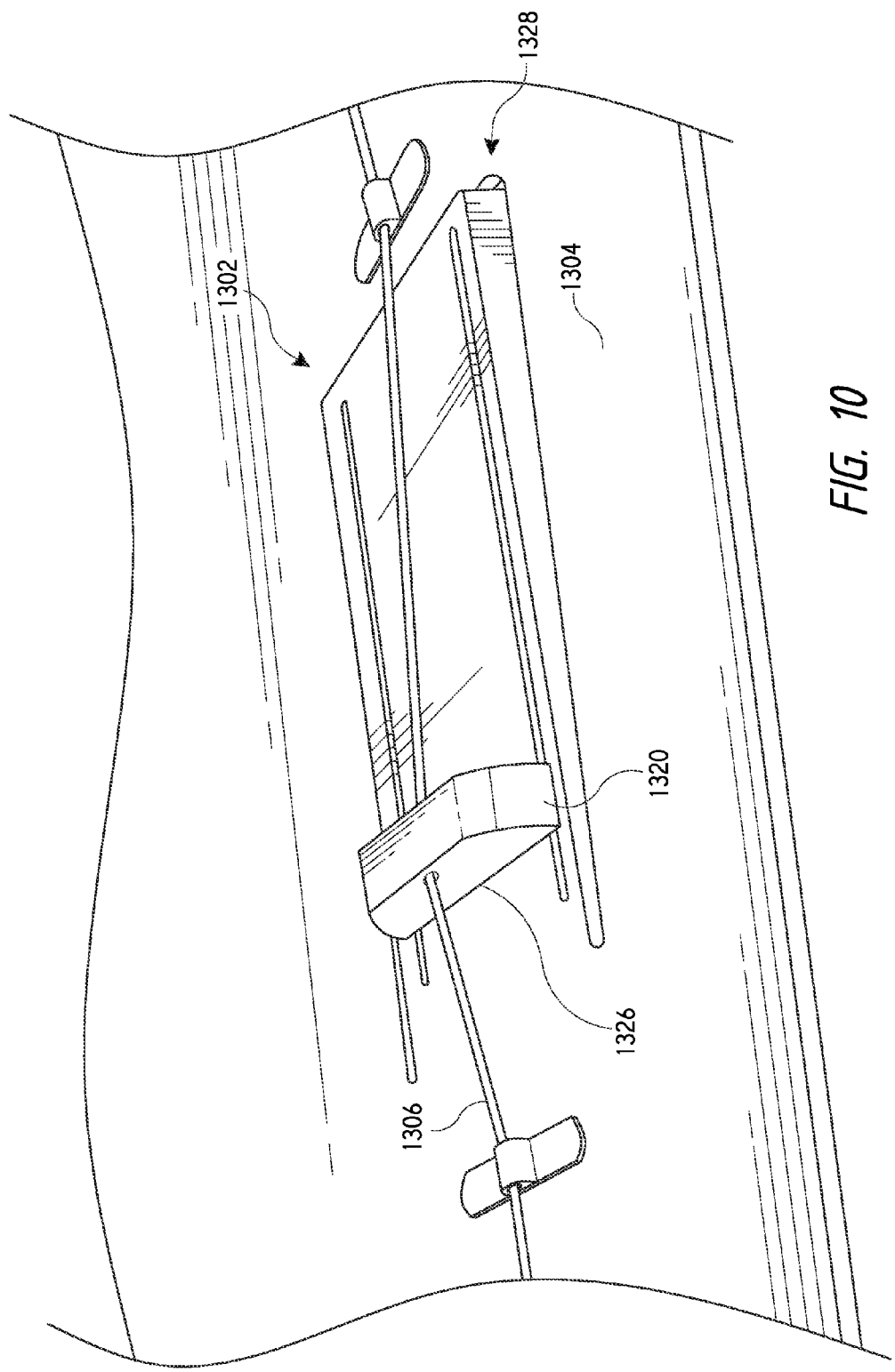
FIGS. 10 and 13A-14D illustrate embodiments of pressure members that function to decrease the effective volume of a prosthetic shell and thereby compress a limb.

In some embodiments, pressure applied to a limb by a prosthetic shell may be adjusted by altering a position of a guide. In FIG. 10, a second member or guide 1320 is positioned on a first member or wedge shaped pressure member 1302, for example at a distal end of the wedge member 1302. As a lace 1306 is tensioned, the guide 1320 forces the distal end of the wedge member 1302 downward towards an outer surface of the shell 1304. An inner surface of the wedge member 1302 is pressed inward and into contact with the limb, or into contact with cushioning or some other component that is positioned adjacent the limb, thereby increasing the pressure of the shell 1304 about the limb. In some embodiments, the amount of pressure applied to the limb by the wedge member 1302 may be adjusted by altering the position of the guide 1320 relative to the wedge member 1302. For example, guide 1320 can be slidably positioned on a track that enables the guide 1320 to be moved and positioned along the wedge member 1302. For example, guide 1320 can be positioned near a proximal end 1326 of the wedge member 1302 to minimize the amount of pressure applied when a lace 1306 is tensioned, or guide 1320 can be moved toward a distal end 1328 of the wedge member 1302 to increase the amount of pressure applied to the limb upon tensioning of the lace 1306. Sliding of the guide 1320 from the proximal end to the distal end of the wedge member 1302 causes a greater displacement of the wedge member 1302 inward into the opening of the shell 1304. The greater displacement inward of the wedge member 1302 is achieved via the wedge shape of the wedge member 1302. Positioning the guide 1320 over the large wedge portion of the wedge member 1302 forces a greater displacement of the wedge member 1302 into the opening of the shell 1304. The wedge shape of the wedge member 1302 and the movement of the guide 1320 along the wedge member 1302 enables infinitesimal amounts of pressure to be applied to the limb.

In some embodiments, the guide member 1320 and wedge member 1302 may be arranged so that an inner surface of the wedge member 1302 faces an opening of the shell 1304. The wedge member 1302 creates radial pressure on user's limb positioned within the shell 1304 by reducing a diameter or surface area of the opening of the shell 1304. The wedge member 1304 reduces the opening's diameter or surface area by the inner surface of the wedge member 1304 moving radially inward into the shell's opening.

In some embodiments, the lace may be coupled with a movable component so that tensioning of the lace (e.g., via a reel based tensioning system) causes the movable component to slide along a track and against a wedge member. In such embodiments, the pressure exerted on the limb via the wedge member may be dynamically adjusted as the lace is tensioned or loosened via reel based tensioning system.

According to one embodiment, a method of configuring an article with a lacing system includes providing a lacing system that includes: a tensioning device, a tension member that is coupled with the tensioning device and tensionable thereby, and a pressure member. The method also includes coupling the tensioning device with the article and coupling the pressure member with the article so that an inner surface of the pressure member faces radially inward relative to an opening of the article. The pressure member is operable with the tension member so that the pressure member displaces radially into the opening of the article upon tensioning of the tension member. Displacement of the pressure member into the opening reduces the opening of the article and thereby applies pressure to a limb positioned with the article.

In some embodiments, coupling the pressure member with the article includes coupling opposing ends of the pressure member with the article while a middle portion of the pressure member remains uncoupled from the article. In such embodiments, tensioning of the tension member causes the middle portion of the pressure member to flex radially inward into the opening of the article. In such embodiments, one of the opposing ends of the pressure member may be slidably coupled with the article while the other opposing end is fixedly coupled with the article. In such embodiments, the slidable opposing end may slide towards the fixed opposing end upon tensioning of the tension member.

In another embodiment, the pressure member may include a first member and a second member that is moveably coupled with the first member. In such embodiments, tensioning of the tension member may cause the second member to move relative to the first member and radially into the opening of the article. In such embodiments, the pressure member may also include a third member that couples the second member with the first member and effects movement of the second member radially into the opening of the article upon tensioning of the tension member.

In another embodiment, coupling the pressure member with the article may include slidably coupling a second member with a first member so that the second member is slidable between a proximal end and a distal end of the first member. In such embodiments, sliding of the second member from the proximal end to the distal end of the first member causes the first member to displace into the opening of the article. In such embodiments, the first member may include a tapered configuration between the proximal and distal ends so that sliding of the second member along the tapered configuration of the first member effects an increased amount of displacement of the first member radially into the opening of the article.

Figure 15:
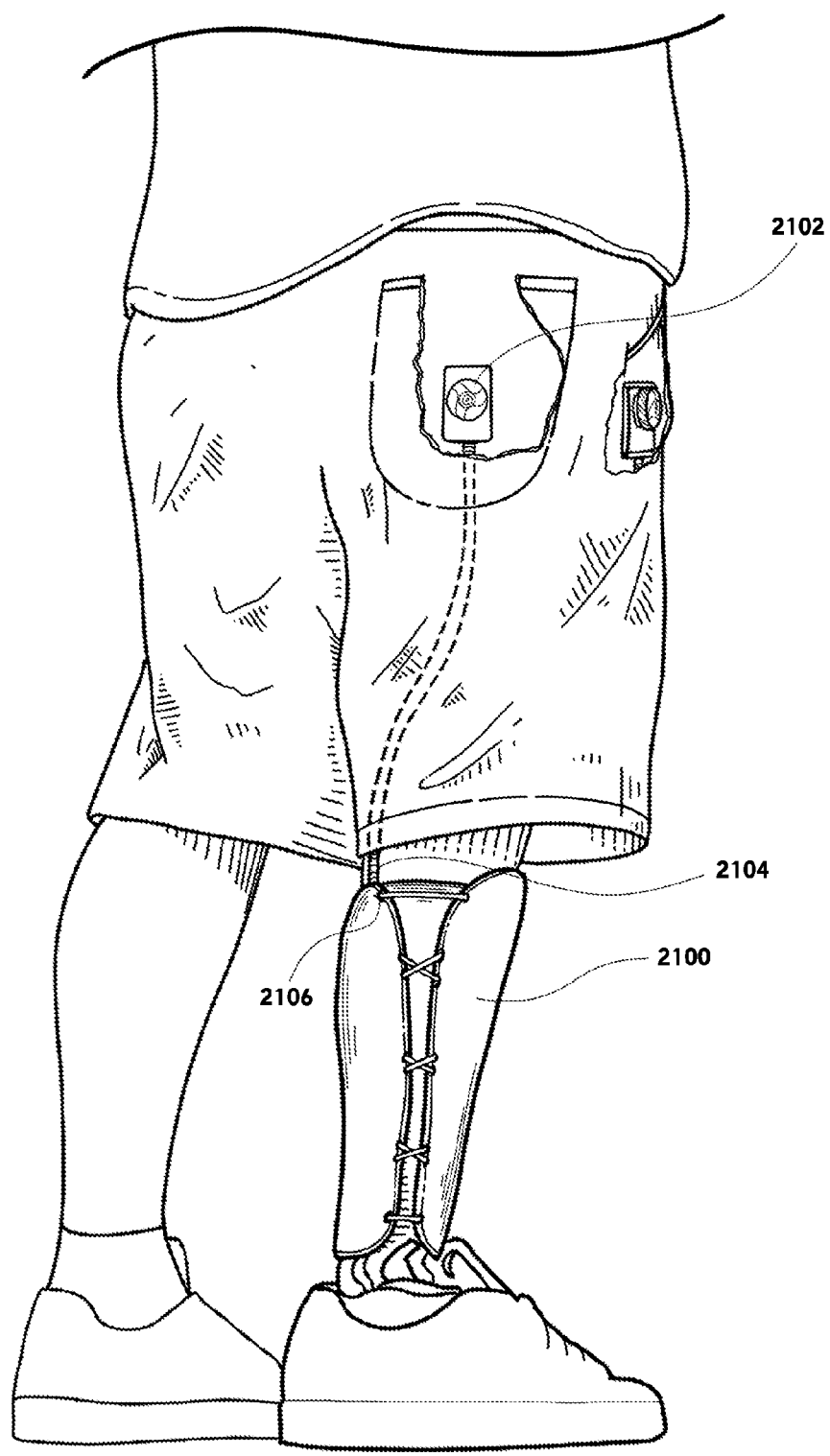
FIG. 15 illustrates an embodiment of a reel assembly or tightening mechanism that may be remote from and/or repositioned relative to a prosthetic shell, such as for easier access to a user and/or to provide a desired visual appeal.

As shown in FIG. 15, in some embodiments it may be desirable to move the location of a reel assembly or tightening mechanism 2102 relative to the prosthetic shell 2100. For example, the tightening mechanism 2102 may be moved for easier access to the user or to provide the prosthetic shell 2100 with a desired visual look. In one embodiment, the tightening mechanism 2102 can be positioned within a pocket of the user's pants. The position of the tightening mechanism 2102 allows the user to easily access the tightening mechanism 2102 to tighten or loosen the prosthetic shell 2100. Non-compressible tubing 2104 may extend from the tightening mechanism 2102 to a tightening component 2106 that is coupled with the prosthetic shell 2100 to tension or loosen the reel based tensioning system's lace. In some embodiments, the prosthetic shell 2100 may include a tensioning mechanism 2102 that is removably couplable and operable with the tightening component 2106 to tension or loosen the reel based tensioning system's lace upon actuation of the tightening mechanism 2102. In such embodiments, the tightening component 2106 is removable from the tensioning mechanism 2102 such that the tightening mechanism 2102 may be removed when it is not in use. The tightening component 2106 may include a cylindrical drive mechanism that is placed on top of a reel assembly (i.e., the tensioning mechanism 2102). The tensioning mechanism 2102 may provide the prosthetic shell 2100 with a relatively low profile appearance that may be visually pleasing to consumers. In some embodiments, the tensioning mechanism 2102 may be positioned within the prosthetic shell 2100 and the tightening component 2102 may include a plug (not shown) that is inserted within the prosthetic shell 2100 to operate with tightening mechanism 2102. The tightening component 2102 may be removably or nonremovably coupled with the user's pants via stitching, adhesive bonding, snaps, mechanical, fasteners, Velcro®, and the like. In still other embodiments, the tightening mechanism 2102 may be positioned elsewhere on the user's pants or clothing, such as a belt and the like.

Although the above figures illustrate the prosthetic devices being closed via manual reel based tensioning systems, it should be realized that the manual reel based tensioning systems described in the various embodiments could be replaced with motorized devices that tension the lace and/or tighten the prosthetic about the limb. It some instances it may be beneficial to replace the manual reel based tensioning systems with motorized devices and/or control systems. For example, the motorized devices/control systems may allow for more precise lace tension monitoring, prosthetic pressure monitoring, real time lace tension adjustment, and the like. The motorized devices/control systems may also be programmed to monitor various prosthetic and/or lace tension conditions and to provide various feedback based on the monitored conditions, such as overtensioning, over pressurization, excess heat, excess wear on the limb, and the like. The activity and/or condition of the limb may also be monitored and provided to user and/or a physician as desired. Audible alarms may be triggered when potential problems are detected. In addition, the motorized devices/control systems may be used for various other purposes.

Figure 18A:
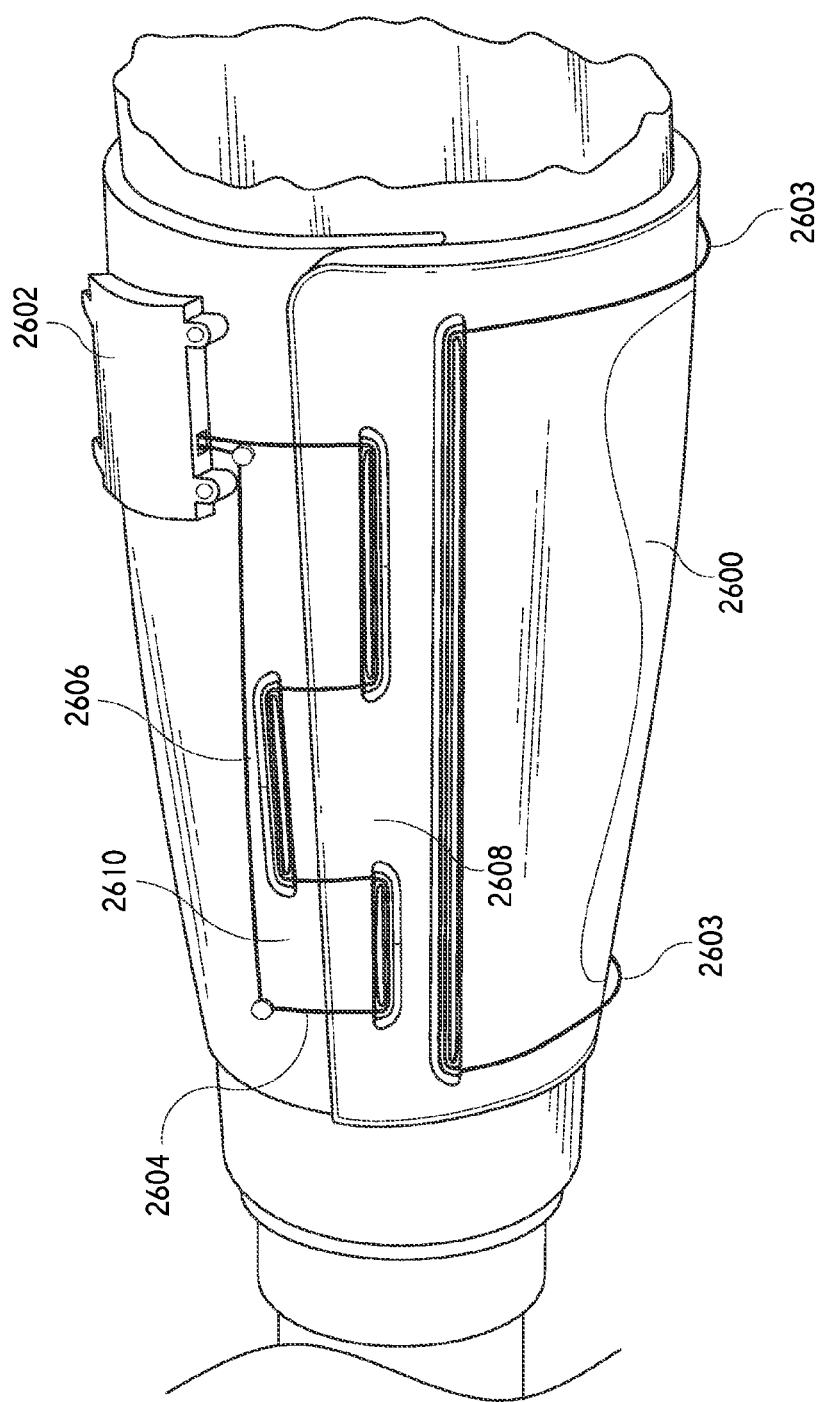

FIGS. 18A-C illustrate a motorized tensioning system 2602 that may be used used to open and close a prosthetic device 2600. The tensioning system 2602 includes a motorized reel assembly 2602 that includes a stacked spool, which may be similar to that described in the '773 application incorporated by reference herein. Each spool is coupled with a lace and the two laces 2604 and 2603 are wound in opposite directions. When the spool winds in a first direction, the spool draws in a first lace 2604 guided by guides 2606 and arranged along a first lace path, which closes a gap 2612 and tightens the prosthetic device 2600 about a limb. Stated differently, tensioning of the first lace 2604 draws a proximal side 2610 of the gap 2612 toward to a distal side 2608 of the gap 2612. Winding of the spool in the first direction also causes a second lace 2603 to release or loosen. The second lace 2603 may be arranged along a second lace path, which in the illustrated embodiment is circumferentially around the prosthetic device's body.

When the spool is wound in a second direction, opposite the first direction, the second lace 2603 is drawn in or wound around the spool and tightened while the first lace 2604 is released or loosened. Loosening of the first lace 2604 allows the gap 2612 to be opened, which occurs due to tension in the second lace 2603. Because the second lace 2603 is positioned circumferentially around the prosthetic device's body, tension of the second lace 2603 functions to pry open the gap 2612 of the prosthetic device 2600. The user may then easily remove the prosthetic device 2600 from about the limb.

FIG. 18C shows a plan view of the motorized tensioning device 2602 and the first and second lace paths. As illustrated, a first lace 2604 exits the motorized tensioning device 2602 and is guided (via guides 2606) across the gap or opening 2612 approximately four times. The distal end of the first lace 2604 then returns to the motorized tensioning device 2602 and is coupled with an internal spool (not shown) of the motorized tensioning device 2602. Because both ends of the first lace 2604 are coupled with the motorized tensioning device's spool and the lace 2604 crosses the opening or gap 2612 four times, the resulting shortening or lengthening of the lace 2604 upon operation of the motorized tensioning device 2602 is approximately $\Delta\frac{1}{2}$ (i.e., 4 lace crossings per 2 ends of the lace being tensioned). The second lace 2603 exits an opposite side of the motorized tensioning device 2602 and is guided across the distal side 2608 of the brace 2600 approximately twice. The distal end of the second lace 2603 terminates near the opening or gap 2612. Because only a single end of the second lace 2603 is coupled with the motorized tensioning device's spool and the second lace 2603 crosses the distal side 2608 twice, the resulting shortening or lengthening of the second lace 2603 upon operation of the motorized tensioning device 2602 is also approximately $\Delta\frac{1}{2}$ (i.e., 2 lace crossings per 1 ends of the lace being tensioned). Because the shortening or lengthening of the first lace 2604 and second lace 2603 is approximately $\Delta\frac{1}{2}$ upon operation of the motorized tensioning device 2602, operation of the motorized tensioning device 2602 in the first direction or the second direction results in an approximately equal amount of the first or second lace being ejected or wound within the motorized tensioning device 2602. As such, undue slack is not created in either the first or second lace upon tightening or loosening of the brace from about a user's limb. It should be realized that the lace configurations of FIG. 18A-C may vary depending on the desired closure and/or application of the brace and/or for any other reason. Regardless of the lace path used, the first and second lace paths may be configured so that the shortening and lengthening of the first and second laces are approximately equal. Further, the lace paths of a third lace, fourth lace, and the like, may likewise be configured so that shortening and lengthening of all the laces is approximately equal. Such embodiments ensure that undue slack is not created in any lace, which may negatively affect the operation of the motorized tensioning device 2602 and/or brace closure.

Figure 18D:
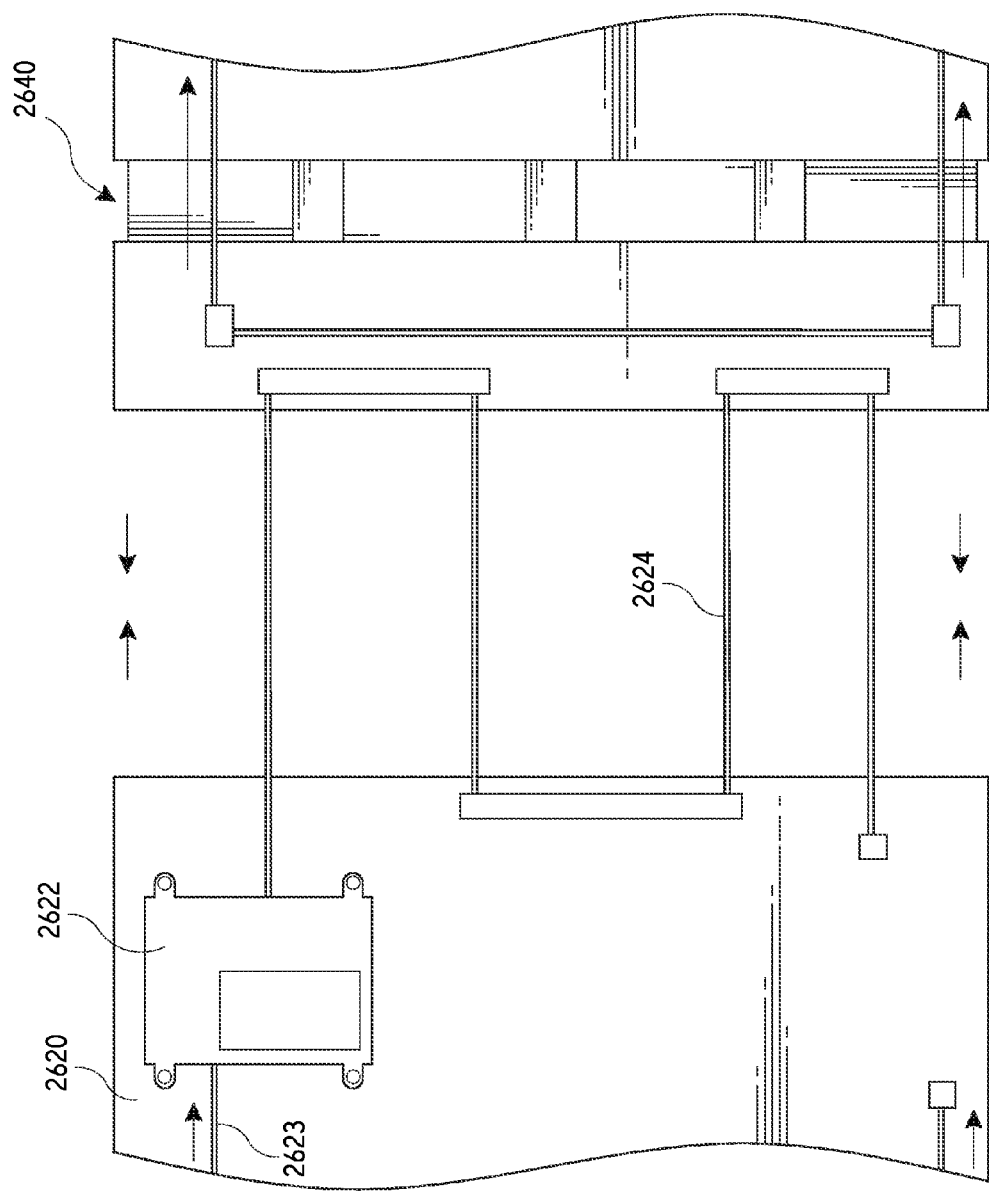
FIG. 18D illustrates a tensioning system that includes a component that compensates for a difference in the shortening or lengthening of different laces due to lace path configurations.

FIG. 18D illustrates an embodiment in which the brace 2620 may include a component that compensate for any difference in the shortening or lengthening of different laces due to a lace path. Specifically, a first lace 2624 exits a motorized tensioning device 2622 and crosses an opening 2632 of the brace 2620 four times. Only a single end of the first lace 2624 is tensioned via the motorized tensioning device 2622 so that the resulting shortening/lengthening of the first lace 2624 upon operation of the motorized tensioning device 2602 is approximately Δ¼. A second lace 2623 exits the motorized tensioning device 2622 and crosses a distal side of the brace 2620 twice. A single end of the second lace 2623 is tensioned via the motorized tensioning device 2622 so that the resulting shortening/lengthening of the second lace 2623 upon operation of the motorized tensioning device 2622 is approximately Δ½. The lace paths of FIG. 18D result in differential shortening/lengthening of the first and second laces, 2624 and 2623. To compensate for the differential shortening/lengthening of the laces, the brace includes a spring component 2640 that resiliently lengthens and shortens due to the difference in lengthening or shortening of the first and second laces, 2624 and 2623. The spring component 2640 maintains a nominal level of tension in the first and second laces upon operation of the motorized tensioning device 2622. In other embodiments, the spring component 2640 may be coupled with the first or second lace, 2624 or 2623, instead of being coupled with the brace 2620. Although the embodiments of FIGS. 18A-D are illustrated as employing a motorized tensioning device, in other embodiments a manual device, such as those described previously, may be used to open or close the brace. In such embodiments, the lace configurations described in FIGS. 18A-D may be employed.

As a general summary of the embodiments of FIGS. 18A-D, a brace, or lacing system for a brace, may include a tensioning device having a first mode of operation and a second mode of operation, a first tension member or lace that is coupled with the tensioning device and tensionable thereby to effect tightening of the brace about the limb, and a second tension member or lace that is coupled with the tensioning device and tensionable thereby to effect opening of the brace from about the limb. The tensioning device may be configured so that: operating the tensioning device in the first mode of operation effects tensioning of the first tension member to close and tighten the brace about the limb and operating the tensioning device in the second mode of operation effects tensioning of the second tension member to loosen and open the brace from about the limb. The tensioning device may also be configured so that: operating the tensioning device in the first mode of operation effects loosening of the second tension member while simultaneously tensioning the first tension member and operating the tensioning device in the second mode of operation effects loosening of the first tension member while simultaneously tensioning the second tension member. The first mode of operation and the second mode of operation of the tensioning device may be effect winding of the spool in opposite directions as previously described.

In some embodiments, the first tension member may be routed about the brace along a first path that is configured to close and tighten the brace upon tensioning of the first tension member, and the second tension member may be routed about the brace along a second path that is configured to open and loosen the brace upon tensioning of the second tension member. In such embodiments, the first path and the second path may be configured so that an amount of displacement of the second tension member about the second path is proportional or equivalent to an amount of displacement of the first tension member about the first path. In some embodiments, the tensioning device may be a reel based closure system having a knob that is rotatable in a first direction and a second direction. In such embodiments, rotation of the knob in the first direction corresponds to the first mode of operation and rotation of the knob in the second direction corresponds to the second mode of operation.

In other embodiments, the tensioning device may be a motorized device having an internal mechanism (e.g., electric motor, spool, etc.) that effects tensioning of the first tension member and simultaneous loosening of the second tension member in the first mode of operation, and that effects tensioning of the second tension member and simultaneous loosening of the first tension member in the second mode of operation. In such embodiments, the brace may further include a control unit that is communicatively coupled with the motorized tensioning device. The control unit may be configured to: receive a first input and communicate a first instruction to the motorized tensioning device to effect operation of the motorized tensioning device in the first mode of operation. The control unit may be further configured to: receive a second input and communicate a second instruction to the motorized tensioning device to effect operation of the motorized tensioning device in the second mode of operation.

According to an embodiment, a method for automatically opening and closing a brace about a limb is provided. The method is used for a brace that includes a tensioning device having a first mode of operation and a second mode of operation. The brace also includes a first tension member or lace that is coupled with the tensioning device and tensionable thereby to effect tightening of the brace about the limb. The method includes operating the tensioning device in the first mode of operation, which effects tensioning of the first tension member to close and tighten the brace about the limb. The method also includes operating the tensioning device in the second mode of operation, which effects loosening of the first tension member and effects opening of the brace from about the limb.

In some embodiments, the brace includes a second tension member or lace that is coupled with the tensioning device and is tensionable thereby to effect opening of the brace from about the limb. In such embodiments, operating the tensioning device in the second mode of operation effects tensioning of the second tension member while loosening the first tension member. The second tension member is coupled with the brace so that tensioning of the second tension member loosens and opens the brace from about the limb. In such embodiments, the first tension member is routed along a first path about the brace that is configured to close and tighten the brace upon tensioning of the first tension member, and the second tension member is routed along a second path about the brace that is configured to open and loosen the brace upon tensioning of the second tension member.

As described above, the first path and the second path of the respective tension members are configured so that an amount of displacement of the second tension member about the second path is proportional or equivalent to an amount of displacement of the first tension member about the first path. In some embodiments, the tensioning device may be a reel based closure system having a knob that is rotatable in a first direction and a second direction. In such embodiments, rotation of the knob in the first direction corresponds to the first mode of operation of the tensioning device and rotation of the knob in the second direction corresponds to the second mode of operation of the tensioning device.

In other embodiments, the tensioning device may be a motorized device having an internal mechanism (e.g., electric motor, spool, etc.) that effects tensioning of the first tension member and simultaneous loosening of the second tension member in the first mode of operation and that effects tensioning of the second tension member and simultaneous loosening of the first tension member in the second mode of operation. In such embodiments, the brace may further include a control unit that is communicatively coupled with the motorized tensioning device and the method may further include: receiving a first input at the control unit, communicating a first instruction from the control unit to the motorized tensioning device, and in response to the first instruction, operating the motorized tensioning device in the first mode of operation to tension the first tension member and close and tighten the brace about the limb. The method may further include: receiving a second input via the control unit, communicating a second instruction from the control unit to the motorized tensioning device, and in response to the second instruction, operating the motorized tensioning device in the second mode of operation to tension the second tension member and open and loosen the brace from about the limb.

Having described several embodiments, it will be recognized by those of skill in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a process" includes a plurality of such processes and reference to "the device" includes reference to one or more devices and equivalents thereof known to those skilled in the art, and so forth.

Also, the words "comprise," "comprising," "include," "including," and "includes" when used in this specification and in the following claims are intended to specify the presence of stated features, integers, components, or steps, but they do not preclude the presence or addition of one or more other features, integers, components, steps, acts, or groups.

What is claimed is:

1. A lacing system for tightening an article about a limb, the lacing system comprising:
   a tensioning device that is coupleable with the article;
   a tension member that is coupled with the tensioning device and tensionable thereby;
   a pressure member that is coupleable with the article and operable with the tension member so as to be moveable radially inward into an interior of the article upon tensioning of the tension member, wherein
   radial movement of the pressure member into the interior of the article applies an inward pressure to the limb; and
   a pressure adjustment member that is coupled with the pressure member and moveable relative thereto, wherein movement of the pressure adjustment member relative to the pressure member varies a displacement of the pressure member into the interior of the article upon tensioning of the tension member such that the inward pressure applied to the limb is variable via the pressure adjustment member, and wherein the pressure member is configured so that an inner surface of the pressure member contacts the limb as the pressure member is displaced into the interior of the article.

2. The lacing system of claim 1, wherein the pressure adjustment member is slidable between a proximal end and a distal end of the pressure member.

3. The lacing system of claim 2, wherein the pressure member is wedge shaped with the distal end being thicker than the proximal end so that distal sliding of the pressure adjustment member causes an increased displacement of the pressure member into the interior of the article.

4. The lacing system of claim 1, wherein the pressure adjustment member is coupled atop the pressure member such that tensioning of the tension member causes the pressure adjustment member to press downward on a top surface of the pressure member, thereby causing the pressure member to displace inward into the interior of the article.

5. The lacing system of claim 4, wherein the pressure adjustment member includes a channel that guides the tension member atop the pressure member.

6. The lacing system of claim 1, wherein the article is a brace.

7. The lacing system of claim 1, wherein the pressure adjustment member is configured so that tensioning of the tension member causes the pressure adjustment member to slide toward a distal end of the pressure member.

8. The lacing system of claim 7, wherein the pressure member comprises a tapered configuration between a proximal end and the distal end, and wherein sliding of the pressure adjustment member along the tapered configuration of the pressure member effects an increased amount of displacement of the pressure member inward into the interior of the article.

9. A lacing system for tightening an article about a limb, the lacing system comprising:

a tensioning device that is coupled with the article;
a tension member that is coupled with the tensioning device and tensionable thereby;
a pressure member that is coupled with the article and positioned about the article so that an inner surface of the pressure member faces radially inward relative to an opening of the article, the pressure member being operable with the tension member so that tensioning of the tension member causes the pressure member to displace radially into the opening of the article and thereby apply pressure to the limb, wherein radial movement of the pressure member into the opening of the article applies an inward pressure to the limb; and
a pressure adjustment member that is coupled with the pressure member and that is operable to vary the radial displacement of the pressure member into the opening of the article upon tensioning of the tension member such that the inward pressure applied to the limb is variable via the pressure adjustment member;
wherein the pressure adjustment member is slidable between a proximal end and a distal end of the pressure member.

10. The lacing system of claim 9, wherein the pressure member is wedge shaped with the distal end being thicker than the proximal end so that distal sliding of the pressure adjustment member causes an increased displacement of the pressure member into the opening of the article.

11. The lacing system of claim 9, wherein the pressure adjustment member is coupled atop the pressure member such that tensioning of the tension member causes the pressure adjustment member to press downward on a top surface of the pressure member, thereby causing the pressure member to displace inward into the opening of the article.

12. The lacing system of claim 11, wherein the pressure adjustment member includes a channel that guides the tension member atop the pressure member.

13. The lacing system of claim 9, wherein the pressure member is positioned within the opening of the article so that an inner surface of the pressure member contacts the limb as the pressure member is displaced radially into the opening of the article.

14. The lacing system of claim 9, wherein the pressure member is configured so that an inner surface of the pressure member contacts a cushion within the interior of the article as the pressure member is displaced into the opening of the article.

15. The lacing system of claim 9, wherein the article is a brace.

16. The lacing system of claim 9, wherein the pressure adjustment member is configured so that tensioning of the tension member causes the pressure adjustment member to slide toward the distal end of the pressure member.

17. The lacing system of claim 16, wherein the pressure member comprises a tapered configuration between the proximal end and the distal end, and wherein sliding of the pressure adjustment member along the tapered configuration of the pressure member effects an increased amount of displacement of the pressure member inward into the opening of the article.

18. A method of configuring an article with a lacing system comprising:
providing a lacing system that includes:
a tensioning device;
a tension member that is coupled with the tensioning device and tensionable thereby;
a pressure member; and
a pressure adjustment member;
coupling the tensioning device with the article;
coupling the pressure member with the article so that an inner surface of the pressure member faces radially inward relative to an opening of the article; and
coupling the pressure adjustment member with the pressure member, wherein
the pressure member is operable with the tension member so that upon tensioning of the tension member, the pressure member is displaced radially into the opening of the article to apply pressure to the limb; and
the pressure adjustment member is operable to vary the radial displacement of the pressure member into the opening of the article upon tensioning of the tension member;
wherein the pressure member is positioned within the opening of the article so that an inner surface of the pressure member contacts the limb as the pressure member is displaced radially into the opening of the article.

19. The method of claim 15, wherein the pressure adjustment member is coupled with the pressure member so that the pressure adjustment member is slidable between a proximal end and a distal end of the pressure member.

20. The method of claim 19, wherein the pressure member is wedge shaped with the distal end being thicker than the proximal end so that distal sliding of the pressure adjustment member causes an increased displacement of the pressure member into the interior of the article.

21. The method of claim 15, wherein the pressure adjustment member is coupled atop the pressure member such that tensioning of the tension member causes the pressure adjustment member to press downward on a top surface of the pressure member, thereby causing the pressure member to displace radially into the opening of the article.

22. The method of claim 15, wherein the pressure adjustment member is configured so that tensioning of the tension member causes the pressure adjustment member to slide toward a distal end of the pressure member.

23. The method of claim 22, wherein the pressure member comprises a tapered configuration between a proximal end and a distal end, and wherein sliding of the pressure adjustment member along the tapered configuration of the pressure member effects an increased amount of displacement of the pressure member radially into the opening of the article.

24. A lacing system for tightening an article about a limb, the lacing system comprising:
a tensioning device that is coupleable with the article;
a tension member that is coupled with the tensioning device and tensionable thereby;
a pressure member that is coupleable with the article and operable with the tension member so as to be moveable radially inward into an interior of the article upon tensioning of the tension member, wherein
radial movement of the pressure member into the interior of the article applies an inward pressure to the limb; and
a pressure adjustment member that is coupled with the pressure member and moveable relative thereto, wherein movement of the pressure adjustment member relative to the pressure member varies a displacement of the pressure member into the interior of the article upon tensioning of the tension member such that the inward pressure applied to the limb is variable via the pressure adjustment member; and
wherein the pressure adjustment member is coupled atop the pressure member such that tensioning of the tension member causes the pressure adjustment member to press downward on a top surface of the pressure member thereby causing the pressure member to displace inward into the interior of the article.

25. The lacing system of claim 24, wherein the pressure adjustment member is slidable between a proximal end and a distal end of the pressure member.

26. The lacing system of claim 25, wherein the pressure adjustment member is configured so that tensioning of the tension member causes the pressure adjustment member to slide toward the distal end of the pressure member.

27. The lacing system of claim 25, wherein the pressure member is wedge shaped with the distal end being thicker than the proximal end so that distal sliding of the pressure adjustment member causes an increased displacement of the pressure member into the interior of the article.

28. The lacing system of claim 24, wherein the pressure adjustment member includes a channel that guides the tension member atop the pressure member.

29. The lacing system of claim 24, wherein the pressure member is configured so that an inner surface of the pressure member contacts the limb as the pressure member is displaced into the interior of the article.

30. The lacing system of claim 24, wherein the pressure member is configured so that an inner surface of the pressure member contacts a cushion within the interior of the article as the pressure member is displaced into the opening of the article.

31. The lacing system of claim 24, wherein the article is a brace.

32. A lacing system for tightening an article about a limb, the lacing system comprising:
   a tensioning device that is coupleable with the article;
   a tension member that is coupled with the tensioning device and tensionable thereby;
   a pressure member that is coupleable with the article and operable with the tension member so as to be moveable radially inward into an interior of the article upon tensioning of the tension member, wherein
   radial movement of the pressure member into the interior of the article applies an inward pressure to the limb; and
   a pressure adjustment member that is coupled with the pressure member and moveable relative thereto, wherein movement of the pressure adjustment member relative to the pressure member varies a displacement of the pressure member into the interior of the article upon tensioning of the tension member such that the inward pressure applied to the limb is variable via the pressure adjustment member, and
   wherein the pressure adjustment member is configured so that tensioning of the tension member causes the pressure adjustment member to slide toward a distal end of the pressure member.

33. The lacing system of claim 32, wherein the pressure member comprises a tapered configuration between a proximal end and the distal end, and wherein sliding of the pressure adjustment member along the tapered configuration of the pressure member effects an increased amount of displacement of the pressure member inward into the interior of the article.

34. The lacing system of claim 32, wherein the pressure adjustment member is coupled atop the pressure member such that tensioning of the tension member causes the pressure adjustment member to press downward on a top surface of the pressure member, thereby causing the pressure member to displace inward into the interior of the article.

35. The lacing system of claim 34, wherein the pressure adjustment member includes a channel that guides the tension member atop the pressure member.

36. The lacing system of claim 32, wherein the pressure member is configured so that an inner surface of the pressure member contacts the limb as the pressure member is displaced into the interior of the article.

37. The lacing system of claim 32, wherein the pressure member is configured so that an inner surface of the pressure member contacts a cushion within the interior of the article as the pressure member is displaced into the interior of the article.

38. The lacing system of claim 32, wherein the article is a brace.

* * * * *

UNITED STATES PATENT AND TRADEMARK OFFICE
CERTIFICATE OF CORRECTION

PATENT NO. : 9,872,790 B2  
APPLICATION NO. : 14/546883  
DATED : January 23, 2018  
INVENTOR(S) : James Capra et al.

Page 1 of 1

It is certified that error appears in the above-identified patent and that said Letters Patent is hereby corrected as shown below:

In the Claims

In Column 32, Line 20, Claim 19 remove "15" and insert --18--

In Column 32, Line 29, Claim 21 remove "15" and insert --18--

In Column 32, Line 35, Claim 22 remove "15" and insert --18--

Signed and Sealed this  
Eleventh Day of June, 2019

Andrei Iancu  
*Director of the United States Patent and Trademark Office*